(12) United States Patent
Ehrenfreund et al.

(10) Patent No.: US 7,241,721 B2
(45) Date of Patent: Jul. 10, 2007

(54) BIPHENYL DERIVATIVES AND THEIR USE AS FUNGICIDES

(75) Inventors: Josef Ehrenfreund, Basel (CH); Clemens Lamberth, Basel (CH); Hans Tobler, Basel (CH); Harald Walter, Basel (CH)

(73) Assignee: Syngenta Crop Protection, Inc., Greensboro, NC (US)

( * ) Notice: Subject to any disclaimer, the term of this patent is extended or adjusted under 35 U.S.C. 154(b) by 0 days.

(21) Appl. No.: 10/540,036

(22) PCT Filed: Dec. 15, 2003

(86) PCT No.: PCT/EP03/14248

§ 371 (c)(1),
(2), (4) Date: Jun. 22, 2005

(87) PCT Pub. No.: WO2004/058723

PCT Pub. Date: Jul. 15, 2004

(65) Prior Publication Data

US 2006/0100250 A1    May 11, 2006

(30) Foreign Application Priority Data

Dec. 24, 2002  (GB) ................................. 0230155.4

(51) Int. Cl.
*A01N 43/56*   (2006.01)
*C07D 231/18*  (2006.01)
(52) U.S. Cl. .................... 504/280; 514/406; 548/374.1
(58) Field of Classification Search ............ 548/375.1, 548/374.1; 504/280; 514/406
See application file for complete search history.

(56) References Cited

U.S. PATENT DOCUMENTS

| | | | |
|---|---|---|---|
| 3,859,338 A | 1/1975 | Engel et al. |
| 3,928,364 A | 12/1975 | Seeger et al. |
| 4,016,214 A | 4/1977 | Douglas et al. |
| 4,036,989 A | 7/1977 | Armitage et al. |
| 6,503,932 B2 | 1/2003 | Eicken |
| 6,515,000 B2 | 2/2003 | Eicken |
| 7,098,227 B2 | 8/2006 | Dunkel et al. |
| 2004/0029930 A1 | 2/2004 | Eicken |

(Continued)

FOREIGN PATENT DOCUMENTS

DE          2205732           8/1973

(Continued)

OTHER PUBLICATIONS

D.C. Naae et al.: "The solid-gas chlorination and bromination of a fluorinated of a fluorinated olefin." Tetrahedron Letters, vol. 32, 1976, pp. 2761-2764, p. 2762, table.

J.L. Chanal, et al., "Comparison of the Metabolism and Pharmacokinetics of Metbufen and Itanoxone and their Analogues in Rats." Arzneimittel Forschung, vol. 38, No. 10, 1988, pp. 1454-1460, p. 1456, compound la.

(Continued)

*Primary Examiner*—Kamal A. Saeed
*Assistant Examiner*—Joseph R. Kosack
(74) *Attorney, Agent, or Firm*—Rebecca Gegick

(57) ABSTRACT

A fungicidally active compound of formula (I): where Het is a substituted 5- or 6-membered heterocyclic ring; $R^1$ is hydrogen, formyl, CO—$C_{1-4}$ alkyl, COO—$C_{1-4}$ alkyl, $C_{1-4}$ alkoxy($C_{1-4}$)alkylene, CO—$C_{1-4}$ alkylenoxy($C_{1-4}$)alkyl, propargyl or allenyl; $R^2$, $R^3$, $R^4$ and $R^5$ are each, independently, hydrogen, halogen, methyl or $CF_3$; each $R^6$ is, independently, halogen, methyl or $CF_3$; $R^7$ is $(Z)_m C{=}C(Y^1)$, $(Z)_m C(Y^1){=}C(Y^2)(Y^3)$ or tri($C_{1-4}$)alkylsilyl; X is O or S; $Y^1$, $Y^2$ and $Y^3$ are each, independently, hydrogen, halogen, $C_{1-6}$ alkyl [optionally substituted by one or more substituents each independently selected from halogen, hydroxy, $C_{1-4}$ alkoxy, $C_{1-4}$ haloalkoxy, $C_{1-4}$ alkylthio, $C_{1-4}$ haloalkylthio, $C_{1-4}$ alkylamino, di($C_{1-4}$)alkylamino, $C_{1-4}$ alkoxycarbonyl, $C_{1-4}$ alkylcarbonyloxy and tri($C_{1-4}$)alkylsilyl], $C_{2-4}$ alkenyl [optionally substituted by one or more substituents each independently selected from halogen], $C_{2-4}$ alkynyl [optionally substituted by one or more substituents each independently selected from halogen], $C_{3-7}$ cycloalkyl [optionally substituted by one or more substituents each independently selected from halogen, $C_{1-4}$ alkyl and $C_{1-4}$ haloalkyl] or tri($C_{1-4}$)alkylsilyl; Z is $C_{1-4}$ alkylene [optionally substituted by one or more substituents each independently selected from hydroxy, cyano, $C_{1-4}$ alkoxy, halogen, $C_{1-4}$ haloalkyl, $C_{1-4}$ haloalkoxy, $C_{1-4}$ alkylthio, COOH and COO—$C_{1-4}$ alkyl]; m is 0 or 1; and n is 0, 1 or 2; the invention also relates to novel intermediates used in the preparation of these compounds, to agrochemical compositions which comprise at least one of the novel compounds as active ingredient and to the use of the active ingredients or compositions in agriculture or horticulture for controlling or preventing infestation of plants by phytopathogenic microorganisms, preferably fungi

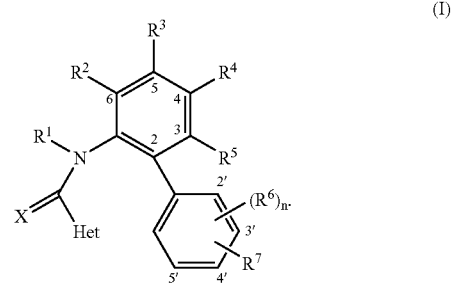

(I)

11 Claims, No Drawings

U.S. PATENT DOCUMENTS

| | | |
|---|---|---|
| 2004/0044060 A1 | 3/2004 | Muller |
| 2004/0077692 A1 | 4/2004 | Eicken |
| 2005/0124815 A1 | 6/2005 | Elbe et al. |
| 2006/0116414 A1 | 6/2006 | Dunkel et al. |
| 2006/0148886 A1 | 7/2006 | Dunkel et al. |

FOREIGN PATENT DOCUMENTS

| | | |
|---|---|---|
| DE | 2205732 | 5/1976 |
| DE | 10204390 | 8/2003 |
| DE | 10204391 | 8/2003 |
| DE | 10215292 | 8/2003 |
| DE | 10218231 | 11/2003 |
| JP | 2001302605 | 10/2001 |
| WO | 0208197 | 1/2002 |
| WO | WO 0208195 A1 * | 1/2002 |
| WO | 2004045282 | 6/2004 |

OTHER PUBLICATIONS

D.G. Naae: "Reaction of Crystalline Fluoro Olefins with Bromine Vapour." Journal of Organic Chemistry, vol. 42, No. 10, 1977, pp. 1780-1783, p. 1781, compound 4.

M.W. Renoll: "Vinyl Aromatic Compounds III, Fluorinated Derivatives." Journal of the Americal Chemical Society, vol. 68, 1946, pp. 1159-1161, p. 1159, compound 2.

H. Cousse et al.: "Synthese, structure et activite hypocholereroleminante d'une serie d'acides gamma-aryl, gamma-oxo butyriques substitutes et derives." European Journal of Medicinal Chemistry, vol. 22, 1987, pp. 45-57, tables, VI, VII.

D.C. Naae et al: "The solid-gas chlorinateion and bromination of a fluorinated olefin." Tetrahedron Letters, vol. 32, 1976, pp. 2761-2764, XP001181810, p. 2762, table.

J.L Chanal et al.: "Comparison of the Metabolism and Pharmacokinetics of Metbufen and Itanoxone and their Analogues in Rats." Arzneimittel Forschung, vol. 38, No. 10, 1988, pp. 1454-1460, XP002230049, p. 1781, compound 4.

D.G. Naae: "Reaction of Crystalline Fluoro Olefins with Bromine Vapour." Journal of Organic Chemistry, vol. 42, No. 10, 1977, pp. 1780-1783, XP002230049, p. 1781, compound 4.

M.W. Renoll: "Vinyl Aromatic Compounds III. Fluorinated Derivatives.", Journal of the American Chemical Society, vol. 68, 1946, pp. 1159-1161, XP001181808, p. 1159, compound 2.

H. Cousse et al: "Synthese, structure et activite hypocholereroleminate d'une serie d'acides gamma-aryl, gamma-oxo butyriques substitutes et derives," European Journal of Medicinal Chemistry, vol. 22, 1987, pp. 45-57, XP001181809, Tables VI, VII.

* cited by examiner

BIPHENYL DERIVATIVES AND THEIR USE AS FUNGICIDES

"This application is a 371 of International Application No. PCT/EP2003/014248 filed Dec. 15, 2003, which claims priority to GB 0230155.4, filed Dec. 24, 2002, the contents of which are incorporated herein by reference."

The present invention relates to novel carboxamide derivatives as active ingredients which have microbiocidal activity, in particular fungicidal activity. The invention also relates to preparation of these active ingredients, to novel diphenyl derivatives used as intermediates in the preparation of these active ingredients, to preparation of these novel intermediates, to agrochemical compositions which comprise at least one of the novel active ingredients, to preparation of these compositions and to use of the active ingredients or compositions in agriculture or horticulture for controlling or preventing infestation of plants by phytopathogenic microorganisms, preferably fungi.

Fungicidally active carboxamide derivatives are disclosed in JP2001072510, JP2001072508, JP2001072507 and JP2001302605.

Certain amino- or halo-substituted diphenyl derivatives are disclosed in DE2205732 and JP2001302605.

The present invention provides a compound of formula (I):

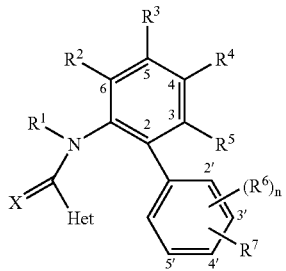

(I)

where Het is a 5- or 6-membered heterocyclic ring containing one to three heteroatoms, each independently selected from oxygen, nitrogen and suphur, provided that the ring is not 1,2,3-triazole, the ring being substituted by one, two or three groups $R^y$; $R^1$ is hydrogen, formyl, CO—$C_{1-4}$ alkyl, COO—$C_{1-4}$ alkyl, $C_{1-4}$ alkoxy($C_{1-4}$)alkylene, CO—$C_{1-4}$ alkylenoxy($C_{1-4}$)alkyl, propargyl or allenyl; $R^2$, $R^3$, $R^4$ and $R^5$ are each, independently, hydrogen, halogen, methyl or $CF_3$; each $R^6$ is, independently, halogen, methyl or $CF_3$; $R^7$ is $(Z)_m C\equiv C(Y^1)$, $(Z)_m C(Y^1)=C(Y^2)(Y^3)$ or tri($C_{1-4}$)alkylsilyl; each $R^y$ is, independently, halogen, $C_{1-3}$ alkyl, $C_{1-3}$ haloalkyl, $C_{1-3}$ alkoxy($C_{1-3}$)alkylene or cyano; X is O or S; $Y^1$, $Y^2$ and $Y^3$ are each, independently, hydrogen, halogen, $C_{1-6}$ alkyl [optionally substituted by one or more substituents each independently selected from halogen, hydroxy, $C_{1-4}$ alkoxy, $C_{1-4}$ haloalkoxy, $C_{1-4}$ alkylthio, $C_{1-4}$ haloalkylthio, $C_{1-4}$ alkylamino, di($C_{1-4}$)alkylamino, $C_{1-4}$ alkoxycarbonyl, $C_{1-4}$ alkylcarbonyloxy and tri($C_{1-4}$)alkylsilyl], $C_{2-4}$ alkenyl [optionally substituted by one or more substituents each independently selected from halogen], $C_{2-4}$ alkynyl [optionally substituted by one or more substituents each independently selected from halogen], $C_{3-7}$ cycloalkyl [optionally substituted by one or more substituents each independently selected from halogen, $C_{1-4}$ alkyl and $C_{1-4}$ haloalkyl] or tri($C_{1-4}$)alkylsilyl; Z is $C_{1-4}$ alkylene [optionally substituted by one or more substituents each independently selected from hydroxy, cyano, $C_{1-4}$ alkoxy, halogen, $C_{1-4}$ haloalkyl, $C_{1-4}$ haloalkoxy, $C_{1-4}$ alkylthio, COOH and COO—$C_{1-4}$ alkyl]; m is 0 or 1; and n is 0, 1 or 2.

In one particular aspect, the present invention provides a compound of formula (I) as defined above where $Y^1$, $Y^2$ and $Y^3$ are each, independently, hydrogen, halogen, $C_{1-4}$ alkyl [optionally substituted by one or more substituents each independently selected from halogen, hydroxy, $C_{1-4}$ alkoxy, $C_{1-4}$ haloalkoxy, $C_{1-4}$ alkylthio, $C_{1-4}$ haloalkylthio, $C_{1-4}$ alkylamino, di($C_{1-4}$)alkylamino, $C_{1-4}$ alkoxycarbonyl and tri($C_{1-4}$)alkylsilyl], $C_{2-4}$ alkenyl [optionally substituted by one or more substituents each independently selected from halogen], $C_{2-4}$ alkynyl [optionally substituted by one or more substituents each independently selected from halogen], $C_{3-7}$ cycloalkyl [optionally substituted by one or more substituents each independently selected from halogen, $C_{1-4}$ alkyl and $C_{1-4}$ haloalkyl] or tri($C_{1-4}$)alkylsilyl.

In one aspect, the present invention provides a compound of formula (I) as defined above where Z is $C_{1-4}$ alkylene [optionally substituted by one or more substituents each independently selected from hydroxy, cyano, $C_{1-4}$ alkoxy, $C_{1-4}$ haloalkoxy, $C_{1-4}$ alkylthio, COOH and COO—$C_{1-4}$ alkyl].

In one aspect, the present invention provides a compound of formula (I) as defined above provided that $R^7$ is not $C_{2-6}$ alkenyl when X is O; $R^1$ is hydrogen; one of $R^2$, $R^3$, $R^4$ and $R^5$ is fluorine and the others are all hydrogen; n is 1; and Het is

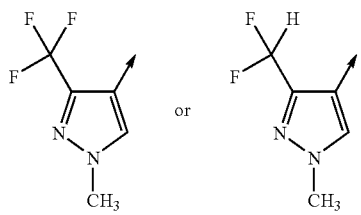

In another aspect, the present invention provides a compound of formula (I) as defined above provided that $R^7$ is not $C_{2-6}$ alkenyl when X is O; $R^1$, $R^2$, $R^3$, $R^4$ and $R^5$ are all hydrogen; and Het is

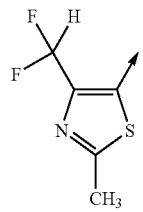

In a further aspect, the present invention provides a compound of formula (I) as defined above provided that $R^7$ is not $C_{2-6}$ alkenyl when X is O; $R^1$, $R^2$, $R^3$, $R^4$ and $R^5$ are all hydrogen; n is 1; and Het is

In yet another aspect, the present invention provides a compound of formula (I) as defined above provided that $R^7$ is not $C_{2-6}$ alkenyl in the 4' position when X is O; $R^1$, $R^3$ and $R^5$ are all hydrogen; $R^2$ and $R^4$ are each, independently, hydrogen or fluorine; n is 0; or n is 1; or n is 2 and the two independent $R^6$ substituents are in positions 2',3' or 2', 5' or 3',5'; and Het is Halogen is fluorine, chlorine, bromine or iodine [preferably fluorine, chlorine or bromine].

Each alkyl moiety is a straight or branched chain and is, for example, methyl, ethyl, n-propyl, n-butyl, iso-propyl, n-butyl, sec-butyl, iso-butyl or tert-butyl. Likewise, each alkylene moiety is a straight or branched chain.

Haloalkyl moieties are alkyl moieties which are substituted by one or more of the same or different halogen atoms and are, for example, $CF_3$, $CF_2Cl$, $CHF_2$, $CH_2F$, $CCl_3$, $CF_3CH_2$, $CHF_2CH_2$, $CH_2FCH_2$, $CH_3CHF$ or $CH_3CF_2$.

Alkenyl and alkynyl moieties can be in the form of straight or branched chains. The alkenyl moieties, where appropriate, can be of either the (E)- or (Z)-configuration. Examples are vinyl, allyl, ethynyl and propargyl.

Cycloalkyl includes cyclopropyl, cyclobutyl, cyclopentyl, cyclohexyl and cycloheptyl.

In tri($C_{1-4}$)alkylsilyl and in di($C_{1-4}$)alkylamino, each alkyl moiety is selected independently.

Throughout this description, Me stands for methyl and Et stands for ethyl.

It is preferred that Het is pyrazole, pyrrole, thiophene, furan, thiazole, isothiazole, oxazole, isoxazole, pyridine, pyrazine, pyrimidine, pyridazine, 5.6-dihydropyran or 5.6-dihydro-1.4-oxathiine [more preferably pyrazole, pyrrole, thiophene, furan, thiazole, oxazole, pyridine, pyrimidine, pyridazine or 5.6-dihydropyran; yet more preferably pyrazole, pyrrole, pyridine or thiazole; and even more preferably pyrazole, pyrrole or thiazole].

In one aspect it is preferred that Het is pyrazole, pyrrole, thiophene, furan, thiazole, isothiazole, oxazole, isoxazole, pyrazine, pyrimidine, pyridazine, 5.6-dihydropyran or 5.6-dihydro-1.4-oxathiine [more preferably pyrazole, pyrrole, thiophene, furan, thiazole, oxazole, pyrimidine, pyridazine or 5.6-dihydropyran and even more preferably pyrazole, pyrrole or thiazole].

Preferably $R^1$ is hydrogen, propargyl, allenyl, formyl, COMe, COEt or $COCH_2OMe$.

More preferably $R^1$ is hydrogen.

Preferably $R^2$ is hydrogen.

Preferably $R^3$ is hydrogen.

Preferably $R^4$ is hydrogen.

Preferably $R^5$ is hydrogen or halogen.

More preferably $R^5$ is hydrogen or fluorine.

Even more preferably $R^5$ is hydrogen.

In one aspect of the invention $R^7$ is tri($C_{1-4}$)alkylsilyl.

Preferably $Y^1$, $Y^2$ and $Y^3$ are, independently, hydrogen, halogen, $C_{1-6}$ alkyl, $C_{1-3}$ haloalkyl, $C_{1-4}$(haloalkoxy)$C_{1-4}$alkyl, $C_{1-4}$(haloalkylthio)$C_{1-4}$ alkyl, trimethylsilyl, $C_{2-4}$ alkenyl, $C_{2-4}$ haloalkenyl or $C_{3-4}$ cycloalkyl (optionally substituted by one or more substituents each independently selected from halogen and $C_{1-2}$ alkyl).

Preferably Z is $C_{1-2}$ alkylene [which may be optionally substituted by one or more substituents each independently selected from halogen, $C_{1-4}$ haloalkyl and $C_{1-4}$ haloalkoxy].

Preferably $R^7$ is in the 4' position.

Preferably $R^7$ is vinyl [optionally substituted by one to three substituents each independently selected from halogen, $C_{1-4}$ alkyl, $C_{1-3}$ haloalkyl, $C_{3-6}$ cycloalkyl (optionally substituted by one to five substituents each independently selected from halogen, $CH_3$ and $C_{1-2}$ haloalkyl) and trimethylsilyl], ethynyl [optionally substituted by one substituent selected from cyclopropyl, cyclopentyl and cyclohexyl (each optionally substituted by one to five substituents each independently selected from halogen, $CH_3$ and $C_{1-2}$ haloalkyl), halogen, $C_{1-6}$ alkyl, $C_{1-4}$ haloalkyl, $C_{2-4}$ alkenyl, $C_{2-4}$ haloalkenyl and tri($C_{1-4}$)alkylsilyl], allyl [optionally substituted by one to three substituents each independently selected from halogen, $CH_3$, $C_{1-2}$ haloalkyl and trimethylsilyl], propargyl [optionally substituted by one to three substituents each independently selected from halogen, $C_{1-4}$ alkyl, $C_{1-2}$ haloalkyl and trimethylsilyl] or tri($C_{1-4}$)alkylsilyl.

In one particular aspect $R^7$ is preferably vinyl [optionally substituted by one to three substituents each independently selected from halogen, $C_{1-4}$ alkyl, $C_{1-3}$ haloalkyl, $C_{3-6}$ cycloalkyl and trimethylsilyl], ethynyl [optionally substituted by one substituent selected from halogen, $C_{1-4}$ alkyl, $C_{1-2}$ haloalkyl, cyclopropyl (optionally substituted by one to five substituents each independently selected from halogen, $CH_3$, $C_{1-2}$ haloalkyl and trimethylsilyl) and trimethylsilyl], allyl [optionally substituted by one to three substituents each independently selected from halogen, $CH_3$, $C_{1-2}$ haloalkyl and trimethylsilyl], propargyl [optionally substituted by one to three substituents each independently selected from halogen, $CH_3$, $C_{1-2}$ haloalkyl and trimethylsilyl] or tri($C_{1-4}$) alkylsilyl.

In another particular aspect $R^7$ is preferably vinyl [optionally substituted by one to three substituents each independently selected from halogen, $C_{1-4}$ alkyl, $C_{1-3}$ haloalkyl, $C_{3-6}$ cycloalkyl and trimethylsilyl], ethynyl [optionally substituted by one substituent selected from halogen, $C_{1-4}$ alkyl, $C_{1-2}$ haloalkyl and trimethylsilyl], allyl [optionally substituted by one to three substituents each independently selected from halogen, $CH_3$, $C_{1-2}$ haloalkyl and trimethylsilyl], propargyl [optionally substituted by one to three substituents each independently selected from halogen, $CH_3$, $C_{1-2}$ haloallyl and trimethylsilyl] or tri($C_{1-4}$)alkylsilyl.

More preferably $R^7$ is $CH=CH_2$, $CH=CH(CH_3)$, $CH=CHSiMe_3$, $CH=CF_2$, $CH=CCl_2$, $C(CH_3)=CCl_2$, $CH=CBr_2$, $C(CH_3)=CBr_2$, $C(CH_3)=CF_2$, $CH=CFCl$, $CH=CFBr$, $C(CH_3)=CFCl$, $C(CH_3)=CFBr$, $CH=CFMe$, $CH=CBrMe$, $CH=CClMe$, $CH=CHBr$, $CH=CHF$, $CH=CHCl$, $CF=CF_2$, $CCl=CF_2$, $CCl=CH_2$, $CBr=CH_2$, $CF=CH_2$, $C(CF_3)=CFBr$, $C(CF_3)=CFCl$, $C(CF_3)=CBr_2$, $C(CF_3)=CCl_2$, $C(CF_3)=CF_2$, $C(CF_3)=CH_2$, $CF=CHF$, $CH=CHCF_3$, $CH=CFCF_2Cl$, $CH=CClCF_2Cl$, $CH=CBrCF_2Cl$, $CH=C(CF_3)_2$, $CH=CHC_2F_5$, $CH=CHCF(CF_3)_2$, $C(CH_3)=CHCF_3$, $C(CH_3)=CFCF_3$, $C(CH_3)=CClCF_3$, $C(CH_3)=CBrCF_3$, $CH=CClCF_3$, $CH=CClC_2F_5$, $CH=CBrCF_3$, $CH=CFC_2F_5$, $CH=CFCF_3$, $CH_2CH=CH_2$, $CH_2CH=CF_2$, $CH_2CH=CCl_2$, $CH_2CH=CBr_2$, $CH_2CH=CFBr$, $CH_2CH=CFCl$, $CH_2CH=CClCF_3$, $CH_2CH=CHSiMe_3$, $C≡CH$, $C≡CSiMe_3$, $C≡CSiEt_3$, $C≡CSiMe_2C(CH_3)_3$, $C≡CCl$, $C≡CBr$, $C≡CF$, $C≡CCF_3$, $C≡CCF_2H$, $C≡CCF_2Cl$, $C≡CCF_2Me$, $C≡CCF_2Et$, $C≡CCHFCl$, $C≡CCF_2Br$, $C≡CC_2F_5$, $C≡CCF(CF_3)_2$, $C≡CCHF(CF_3)$, $C≡CCH_2F$, $C≡CCH(Me)F$, $C≡CCH(Et)F$, $C≡CMe$, $C≡CCH_2Me$, $C≡CCHMe_2$, $C≡CCH_2CHMe_2$, $C≡CCMe_3$, $C≡CCH_2CMe_3$, $C≡CCH_2SiMe_3$, $C≡CCMe_2Cl$, $C≡CCMe_2F$, $C≡CCH_2OMe$, $C≡CCH_2CF_3$, $C≡CCMe_2OMe$, $C≡CCMe_2OH$, C≡CCMe₂OCOMe, C≡CC(Me)=CH₂, C≡CCF=CF₂, C≡C(cyclopropyl), C≡C(cyclopentyl), C≡C(1-F-cyclopentyl), CH₂C≡CH, CF₂C≡CH, CHFC≡CH, CH(CF₃)C≡CH, SiMe₃, CH₂C≡CCMe₃ or CH₂C≡CSiMe₃.

In one particular aspect R⁷ is more preferably CH=CH₂, CH=CH(CH₃), CH=CHSiMe₃, CH=CF₂, CH=CCl₂, C(CH₃)=CCl₂, CH=CBr₂, CF=CF₂, CCl=CH₂, CBr=CH₂, CF=CH₂, CF=CHF, CH=CHCF₃, CH=CClCF₃, CH=CBrCF₃, CH₂CH=CH₂, CH₂CH=CHSiMe₃, C≡CH, C≡CSiMe₃, C≡CSiEt₃, C≡CSiMe₂C(CH₃)₃, C≡CCl, C≡CBr, C≡CCF₃, C≡CCF₂H, C≡CCF₂Cl, C≡CCF₂Br, C≡CCF(CF₃)₂, C≡CMe, C≡CCHMe₂, C≡CCMe₃, C≡CCMe₂Cl, C≡CCH₂OMe, C≡C(cycloC₃H₅), C≡C(cycloC₅H₉), CH₂C≡CH, SiMe₃ or CH₂C≡CSiMe₃.

Even more preferably R⁷ is CH=CF₂, CH=CCl₂, C(CH₃)=CCl₂, CH=CBr₂, C(CH₃)=CBr₂, C(CH₃)=CF₂, CH=CFCl, CH=CFBr, C(CH₃)=CFCl, C(CH₃)=CFBr, CH=CHBr, CH=CHF, CH=CHCl, CCl=CH₂, CH=CHCF₃, CH=CFCF₂Cl, CH=CClCF₂Cl, CH=CBrCF₂Cl, CH=C(CF₃)₂, CH=CHC₂F₅, CH=CHCF(CF₃)₂, C(CH₃)=CHCF₃, CH=CClCF₃, CH=CClC₂F₅, CH=CFC₂F₅, CH=CBrCF₃, CH=CFCF₃, CH₂CH=CClCF₃, CH₂CH=CCl₂, CH₂CH=CBr₂, C≡CH, C≡CSiMe₃, C≡CSiEt₃, C≡CSiMe₂C(CH₃)₃, C≡CCl, C≡CCF₃, C≡CCF₂H, C≡CCF₂Cl, C≡CCHFCl, C≡CCF₂Me, C≡CCF₂Et, C≡CCHFEt, C≡CCF₂Br, C≡CCF(CF₃)₂, C≡CCF₂CF₃, C≡CCHF(CF₃), C≡CCH₂F, C≡CCH(Me)F, C≡CMe, C≡CCHMe₂, C≡CCH₂Me, Cs≡CCH₂CHMe₂, C≡CCMe₃, C≡CCH₂CMe₃, C≡CCMe₂F, C≡CCH₂CF₃, C≡C(cyclopropyl), C≡C(cyclopentyl), C≡C(1-F-cyclopentyl), C≡CC(Me)=CH₂, C≡CCF=CF₂, C≡CCH₂SiMe₃, CH₂C≡CH, CF₂C≡CH or CHFC≡CH.

In one particular aspect R⁷ is even more preferably CH=CH₂, CH=CHSiMe₃, CH=CF₂, CH=CCl₂, CH=CBr₂, CF=CF₂, CCl=CH₂, CBr=CH₂, CF=CHF, CH=CHCF₃, CH=CClCF₃, C≡CH, C≡CSiMe₃, C≡CCl, C≡CBr, C≡CCF₃, C≡CMe, C≡CCMe₃, C≡CCHMe₂, C≡C(cycloC₃H₅), CH₂C≡CH, SiMe₃ or CH₂C≡CSiMe₃.

Yet more preferably R⁷ is CH=CF₂, CH=CCl₂, CH=CBr₂, CH=CFCl, CH=CFBr, CH=CHBr, CH=CHF, CH=CHCl, CCl=CH₂, CH=CHCF₃, CH=CFCF₂Cl, CH=CClCF₂Cl, CH=CBrCF₂Cl, CH=C(CF₃)₂, CH=CHC₂F₅, CH=CClCF₃, CH=CBrCF₃, CH=CFCF₃, C≡CH, C≡CSiMe₃, C≡CCl, C≡CCF₃, C≡CCF₂H, C≡CCHFCl, C≡CCHF(CF₃), C≡CCF₂Cl, C≡CCF₂Me, C≡CCF₂Br, C≡CCF₂CF₃, C≡CCH₂F, C≡CCH(Me)F, C≡CMe, C≡CCHMe₂, C≡CCMe₃, C≡CCCH₂CMe₃, C≡CCMe₂F, C≡CCH₂CF₃, C≡C(cyclopropyl), C≡C(cyclopentyl), C≡C(1-F-cyclopentyl), CH₂C≡CH, CF₂C≡CH, CHFC≡CH or C≡CCH₂Me.

In one particular aspect R⁷ is yet more preferably CH=CHSiMe₃, CH=CF₂, CH=CCl₂, CH=CBr₂, CF=CF₂, CCl=CH₂, CBr=CH₂, CF=CHF, CH=CHCF₃, CH=CClCF₃, C≡CH, C≡CSiMe₃, C≡CCl, C≡CBr, C≡CCF₃, C≡CMe, C≡CCMe₃, C≡CCHMe₂, C≡C(cycloC₃H₅), CH₂C≡CH, SiMe₃ or CH₂C≡CSiMe₃.

Preferably nitrogen atoms in the Het ring are, independently, either unsubstituted or substituted by R^y.

When R^y is a substituent on a nitrogen atom it is preferably C₁₋₃ alkyl, C₁₋₃ haloalkyl or methoxymethylene; more preferably C₁₋₂ alkyl, CF₃, CF₂Cl, CHF₂, CH₂F or methoxymethylene; even more preferably methyl, CHF₂ or methoxymethylene; yet more preferably methyl or methoxymethylene; and most preferably methyl.

Preferably carbon atoms in the Het ring which are not bonded to the atom substituted by CXNR¹ are, independently, either unsubstituted or substituted by R^y.

When R^y is a substituent on a carbon atom which is not bonded to the atom substituted by CXNR¹ it is preferably halogen, C₁₋₃ alkyl, C₁₋₃ haloalkyl or methoxymethylene; more preferably chloro, methoxymethylene, CH₃, CHF₂ or CF₃; yet more preferably chloro, CH₃, CHF₂ or CF₃; and even more preferably CH₃ or CF₃. There may be one or two carbon atoms in the Het ring bonded to the atom substituted by CXNR¹; preferably such carbon atoms are, independently, either unsubstituted or substituted by R^y.

When R^y is a substituent on a carbon atom bonded to the atom substituted by CXNR¹ it is preferably halogen, C₁₋₃ alkyl or C₁₋₃ haloalkyl; more preferably chloro, fluoro, bromo, C₁₋₂ alkyl, CF₃, CF₂Cl, CHF₂, CH₂F; and even more preferably chloro, fluoro, bromo, methyl, CF₃, CHF₂ or CH₂F.

More preferably, when there is only one carbon atom in the Het ring bonded to the atom substituted by CXNR¹ that carbon atom is substituted by R^y.

More preferably, when there are two carbon atoms in the Het ring bonded to the atom substituted by CXNR¹ one such carbon atom is substituted by R^y and the other carbon atom is either unsubstituted or is substituted by fluoro, chloro or methyl.

Preferably m is 0.

Preferably n is 0.

Preferably X is O.

Compounds of formula (II):

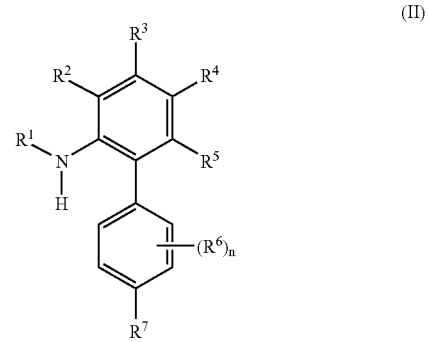

where R¹, R², R³, R⁴, R⁵, R⁶, R⁷ and n are as defined above for a compound of formula (I), also novel [except for the compound of formula (II) where R¹, R², R³, R⁴ and R⁵ are each hydrogen, n is 0 and R⁷ is CH=CHCH₂CO₂H] and are useful as intermediates in the preparation of compounds of formula (I).

Therefore, in another aspect the present invention provides a compound of formula (II), where R¹, R², R³, R⁴, R⁵, R⁶, R⁷ and n are as defined above for a compound of formula (I) provided that when R¹, R², R³, R⁴ and R⁵ are each hydrogen and n is 0 then R⁷ is not CH=CHCH₂CO₂H.

The preferred values for R¹, R², R³, R⁴, R⁵, R⁶, R⁷ and n for a compound of formula (II) are as defined above for a compound of formula (I).

Many compounds of formula (III):

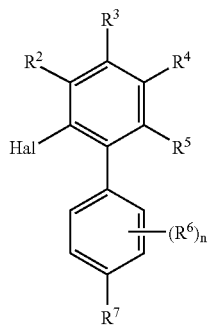

(III)

where $R^2$, $R^3$, $R^4$, $R^5$, $R^6$, $R^7$ and n are as defined above for a compound of formula (I) and Hal is bromo, chloro or iodo, are also novel and are useful as intermediates in the preparation of compounds of formula (I).

Certain compounds of formula (III) are already known; Table 0 shows known compounds of formula (IIa) where Hal, $R^2$, $R^3$, $R^4$ and $R^7$ are as defined in Table 0.

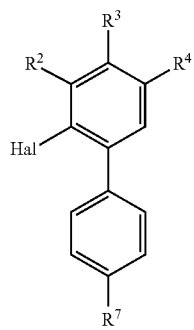

(IIIa)

TABLE 0

| Hal | $R^2$ | $R^3$ | $R^4$ | $R^7$ |
|---|---|---|---|---|
| Cl | Cl | H | H | C(CH₃)=CH—CH₂—OH |
| Br | H | Me | H | C(CF₃)=CF₂ |
| Br | H | Me | Br | C(CF₃)=CF₂ |
| Cl | H | H | H | C≡CH |
| Cl | H | H | H | CH=CH—CH₂—CH₂—OH |
| Cl | H | H | H | C(CH₃)=CH—CH₂—OH |
| Cl | H | H | H | C(CH₃)=CH—C(=O)—OC₂H₅ |
| Cl | H | H | H | C(CH₃)=CH—CH(OH)CH₃ |
| Cl | H | H | H | CH=CH—CH(OH)CH₃ |

Therefore, in a further aspect the present invention provides a compound of formula (III), where $R^2$, $R^3$, $R^4$, $R^5$, $R^6$, $R^7$ and n are as defined above for a compound of formula (I) and Hal is bromo, chloro or iodo; provided that the compound is not a compound of formula (IIIa) according to Table 0.

The preferred values for $R^2$, $R^3$, $R^4$, $R^5$, $R^6$, $R^7$ and n for a compound of formula (III) are as defined above for a compound of formula (I).

Preferably Hal is bromo or chloro.

More preferably Hal is bromo.

The compounds of formulae (I), (II) and (III) may exist as different geometric or optical isomers or in different tautomeric forms. For each formula, this invention covers all such isomers and tautomers and mixtures thereof in all proportions as well as isotopic forms such as deuterated compounds.

The compounds in Tables 1 to 13 below illustrate compounds of the invention.

TABLE 1

| Compound No. | $R^1$ | $R^7$ | $R^8$ | $R^9$ | $R^{10}$ | X |
|---|---|---|---|---|---|---|
| 1.01 | H | C≡CH | H | Me | CF₃ | O |
| 1.02 | H | C≡CH | H | Me | CF₃ | S |
| 1.03 | H | C≡CH | H | Me | CF₂H | O |
| 1.04 | propargyl | C≡CH | H | Me | CF₃ | O |
| 1.05 | H | C≡CH | F | Me | Me | O |
| 1.06 | H | C≡CH | H | CH₂OMe | CF₃ | O |
| 1.07 | allenyl | C≡CH | H | Me | CF₃ | O |
| 1.08 | H | C≡CSiMe₃ | H | Me | CF₃ | O |
| 1.09 | H | C≡CSiMe₃ | H | Me | CF₃ | S |
| 1.10 | H | C≡CSiMe₃ | H | Me | CF₂H | O |
| 1.11 | H | C≡CSiMe₃ | H | Me | Me | O |
| 1.12 | H | C≡CCl | H | Me | CF₃ | O |
| 1.13 | H | C≡CCl | H | Me | CF₂H | O |
| 1.14 | H | C≡CCl | H | Me | Me | O |
| 1.15 | H | C≡CBr | H | Me | CF₃ | O |
| 1.16 | H | C≡CBr | H | Me | CF₂H | O |
| 1.17 | H | C≡CBr | F | Me | Me | O |
| 1.18 | H | C≡CCF₃ | H | Me | CF₃ | O |
| 1.19 | H | C≡CCF₃ | H | Me | CF₂H | O |
| 1.20 | H | C≡CCF₃ | F | Me | Me | O |
| 1.21 | allenyl | C≡CCF₃ | H | Me | CF₃ | O |
| 1.22 | H | CH=CH₂ | H | Me | CF₃ | O |
| 1.23 | H | CH=CH₂ | H | Me | CF₃ | S |
| 1.24 | H | CH=CH₂ | H | Me | CF₂H | O |
| 1.25 | propargyl | CH=CH₂ | H | Me | CF₃ | O |

TABLE 1-continued

| Compound No. | R¹ | R⁷ | R⁸ | R⁹ | R¹⁰ | X |
|---|---|---|---|---|---|---|
| 1.26 | H | CH=CH$_2$ | F | Me | Me | O |
| 1.27 | H | CH=CH$_2$ | H | CH$_2$OMe | CF$_3$ | O |
| 1.28 | allenyl | CH=CH$_2$ | H | Me | CF$_3$ | O |
| 1.29 | H | CH=CF$_2$ | H | Me | CF$_3$ | O |
| 1.30 | H | CH=CF$_2$ | H | Me | CF$_2$H | O |
| 1.31 | H | CH=CF$_2$ | F | Me | Me | O |
| 1.32 | H | CH=CCl$_2$ | H | Me | CF$_3$ | O |
| 1.33 | H | CH=CCl$_2$ | H | Me | CF$_2$H | O |
| 1.34 | H | CH=CCl$_2$ | F | Me | Me | O |
| 1.35 | H | CH=CBr$_2$ | H | Me | CF$_3$ | O |
| 1.36 | H | CH=CBr$_2$ | H | Me | CF$_2$H | O |
| 1.37 | H | CH=CBr$_2$ | F | Me | Me | O |
| 1.38 | H | CF=CF$_2$ | H | Me | CF$_3$ | O |
| 1.39 | H | CF=CF$_2$ | H | Me | CF$_2$H | O |
| 1.40 | H | CF=CF$_2$ | F | Me | Me | O |
| 1.41 | H | CCl=CH$_2$ | H | Me | CF$_3$ | O |
| 1.42 | H | CCl=CH$_2$ | H | Me | CF$_2$H | O |
| 1.43 | H | CCl=CH$_2$ | F | Me | Me | O |
| 1.44 | H | CBr=CH$_2$ | H | Me | CF$_3$ | O |
| 1.45 | H | CBr=CH$_2$ | H | Me | CF$_2$H | O |
| 1.46 | H | CBr=CH$_2$ | F | Me | Me | O |
| 1.47 | H | CF=CHF | H | Me | CF$_3$ | O |
| 1.48 | H | CF=CHF | H | Me | CF$_2$H | O |
| 1.49 | H | CF=CHF | F | Me | Me | O |
| 1.50 | H | CH=CHSiMe$_3$ | H | Me | CF$_3$ | O |
| 1.51 | H | CH=CHSiMe$_3$ | H | Me | CF$_2$H | O |
| 1.52 | H | CH=CHSiMe$_3$ | F | Me | Me | O |
| 1.53 | H | CH=CHCF$_3$ | H | Me | CF$_3$ | O |
| 1.54 | H | CH=CHCF$_3$ | H | Me | CF$_2$H | O |
| 1.55 | H | CH=CHCF$_3$ | F | Me | Me | O |
| 1.56 | H | CH=CClCF$_3$ | H | Me | CF$_3$ | O |
| 1.57 | H | CH=CClCF$_3$ | H | Me | CF$_2$H | O |
| 1.58 | H | CH=CClCF$_3$ | F | Me | Me | O |
| 1.59 | H | CH$_2$C≡CH | H | Me | CF$_3$ | O |
| 1.60 | H | CH$_2$C≡CH | H | Me | CF$_2$H | O |
| 1.61 | H | CH$_2$C≡CH | F | Me | Me | O |
| 1.62 | H | CH$_2$C≡CH | H | CH$_2$OMe | CF$_3$ | O |
| 1.63 | H | CH$_2$C≡CSiMe$_3$ | H | Me | CF$_3$ | O |
| 1.64 | H | CH$_2$C≡CSiMe$_3$ | H | Me | CF$_2$H | O |
| 1.65 | H | CH$_2$C≡CSiMe$_3$ | F | Me | Me | O |
| 1.66 | H | C≡CCMe$_3$ | H | Me | CF$_3$ | O |
| 1.67 | H | C≡CCMe$_3$ | H | Me | CF$_2$H | O |
| 1.68 | H | C≡CCMe$_3$ | F | Me | Me | O |
| 1.69 | H | C≡CMe | H | Me | CF$_3$ | O |
| 1.70 | H | C≡CMe | H | Me | CF$_2$H | O |
| 1.71 | H | C≡CMe | F | Me | Me | O |
| 1.72 | COMe | C≡CH | H | Me | CF$_3$ | O |
| 1.73 | H | C≡CH | H | CF$_2$H | CF$_2$H | O |
| 1.74 | H | C≡CH | H | CF$_2$H | CF$_3$ | O |
| 1.75 | H | C≡CH | H | Me | CH$_2$F | O |
| 1.76 | H | C≡CSiMe$_3$ | H | Me | CH$_2$F | O |
| 1.77 | H | C≡C(cyclopropyl) | H | Me | CF$_3$ | O |
| 1.78 | H | C≡C(cyclopropyl) | H | Me | CHF$_2$ | O |
| 1.79 | H | SiMe$_3$ | H | Me | CH$_2$F | O |
| 1.80 | H | SiMe$_3$ | H | Me | CF$_3$ | O |
| 1.81 | H | SiMe$_3$ | H | Me | CHF$_2$ | O |
| 1.82 | H | C≡CF | H | Me | CF$_3$ | O |
| 1.83 | H | C≡CF | H | Me | CF$_2$H | O |
| 1.84 | H | C≡CF | F | Me | Me | O |
| 1.85 | H | C≡CCF$_2$Cl | H | Me | CF$_3$ | O |
| 1.86 | H | C≡CCF$_2$Cl | H | Me | CF$_2$H | O |
| 1.87 | H | C≡CCF$_2$Cl | F | Me | Me | O |
| 1.88 | H | C≡CCF$_2$H | H | Me | CF$_3$ | O |
| 1.89 | H | C≡CCF$_2$H | H | Me | CF$_2$H | O |
| 1.90 | H | C≡CCF$_2$H | F | Me | Me | O |
| 1.91 | H | C≡CCF$_2$Br | H | Me | CF$_3$ | O |
| 1.92 | H | C≡CCF$_2$Br | H | Me | CF$_2$H | O |
| 1.93 | H | C≡CCF$_2$Br | F | Me | Me | O |
| 1.94 | H | C≡CCH$_2$F | H | Me | CF$_3$ | O |
| 1.95 | H | C≡CCH$_2$F | H | Me | CF$_2$H | O |
| 1.96 | H | C≡CCH$_2$F | F | Me | Me | O |
| 1.97 | H | C≡CCH(Me)F | H | Me | CF$_3$ | O |
| 1.98 | H | C≡CCH(Me)F | H | Me | CF$_2$H | O |
| 1.99 | H | C≡CCH(Me)F | F | Me | Me | O |
| 1.100 | H | C≡CC(Me)$_2$F | H | Me | CF$_3$ | O |
| 1.101 | H | C≡CC(Me)$_2$F | H | Me | CF$_2$H | O |

TABLE 1-continued

| Compound No. | R¹ | R⁷ | R⁸ | R⁹ | R¹⁰ | X |
|---|---|---|---|---|---|---|
| 1.102 | H | C≡CC(Me)₂F | F | Me | Me | O |
| 1.103 | H | C≡CCH₂C(Me)₃ | H | Me | CF₃ | O |
| 1.104 | H | C≡CCH₂C(Me)₃ | H | Me | CF₂H | O |
| 1.105 | H | C≡CCH₂C(Me)₃ | F | Me | Me | O |
| 1.106 | H | C≡CCH(Me)₂ | H | Me | CF₃ | O |
| 1.107 | H | C≡CCH(Me)₂ | H | Me | CF₂H | O |
| 1.108 | H | C≡CCH(Me)₂ | F | Me | Me | O |
| 1.109 | H | C≡CCH₂CH(Me)₂ | H | Me | CF₃ | O |
| 1.110 | H | C≡CCH₂CH(Me)₂ | H | Me | CF₂H | O |
| 1.111 | H | C≡CCH₂CH(Me)₂ | F | Me | Me | O |
| 1.112 | H | CH₂C≡CCMe₃ | H | Me | CF₃ | O |
| 1.113 | H | CH₂C≡CCMe₃ | H | Me | CF₂H | O |
| 1.114 | H | CH₂C≡CCMe₃ | F | Me | Me | O |
| 1.115 | H | CF₂C≡CCMe₃ | H | Me | CF₃ | O |
| 1.116 | H | CF₂C≡CCMe₃ | H | Me | CF₂H | O |
| 1.117 | H | CF₂C≡CCMe₃ | F | Me | Me | O |
| 1.118 | H | CF₂C≡CMe | H | Me | CF₃ | O |
| 1.119 | H | CF₂C≡CMe | H | Me | CF₂H | O |
| 1.120 | H | CF₂C≡CMe | F | Me | Me | O |
| 1.121 | H | CF₂C≡CH | H | Me | CF₃ | O |
| 1.122 | H | CF₂C≡CH | H | Me | CF₂H | O |
| 1.123 | H | CF₂C≡CH | F | Me | Me | O |
| 1.124 | H | CMe₂C≡CH | H | Me | CF₃ | O |
| 1.125 | H | CMe₂C≡CH | H | Me | CF₂H | O |
| 1.126 | H | CMe₂C≡CH | F | Me | Me | O |
| 1.127 | H | CHFC≡CH | H | Me | CF₃ | O |
| 1.128 | H | CHFC≡CH | H | Me | CF₂H | O |
| 1.129 | H | CHFC≡CH | F | Me | Me | O |
| 1.130 | H | CHMeC≡CH | H | Me | CF₃ | O |
| 1.131 | H | CHMeC≡CH | H | Me | CF₂H | O |
| 1.132 | H | CHMeC≡CH | F | Me | Me | O |
| 1.133 | H | CH(CF₃)C≡CH | H | Me | CF₃ | O |
| 1.134 | H | CH(CF₃)C≡CH | H | Me | CF₂H | O |
| 1.135 | H | CH(CF₃)C≡CH | F | Me | Me | O |
| 1.136 | H | C≡C (1-F-cyclopentyl) | H | Me | CF₃ | O |
| 1.137 | H | C≡C (1-F-cyclopentyl) | H | Me | CHF₂ | O |
| 1.138 | H | C≡CCH₂OMe | H | Me | CF₃ | O |
| 1.139 | H | C≡CCH₂OMe | H | Me | CF₂H | O |
| 1.140 | H | C≡CCH₂OMe | F | Me | Me | O |
| 1.141 | H | C≡CCMe₂OMe | H | Me | CF₃ | O |
| 1.142 | H | C≡CCMe₂OMe | H | Me | CF₂H | O |
| 1.143 | H | C≡CCMe₂OMe | F | Me | Me | O |
| 1.144 | H | C≡CCMe₂OCOMe | H | Me | CF₃ | O |
| 1.145 | H | C≡CCMe₂OCOMe | H | Me | CF₂H | O |
| 1.146 | H | C≡CCF₂Me | H | Me | CF₃ | O |
| 1.147 | H | C≡CCF₂Me | H | Me | CF₂H | O |
| 1.148 | H | C≡CCF₂Me | F | Me | Me | O |
| 1.149 | H | C≡CC(Me)=CH₂ | H | Me | CF₃ | O |
| 1.150 | H | C≡CC(Me)=CH₂ | H | Me | CF₂H | O |
| 1.151 | H | CH=CFCl | H | Me | CF₃ | O |
| 1.152 | H | CH=CFCl | H | Me | CF₂H | O |
| 1.153 | H | CH=CFCl | F | Me | Me | O |
| 1.154 | H | CH=CFBr | H | Me | CF₃ | O |
| 1.155 | H | CH=CFBr | H | Me | CF₂H | O |
| 1.156 | H | CH=CFBr | F | Me | Me | O |
| 1.157 | H | CH=CHBr | H | Me | CF₃ | O |
| 1.158 | H | CH=CHBr | H | Me | CF₂H | O |
| 1.159 | H | CH=CHBr | F | Me | Me | O |
| 1.160 | H | CH=CHF | H | Me | CF₃ | O |
| 1.161 | H | CH=CHF | H | Me | CF₂H | O |
| 1.162 | H | CH=CHF | F | Me | Me | O |
| 1.163 | H | CMe=CHCF₃ | H | Me | CF₃ | O |
| 1.164 | H | CMe=CHCF₃ | H | Me | CF₂H | O |
| 1.165 | H | CMe=CHCF₃ | F | Me | Me | O |
| 1.166 | H | CH=CFCF₃ | H | Me | CF₃ | O |
| 1.167 | H | CH=CFCF₃ | H | Me | CF₂H | O |
| 1.168 | H | CH=CFCF₃ | F | Me | Me | O |
| 1.169 | H | CH=CBrCF₃ | H | Me | CF₃ | O |
| 1.170 | H | CH=CBrCF₃ | H | Me | CF₂H | O |
| 1.171 | H | CH=CBrCF₃ | F | Me | Me | O |
| 1.172 | H | CH=CHC₂F₅ | H | Me | CF₃ | O |
| 1.173 | H | CH=CHC₂F₅ | H | Me | CF₂H | O |
| 1.174 | H | CH=CHC₂F₅ | F | Me | Me | O |
| 1.175 | H | CH=CHCl | H | Me | CF₃ | O |
| 1.176 | H | CH=CHCl | H | Me | CF₂H | O |
| 1.177 | H | CH=CHCl | F | Me | Me | O |

TABLE 1-continued

| Compound No. | R¹ | R⁷ | R⁸ | R⁹ | R¹⁰ | X |
|---|---|---|---|---|---|---|
| 1.178 | H | CH=C(CF$_3$)$_2$ | H | Me | CF$_3$ | O |
| 1.179 | H | CH=C(CF$_3$)$_2$ | H | Me | CF$_2$H | O |
| 1.180 | H | CH=C(CF$_3$)$_2$ | F | Me | Me | O |
| 1.181 | H | CMe=CFCl | H | Me | CF$_3$ | O |
| 1.182 | H | CMe=CFCl | H | Me | CF$_2$H | O |
| 1.183 | H | CMe=CFCl | F | Me | Me | O |
| 1.184 | H | CMe=CFBr | H | Me | CF$_3$ | O |
| 1.185 | H | CMe=CFBr | H | Me | CF$_2$H | O |
| 1.186 | H | CMe=CFBr | F | Me | Me | O |
| 1.187 | H | CMe=CF$_2$ | H | Me | CF$_3$ | O |
| 1.188 | H | CMe=CF$_2$ | H | Me | CF$_2$H | O |
| 1.189 | H | CMe=CF$_2$ | F | Me | Me | O |
| 1.190 | H | CMe=CCl$_2$ | H | Me | CF$_3$ | O |
| 1.191 | H | CMe=CCl$_2$ | H | Me | CF$_2$H | O |
| 1.192 | H | CMe=CCl$_2$ | F | Me | Me | O |
| 1.193 | H | CMe=CBr$_2$ | H | Me | CF$_3$ | O |
| 1.194 | H | CMe=CBr$_2$ | H | Me | CF$_2$H | O |
| 1.195 | H | CMe=CBr$_2$ | F | Me | Me | O |
| 1.196 | H | CMe=CFCF$_3$ | H | Me | CF$_3$ | O |
| 1.197 | H | CMe=CFCF$_3$ | H | Me | CF$_2$H | O |
| 1.198 | H | CMe=CFCF$_3$ | F | Me | Me | O |
| 1.199 | H | CMe=CClCF$_3$ | H | Me | CF$_3$ | O |
| 1.200 | H | CMe=CClCF$_3$ | H | Me | CF$_2$H | O |
| 1.201 | H | CMe=CClCF$_3$ | F | Me | Me | O |
| 1.202 | H | CCF$_3$=CF$_2$ | H | Me | CF$_3$ | O |
| 1.203 | H | CCF$_3$=CF$_2$ | H | Me | CF$_2$H | O |
| 1.204 | H | CCF$_3$=CF$_2$ | F | Me | Me | O |
| 1.205 | H | CCF$_3$=CCl$_2$ | H | Me | CF$_3$ | O |
| 1.206 | H | CCF$_3$=CCl$_2$ | H | Me | CF$_2$H | O |
| 1.207 | H | CCF$_3$=CCl$_2$ | F | Me | Me | O |
| 1.208 | H | CCF$_3$=CBr$_2$ | H | Me | CF$_3$ | O |
| 1.209 | H | CCF$_3$=CBr$_2$ | H | Me | CF$_2$H | O |
| 1.210 | H | CCF$_3$=CBr$_2$ | F | Me | Me | O |
| 1.211 | H | CCF$_3$=CH$_2$ | H | Me | CF$_3$ | O |
| 1.212 | H | CCF$_3$=CH$_2$ | H | Me | CF$_2$H | O |
| 1.213 | H | CCF$_3$=CH$_2$ | F | Me | Me | O |
| 1.214 | H | CCF$_3$=CFBr | H | Me | CF$_3$ | O |
| 1.215 | H | CCF$_3$=CFBr | H | Me | CF$_2$H | O |
| 1.216 | H | CCF$_3$=CFBr | F | Me | Me | O |
| 1.217 | H | CCF$_3$=CHF | H | Me | CF$_3$ | O |
| 1.218 | H | CCF$_3$=CHF | H | Me | CF$_2$H | O |
| 1.219 | H | CCF$_3$=CHF | F | Me | Me | O |
| 1.220 | H | CCF$_3$=CFCl | H | Me | CF$_3$ | O |
| 1.221 | H | CCF$_3$=CFCl | H | Me | CF$_2$H | O |
| 1.222 | H | CCF$_3$=CFCl | F | Me | Me | O |
| 1.223 | H | CCF$_3$=CHCl | H | Me | CF$_3$ | O |
| 1.224 | H | CCF$_3$=CHCl | H | Me | CF$_2$H | O |
| 1.225 | H | CCF$_3$=CHCl | F | Me | Me | O |
| 1.226 | H | CH=CFCF$_2$Cl | H | Me | CF$_3$ | O |
| 1.227 | H | CH=CFCF$_2$Cl | H | Me | CF$_2$H | O |
| 1.228 | H | CH=CFCF$_2$Cl | F | Me | Me | O |
| 1.229 | H | CH=CClCF$_2$Cl | H | Me | CF$_3$ | O |
| 1.230 | H | CH=CClCF$_2$Cl | H | Me | CF$_2$H | O |
| 1.231 | H | CH=CClCF$_2$Cl | F | Me | Me | O |
| 1.232 | H | CH$_2$CF=CF$_2$ | H | Me | CF$_3$ | O |
| 1.233 | H | CH$_2$CF=CF$_2$ | H | Me | CF$_2$H | O |
| 1.234 | H | CH$_2$CF=CF$_2$ | F | Me | Me | O |
| 1.235 | H | CF=CFBr | H | Me | CF$_3$ | O |
| 1.236 | H | CF=CFBr | H | Me | CF$_2$H | O |
| 1.237 | H | CF=CFBr | F | Me | Me | O |
| 1.238 | H | CH$_2$CH=CF$_2$ | H | Me | CF$_3$ | O |
| 1.239 | H | CH$_2$CH=CF$_2$ | H | Me | CF$_2$H | O |
| 1.240 | H | CH$_2$CH=CF$_2$ | F | Me | Me | O |
| 1.241 | H | CH$_2$CH=CCl$_2$ | H | Me | CF$_3$ | O |
| 1.242 | H | CH$_2$CH=CCl$_2$ | H | Me | CF$_2$H | O |
| 1.243 | H | CH$_2$CH=CCl$_2$ | F | Me | Me | O |
| 1.244 | H | CH$_2$CH=CBr$_2$ | H | Me | CF$_3$ | O |
| 1.245 | H | CH$_2$CH=CBr$_2$ | H | Me | CF$_2$H | O |
| 1.246 | H | CH$_2$CH=CBr$_2$ | F | Me | Me | O |
| 1.247 | H | CCl=CF$_2$ | H | Me | CF$_3$ | O |
| 1.248 | H | CCl=CF$_2$ | H | Me | CF$_2$H | O |
| 1.249 | H | CCl=CF$_2$ | F | Me | Me | O |
| 1.250 | H | C≡CCMe$_2$OH | H | Me | CF$_3$ | O |
| 1.251 | H | C≡CCMe$_2$OH | H | Me | CF$_2$H | O |
| 1.252 | H | C≡CSi(Me$_2$)CMe$_3$ | H | Me | CF$_3$ | O |
| 1.253 | H | C≡CSi(Me$_2$)CMe$_3$ | H | Me | CF$_2$H | O |

TABLE 1-continued

| Compound No. | $R^1$ | $R^7$ | $R^8$ | $R^9$ | $R^{10}$ | X |
|---|---|---|---|---|---|---|
| 1.254 | H | C≡CCH$_2$SiMe$_3$ | H | Me | CF$_3$ | O |
| 1.255 | H | C≡CCH$_2$SiMe$_3$ | H | Me | CF$_2$H | O |
| 1.256 | H | C≡CCH$_2$SiMe$_3$ | F | Me | Me | O |
| 1.257 | H | C≡CCMe$_3$ | H | CF$_2$H | CF$_3$ | O |
| 1.258 | H | C≡CCH$_2$CF$_3$ | H | Me | CF$_3$ | O |
| 1.259 | H | C≡CCH$_2$CF$_3$ | H | Me | CF$_2$H | O |
| 1.260 | H | C≡CCH$_2$CF$_3$ | F | Me | Me | O |
| 1.261 | H | C≡CCMe$_3$ | H | CF$_2$H | CF$_2$H | O |
| 1.262 | H | C≡CCH$_2$CH$_3$ | H | Me | CF$_3$ | O |
| 1.263 | H | C≡CCH$_2$CH$_3$ | H | Me | CF$_2$H | O |
| 1.264 | H | C≡CCH$_2$CH$_3$ | F | Me | Me | O |
| 1.265 | H | C≡CCF=CF$_2$ | H | Me | CF$_3$ | O |
| 1.266 | H | C≡CCF=CF$_2$ | H | Me | CF$_2$H | O |
| 1.267 | H | C≡CCHFCl | H | Me | CF$_3$ | O |
| 1.268 | H | C≡CCHFCl | H | Me | CF$_2$H | O |
| 1.269 | H | C≡CCHFCl | F | Me | Me | O |
| 1.270 | H | CH=CFC$_2$F$_5$ | H | Me | CF$_3$ | O |
| 1.271 | H | CH=CFC$_2$F$_5$ | H | Me | CF$_2$H | O |
| 1.272 | H | CH=CFC$_2$F$_5$ | F | Me | Me | O |
| 1.273 | H | C≡CCF$_2$CH$_2$CH$_3$ | H | Me | CF$_3$ | O |
| 1.274 | H | C≡CCF$_2$CH$_2$CH$_3$ | H | Me | CF$_2$H | O |
| 1.275 | H | C≡CCF$_2$CH$_2$CH$_3$ | F | Me | Me | O |
| 1.276 | H | C≡CCHFCH$_2$CH$_3$ | H | Me | CF$_3$ | O |
| 1.277 | H | C≡CCHFCH$_2$CH$_3$ | H | Me | CF$_2$H | O |
| 1.278 | H | C≡CCHFCH$_2$CH$_3$ | F | Me | Me | O |
| 1.279 | H | C≡CCF(CF$_3$)$_2$ | H | Me | CF$_3$ | O |
| 1.280 | H | C≡CCF(CF$_3$)$_2$ | H | Me | CF$_2$H | O |
| 1.281 | H | C≡CCF(CF$_3$)$_2$ | F | Me | Me | O |
| 1.282 | H | CH=CClC$_2$F$_5$ | H | Me | CF$_3$ | O |
| 1.283 | H | CH=CClC$_2$F$_5$ | H | Me | CF$_2$H | O |
| 1.284 | H | CH=CClC$_2$F$_5$ | F | Me | Me | O |
| 1.285 | H | C≡CC$_2$F$_5$ | H | Me | CF$_3$ | O |
| 1.286 | H | C≡CC$_2$F$_5$ | H | Me | CF$_2$H | O |
| 1.287 | H | C≡CC$_2$F$_5$ | F | Me | Me | O |

Table 1 provides 287 compounds of formula (Ia):

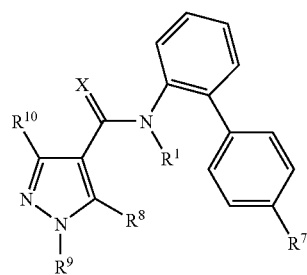

(Ia)

wherein $R^1$, $R^7$, $R^8$, $R^9$, $R^{10}$ and X are as defined in Table 1.

Table 1 provides 287 compounds of formula (IaA):

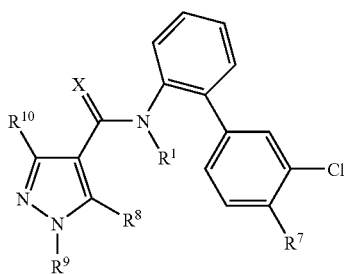

(IaA)

wherein $R^1$, $R^7$, $R^8$, $R^9$, $R^{10}$ and X are as defined in Table 1.

Table 1 provides 287 compounds of formula (IaB) wherein $R^1$, $R^7$, $R^8$, $R^9$, $R^{10}$ and X are as defined in Table 1.

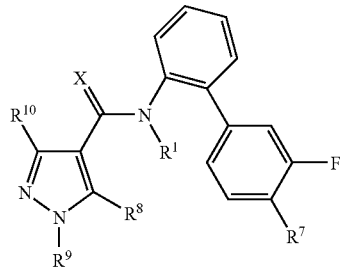

(IaB)

Table 1 provides 287 compounds of formula (IaC) wherein $R^1$, $R^7$, $R^8$, $R^9$, $R^{10}$ and X are as defined in Table 1.

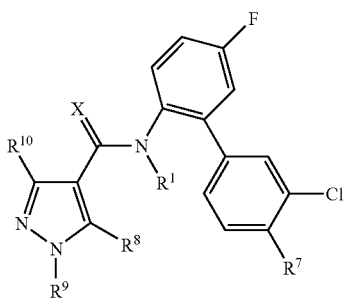

(IaC)

Table 1 provides 287 compounds of formula (IaD) wherein $R^1$, $R^7$, $R^8$, $R^9$, $R^{10}$ and X are as defined in Table 1.

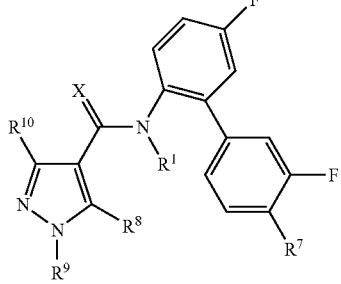
(IaD)

Table 1 provides 287 compounds of formula (IaE) wherein $R^1$, $R^7$, $R^8$, $R^9$, $R^{10}$ and X are as defined in Table 1.

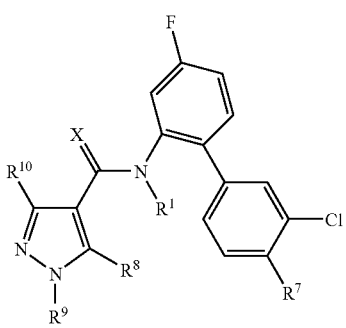
(IaE)

Table 1 provides 287 compounds of formula (IaF) wherein $R^1$, $R^7$, $R^8$, $R^9$, $R^{10}$ and X are as defined in Table 1.

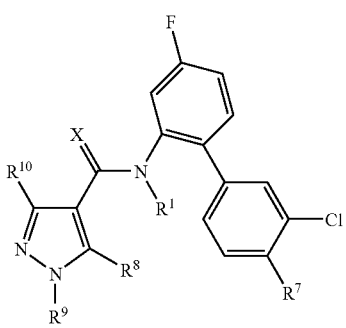
(IaF)

Table 1 provides 287 compounds of formula (IaG) wherein $R^1$, $R^7$, $R^8$, $R^9$, $R^{10}$ and X are as defined as Table 1.

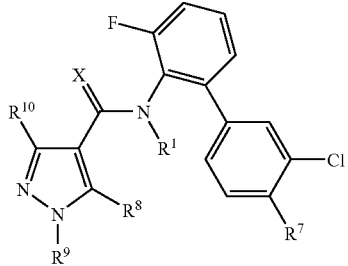
(IaG)

Table 1 provides 287 compounds of fornula (IaH) wherein $R^1$, $R^7$, $R^8$, $R^9$, $R^{10}$ and X are as defined in Table 1.

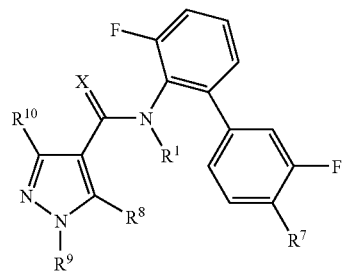
(IaH)

Table 1 provides 287 compounds of formula (IaI) wherein $R^1$, $R^7$, $R^8$, $R^9$, $R^{10}$ and X are as defined in Table 1.

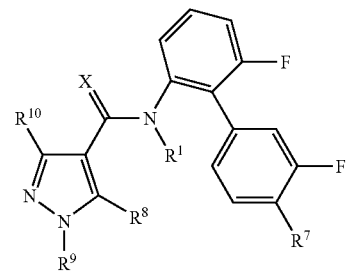
(IaI)

Table 1 provides 287 compounds of formula (IaJ) wherein $R^1$, $R^7$, $R^8$, $R^9$, $R^{10}$ and X are as defined in Table 1.

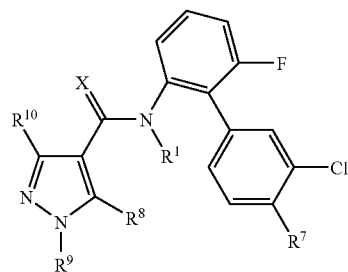
(IaJ)

TABLE 2

| Compound No. | R¹ | R⁷ | R⁸ | R⁹ | R¹⁰ | X |
|---|---|---|---|---|---|---|
| 2.01 | H | C≡CH | H | Me | CF₃ | O |
| 2.02 | H | C≡CH | H | Me | CF₃ | S |
| 2.03 | H | C≡CH | H | Me | CF₂H | O |
| 2.04 | propargyl | C≡CH | H | Me | CF₃ | O |
| 2.05 | H | C≡CH | F | Me | Me | O |
| 2.06 | H | C≡CH | H | CH₂OMe | CF₃ | O |
| 2.07 | allenyl | C≡CH | H | Me | CF₃ | O |
| 2.08 | H | C≡CSiMe₃ | H | Me | CF₃ | O |
| 2.09 | H | C≡CSiMe₃ | H | Me | CF₃ | S |
| 2.10 | H | C≡CSiMe₃ | H | Me | CF₂H | O |
| 2.11 | H | C≡CSiMe₃ | F | Me | Me | O |
| 2.12 | H | C≡CCl | H | Me | CF₃ | O |
| 2.13 | H | C≡CCl | H | Me | CF₂H | O |
| 2.14 | H | C≡CCl | F | Me | Me | O |
| 2.15 | H | C≡CBr | H | Me | CF₃ | O |
| 2.16 | H | C≡CBr | H | Me | CF₂H | O |
| 2.17 | H | C≡CBr | F | Me | Me | O |
| 2.18 | H | C≡CCF₃ | H | Me | CF₃ | O |
| 2.19 | H | C≡CCF₃ | H | Me | CF₂H | O |
| 2.20 | H | C≡CCF₃ | F | Me | Me | O |
| 2.21 | allenyl | C≡CCF₃ | H | Me | CF₃ | O |
| 2.22 | H | CH=CH₂ | H | Me | CF₃ | O |
| 2.23 | H | CH=CH₂ | H | Me | CF₃ | S |
| 2.24 | H | CH=CH₂ | H | Me | CF₂H | O |
| 2.25 | propargyl | CH=CH₂ | H | Me | CF₃ | O |
| 2.26 | H | CH=CH₂ | F | Me | Me | O |
| 2.27 | H | CH=CH₂ | H | CH₂OMe | CF₃ | O |
| 2.28 | allenyl | CH=CH₂ | H | Me | CF₃ | O |
| 2.29 | H | CH=CF₂ | H | Me | CF₃ | O |
| 2.30 | H | CH=CF₂ | H | Me | CF₂H | O |
| 2.31 | H | CH=CF₂ | F | Me | Me | O |
| 2.32 | H | CH=CCl₂ | H | Me | CF₃ | O |
| 2.33 | H | CH=CCl₂ | H | Me | CF₂H | O |
| 2.34 | H | CH=CCl₂ | F | Me | Me | O |
| 2.35 | H | CH=CBr₂ | H | Me | CF₃ | O |
| 2.36 | H | CH=CBr₂ | H | Me | CF₂H | O |
| 2.37 | H | CH=CBr₂ | F | Me | Me | O |
| 2.38 | H | CF=CF₂ | H | Me | CF₃ | O |
| 2.39 | H | CF=CF₂ | H | Me | CF₂H | O |
| 2.40 | H | CF=CF₂ | F | Me | Me | O |
| 2.41 | H | CCl=CH₂ | H | Me | CF₃ | O |
| 2.42 | H | CCl=CH₂ | H | Me | CF₂H | O |
| 2.43 | H | CCl=CH₂ | F | Me | Me | O |
| 2.44 | H | CBr=CH₂ | H | Me | CF₃ | O |
| 2.45 | H | CBr=CH₂ | H | Me | CF₂H | O |
| 2.46 | H | CBr=CH₂ | F | Me | Me | O |
| 2.47 | H | CF=CHF | H | Me | CF₃ | O |
| 2.48 | H | CF=CHF | H | Me | CF₂H | O |
| 2.49 | H | CF=CHF | F | Me | Me | O |
| 2.50 | H | CH=CHSiMe₃ | H | Me | CF₃ | O |
| 2.51 | H | CH=CHSiMe₃ | H | Me | CF₂H | O |
| 2.52 | H | CH=CHSiMe₃ | F | Me | Me | O |
| 2.53 | H | CH=CHCF₃ | H | Me | CF₃ | O |
| 2.54 | H | CH=CHCF₃ | H | Me | CF₂H | O |
| 2.55 | H | CH=CHCF₃ | F | Me | Me | O |
| 2.56 | H | CH=CClCF₃ | H | Me | CF₃ | O |
| 2.57 | H | CH=CClCF₃ | H | Me | CF₂H | O |
| 2.58 | H | CH=CClCF₃ | F | Me | Me | O |
| 2.59 | H | CH₂C≡CH | H | Me | CF₃ | O |
| 2.60 | H | CH₂C≡CH | H | Me | CF₂H | O |
| 2.61 | H | CH₂C≡CH | F | Me | Me | O |
| 2.62 | H | CH₂C≡CH | H | CH₂OMe | CF₃ | O |
| 2.63 | H | CH₂C≡CSiMe₃ | H | Me | CF₃ | O |
| 2.64 | H | CH₂C≡CSiMe₃ | H | Me | CF₂H | O |
| 2.65 | H | CH₂C≡CSiMe₃ | F | Me | Me | O |
| 2.66 | H | C≡CCMe₃ | H | Me | CF₃ | O |
| 2.67 | H | C≡CCMe₃ | H | Me | CF₂H | O |
| 2.68 | H | C≡CCMe₃ | F | Me | Me | O |
| 2.69 | H | C≡CMe | H | Me | CF₃ | O |
| 2.70 | H | C≡CMe | H | Me | CF₂H | O |
| 2.71 | H | C≡CMe | F | Me | Me | O |
| 2.72 | COMe | C≡CH | H | Me | CF₃ | O |
| 2.73 | H | C≡CH | H | CF₂H | CF₂H | O |
| 2.74 | H | C≡CH | H | CF₂H | CF₃ | O |
| 2.75 | H | C≡CH | H | Me | CH₂F | O |
| 2.76 | H | C≡CSiMe₃ | H | Me | CH₂F | O |

TABLE 2-continued

| Compound No. | R¹ | R⁷ | R⁸ | R⁹ | R¹⁰ | X |
|---|---|---|---|---|---|---|
| 2.77 | H | C≡C(cyclopropyl) | H | Me | $CF_3$ | O |
| 2.78 | H | C≡C(cyclopropyl) | H | Me | $CHF_2$ | O |
| 2.79 | H | $SiMe_3$ | H | Me | $CH_2F$ | O |
| 2.80 | H | $SiMe_3$ | H | Me | $CF_3$ | O |
| 2.81 | H | $SiMe_3$ | H | Me | $CHF_2$ | O |
| 2.82 | H | C≡CF | H | Me | $CF_3$ | O |
| 2.83 | H | C≡CF | H | Me | $CF_2H$ | O |
| 2.84 | H | C≡CF | F | Me | Me | O |
| 2.85 | H | C≡C$CF_2$Cl | H | Me | $CF_3$ | O |
| 2.86 | H | C≡C$CF_2$Cl | H | Me | $CF_2H$ | O |
| 2.87 | H | C≡C$CF_2$Cl | F | Me | Me | O |
| 2.88 | H | C≡C$CF_2$H | H | Me | $CF_3$ | O |
| 2.89 | H | C≡C$CF_2$H | H | Me | $CF_2H$ | O |
| 2.90 | H | C≡C$CF_2$H | F | Me | Me | O |
| 2.91 | H | C≡C$CF_2$Br | H | Me | $CF_3$ | O |
| 2.92 | H | C≡C$CF_2$Br | H | Me | $CF_2H$ | O |
| 2.93 | H | C≡C$CF_2$Br | F | Me | Me | O |
| 2.94 | H | C≡C$CH_2F$ | H | Me | $CF_3$ | O |
| 2.95 | H | C≡C$CH_2F$ | H | Me | $CF_2H$ | O |
| 2.96 | H | C≡C$CH_2F$ | F | Me | Me | O |
| 2.97 | H | C≡CCH(Me)F | H | Me | $CF_3$ | O |
| 2.98 | H | C≡CCH(Me)F | H | Me | $CF_2H$ | O |
| 2.99 | H | C≡CCH(Me)F | F | Me | Me | O |
| 2.100 | H | C≡CC(Me)$_2$F | H | Me | $CF_3$ | O |
| 2.101 | H | C≡CC(Me)$_2$F | H | Me | $CF_2H$ | O |
| 2.102 | H | C≡CC(Me)$_2$F | F | Me | Me | O |
| 2.103 | H | C≡C$CH_2$C(Me)$_3$ | H | Me | $CF_3$ | O |
| 2.104 | H | C≡C$CH_2$C(Me)$_3$ | H | Me | $CF_2H$ | O |
| 2.105 | H | C≡C$CH_2$C(Me)$_3$ | F | Me | Me | O |
| 2.106 | H | C≡CCH(Me)$_2$ | H | Me | $CF_2H$ | O |
| 2.107 | H | C≡CCH(Me)$_2$ | H | Me | $CF_2H$ | O |
| 2.108 | H | C≡CCH(Me)$_2$ | F | Me | Me | O |
| 2.109 | H | C≡C$CH_2$CH(Me)$_2$ | H | Me | $CF_2H$ | O |
| 2.110 | H | C≡C$CH_2$CH(Me)$_2$ | H | Me | $CF_2H$ | O |
| 2.111 | H | C≡C$CH_2$CH(Me)$_2$ | F | Me | Me | O |
| 2.112 | H | $CH_2$C≡C$CMe_3$ | H | Me | $CF_3$ | O |
| 2.113 | H | $CH_2$C≡C$CMe_3$ | H | Me | $CF_2H$ | O |
| 2.114 | H | $CH_2$C≡C$CMe_3$ | F | Me | Me | O |
| 2.115 | H | $CF_2$C≡C$CMe_3$ | H | Me | $CF_3$ | O |
| 2.116 | H | $CF_2$C≡C$CMe_3$ | H | Me | $CF_2H$ | O |
| 2.117 | H | $CF_2$C≡C$CMe_3$ | F | Me | Me | O |
| 2.118 | H | $CF_2$C≡CMe | H | Me | $CF_3$ | O |
| 2.119 | H | $CF_2$C≡CMe | H | Me | $CF_2H$ | O |
| 2.120 | H | $CF_2$C≡CCMe | F | Me | Me | O |
| 2.121 | H | $CF_2$C≡CH | H | Me | $CF_3$ | O |
| 2.122 | H | $CF_2$C≡CH | H | Me | $CF_2H$ | O |
| 2.123 | H | $CF_2$C≡CH | F | Me | Me | O |
| 2.124 | H | $CMe_2$C≡CH | H | Me | $CF_3$ | O |
| 2.125 | H | $CMe_2$C≡CH | H | Me | $CF_2H$ | O |
| 2.126 | H | $CMe_2$C≡CH | F | Me | Me | O |
| 2.127 | H | CHFC≡CH | H | Me | $CF_3$ | O |
| 2.128 | H | CHFC≡CH | H | Me | $CF_2H$ | O |
| 2.129 | H | CHFC≡CH | F | Me | Me | O |
| 2.130 | H | CHMeC≡CH | H | Me | $CF_3$ | O |
| 2.131 | H | CHMeC≡CH | H | Me | $CF_2H$ | O |
| 2.132 | H | CHMeC≡CH | F | Me | Me | O |
| 2.133 | H | CH($CF_3$)C≡CH | H | Me | $CF_3$ | O |
| 2.134 | H | CH($CF_3$)C≡CH | H | Me | $CF_2H$ | O |
| 2.135 | H | CH($CF_3$)C≡CH | F | Me | Me | O |
| 2.136 | H | C≡C(1-F-cyclopentyl) | H | Me | $CF_3$ | O |
| 2.137 | H | C≡C(1-F-cyclopentyl) | H | Me | $CHF_2$ | O |
| 2.138 | H | C≡C$CH_2$OMe | H | Me | $CF_3$ | O |
| 2.139 | H | C≡C$CH_2$OMe | H | Me | $CF_2H$ | O |
| 2.140 | H | C≡C$CH_2$OMe | F | Me | Me | O |
| 2.141 | H | C≡C$CMe_2$OMe | H | Me | $CF_3$ | O |
| 2.142 | H | C≡C$CMe_2$OMe | H | Me | $CF_2H$ | O |
| 2.143 | H | C≡C$CMe_2$OMe | F | Me | Me | O |
| 2.144 | H | C≡C$CMe_2$OCOMe | H | Me | $CF_3$ | O |
| 2.145 | H | C≡C$CMe_2$OCOMe | H | Me | $CF_2H$ | O |
| 2.146 | H | C≡C$CF_2$Me | H | Me | $CF_3$ | O |
| 2.147 | H | C≡C$CF_2$Me | H | Me | $CF_2H$ | O |
| 2.148 | H | C≡C$CF_2$Me | F | Me | Me | O |
| 2.149 | H | C≡CC(Me)=$CH_2$ | H | Me | $CF_3$ | O |
| 2.150 | H | C≡CC(Me)=$CH_2$ | H | Me | $CF_2H$ | O |
| 2.151 | H | CH=CFCl | H | Me | $CF_3$ | O |
| 2.152 | H | CH=CFCl | H | Me | $CF_2H$ | O |

TABLE 2-continued

| Compound No. | R¹ | R⁷ | R⁸ | R⁹ | R¹⁰ | X |
|---|---|---|---|---|---|---|
| 2.153 | H | CH=CFCl | F | Me | Me | O |
| 2.154 | H | CH=CFBr | H | Me | CF$_3$ | O |
| 2.155 | H | CH=CFBr | H | Me | CF$_2$H | O |
| 2.156 | H | CH=CFBr | F | Me | Me | O |
| 2.157 | H | CH=CHBr | H | Me | CF$_3$ | O |
| 2.158 | H | CH=CHBr | H | Me | CF$_2$H | O |
| 2.159 | H | CH=CHBr | F | Me | Me | O |
| 2.160 | H | CH=CHF | H | Me | CF$_3$ | O |
| 2.161 | H | CH=CHF | H | Me | CF$_2$H | O |
| 2.162 | H | CH=CHF | F | Me | Me | O |
| 2.163 | H | CMe=CHCF$_3$ | H | Me | CF$_3$ | O |
| 2.164 | H | CMe=CHCF$_3$ | H | Me | CF$_2$H | O |
| 2.165 | H | CMe=CHCF$_3$ | F | Me | Me | O |
| 2.166 | H | CH=CFCF$_3$ | H | Me | CF$_3$ | O |
| 2.167 | H | CH=CFCF$_3$ | H | Me | CF$_2$H | O |
| 2.168 | H | CH=CFCF$_3$ | F | Me | Me | O |
| 2.169 | H | CH=CBrCF$_3$ | H | Me | CF$_3$ | O |
| 2.170 | H | CH=CBrCF$_3$ | H | Me | CF$_2$H | O |
| 2.171 | H | CH=CBrCF$_3$ | F | Me | Me | O |
| 2.172 | H | CH=CHC$_2$F$_5$ | H | Me | CF$_3$ | O |
| 2.173 | H | CH=CHC$_2$F$_5$ | H | Me | CF$_2$H | O |
| 2.174 | H | CH=CHC$_2$F$_5$ | F | Me | Me | O |
| 2.175 | H | CH=CHCl | H | Me | CF$_3$ | O |
| 2.176 | H | CH=CHCl | H | Me | CF$_2$H | O |
| 2.177 | H | CH=CHCl | F | Me | Me | O |
| 2.178 | H | CH=C(CF$_3$)$_2$ | H | Me | CF$_3$ | O |
| 2.179 | H | CH=C(CF$_3$)$_2$ | H | Me | CF$_2$H | O |
| 2.180 | H | CH=C(CF$_3$)$_2$ | F | Me | Me | O |
| 2.181 | H | CMe=CFCl | H | Me | CF$_3$ | O |
| 2.182 | H | CMe=CFCl | H | Me | CF$_2$H | O |
| 2.183 | H | CMe=CFCl | F | Me | Me | O |
| 2.184 | H | CMe=CFBr | H | Me | CF$_3$ | O |
| 2.185 | H | CMe=CFBr | H | Me | CF$_2$H | O |
| 2.186 | H | CMe=CFBr | F | Me | Me | O |
| 2.187 | H | CMe=CF$_2$ | H | Me | CF$_3$ | O |
| 2.188 | H | CMe=CF$_2$ | H | Me | CF$_2$H | O |
| 2.189 | H | CMe=CF$_2$ | F | Me | Me | O |
| 2.190 | H | CMe=CCl$_2$ | H | Me | CF$_3$ | O |
| 2.191 | H | CMe=CCl$_2$ | H | Me | CF$_2$H | O |
| 2.192 | H | CMe=CCl$_2$ | F | Me | Me | O |
| 2.193 | H | CMe=CBr$_2$ | H | Me | CF$_3$ | O |
| 2.194 | H | CMe=CBr$_2$ | H | Me | CF$_2$H | O |
| 2.195 | H | CMe=CBr$_2$ | F | Me | Me | O |
| 2.196 | H | CMe=CFCF$_3$ | H | Me | CF$_3$ | O |
| 2.197 | H | CMe=CFCF$_3$ | H | Me | CF$_2$H | O |
| 2.198 | H | CMe=CFCF$_3$ | F | Me | Me | O |
| 2.199 | H | CMe=CClCF$_3$ | H | Me | CF$_3$ | O |
| 2.200 | H | CMe=CClCF$_3$ | H | Me | CF$_2$H | O |
| 2.201 | H | CMe=CClCF$_3$ | F | Me | Me | O |
| 2.202 | H | CCF$_3$=CF$_2$ | H | Me | CF$_3$ | O |
| 2.203 | H | CCF$_3$=CF$_2$ | H | Me | CF$_2$H | O |
| 2.204 | H | CCF$_3$=CF$_2$ | F | Me | Me | O |
| 2.205 | H | CCF$_3$=CCl$_2$ | H | Me | CF$_3$ | O |
| 2.206 | H | CCF$_3$=CCl$_2$ | H | Me | CF$_2$H | O |
| 2.207 | H | CCF$_3$=CCl$_2$ | F | Me | Me | O |
| 2.208 | H | CCF$_3$=CBr$_2$ | H | Me | CF$_3$ | O |
| 2.209 | H | CCF$_3$=CBr$_2$ | H | Me | CF$_2$H | O |
| 2.210 | H | CCF$_3$=CBr$_2$ | F | Me | Me | O |
| 2.211 | H | CCF$_3$=CH$_2$ | H | Me | CF$_3$ | O |
| 2.212 | H | CCF$_3$=CH$_2$ | H | Me | CF$_2$H | O |
| 2.213 | H | CCF$_3$=CH$_2$ | F | Me | Me | O |
| 2.214 | H | CCF$_3$=CFBr | H | Me | CF$_3$ | O |
| 2.215 | H | CCF$_3$=CFBr | H | Me | CF$_2$H | O |
| 2.216 | H | CCF$_3$=CFBr | F | Me | Me | O |
| 2.217 | H | CCF$_3$=CHF | H | Me | CF$_3$ | O |
| 2.218 | H | CCF$_3$=CHF | H | Me | CF$_2$H | O |
| 2.219 | H | CCF$_3$=CHF | F | Me | Me | O |
| 2.220 | H | CCF$_3$=CFCl | H | Me | CF$_3$ | O |
| 2.221 | H | CCF$_3$=CFCl | H | Me | CF$_2$H | O |
| 2.222 | H | CCF$_3$=CFCl | F | Me | Me | O |
| 2.223 | H | CCF$_3$=CHCl | H | Me | CF$_3$ | O |
| 2.224 | H | CCF$_3$=CHCl | H | Me | CF$_2$H | O |
| 2.225 | H | CCF$_3$=CHCl | F | Me | Me | O |
| 2.226 | H | CH=CFCF$_2$Cl | H | Me | CF$_3$ | O |
| 2.227 | H | CH=CFCF$_2$Cl | H | Me | CF$_2$H | O |
| 2.228 | H | CH=CFCF$_2$Cl | F | Me | Me | O |

TABLE 2-continued

| Compound No. | R¹ | R⁷ | R⁸ | R⁹ | R¹⁰ | X |
|---|---|---|---|---|---|---|
| 2.229 | H | CH=CClCF₂Cl | H | Me | CF₃ | O |
| 2.230 | H | CH=CClCF₂Cl | H | Me | CF₂H | O |
| 2.231 | H | CH=CClCF₂Cl | F | Me | Me | O |
| 2.232 | H | CH₂CF=CF₂ | H | Me | CF₃ | O |
| 2.233 | H | CH₂CF=CF₂ | H | Me | CF₂H | O |
| 2.234 | H | CH₂CF=CF₂ | F | Me | Me | O |
| 2.235 | H | CF=CFBr | H | Me | CF₃ | O |
| 2.236 | H | CF=CFBr | H | Me | CF₂H | O |
| 2.237 | H | CF=CFBr | F | Me | Me | O |
| 2.238 | H | CH₂CH=CF₂ | H | Me | CF₃ | O |
| 2.239 | H | CH₂CH=CF₂ | H | Me | CF₂H | O |
| 2.240 | H | CH₂CH=CF₂ | F | Me | Me | O |
| 2.241 | H | CH₂CH=CCl₂ | H | Me | CF₃ | O |
| 2.242 | H | CH₂CH=CCl₂ | H | Me | CF₂H | O |
| 2.243 | H | CH₂CH=CCl₂ | F | Me | Me | O |
| 2.244 | H | CH₂CH=CBr₂ | H | Me | CF₃ | O |
| 2.245 | H | CH₂CH=CBr₂ | H | Me | CF₂H | O |
| 2.246 | H | CH₂CH=CBr₂ | F | Me | Me | O |
| 2.247 | H | CCl=CF₂ | H | Me | CF₃ | O |
| 2.248 | H | CCl=CF₂ | H | Me | CF₂H | O |
| 2.249 | H | CCl=CF₂ | F | Me | Me | O |

Table 2 provides 249 compounds of formula (Ib) wherein $R^1$, $R^7$, $R^8$, $R^9$, $R^{10}$ and X are as defined in Table 2.

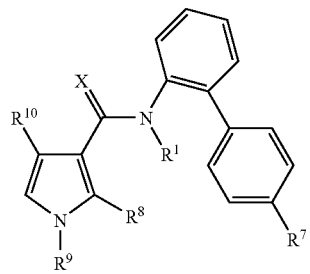

(Ib)

TABLE 3

| Compound No. | R¹ | R⁷ | R⁹ | R¹⁰ | X |
|---|---|---|---|---|---|
| 3.01 | H | C≡CH | Me | CF₃ | O |
| 3.02 | H | C≡CH | Me | CF₃ | S |
| 3.03 | H | C≡CH | Me | CF₂H | O |
| 3.04 | propargyl | C≡CH | Me | CF₃ | O |
| 3.05 | H | C≡CH | Me | Me | O |
| 3.06 | H | C≡CH | CH₂OMe | CF₃ | O |
| 3.07 | allenyl | C≡CH | Me | CF₃ | O |
| 3.08 | H | C≡CSiMe₃ | Me | CF₃ | O |
| 3.09 | H | C≡CSiMe₃ | Me | CF₃ | S |
| 3.10 | H | C≡CSiMe₃ | Me | CF₂H | O |
| 3.11 | H | C≡CSiMe₃ | Me | Me | O |
| 3.12 | H | C≡CCl | Me | CF₃ | O |
| 3.13 | H | C≡CCl | Me | CF₂H | O |
| 3.14 | H | C≡CCl | Me | Me | O |
| 3.15 | H | C≡CBr | Me | CF₃ | O |
| 3.16 | H | C≡CBr | Me | CF₂H | O |
| 3.17 | H | C≡CBr | Me | Me | O |
| 3.18 | H | C≡CCF₃ | Me | CF₃ | O |
| 3.19 | H | C≡CCF₃ | Me | CF₂H | O |
| 3.20 | H | C≡CCF₃ | Me | Me | O |
| 3.21 | allenyl | C≡CCF₃ | Me | CF₃ | O |
| 3.22 | H | CH=CH₂ | Me | CF₃ | O |
| 3.23 | H | CH=CH₂ | Me | CF₃ | S |
| 3.24 | H | CH=CH₂ | Me | CF₂H | O |
| 3.25 | propargyl | CH=CH₂ | Me | CF₃ | O |
| 3.26 | H | CH=CH₂ | Me | Me | O |
| 3.27 | H | CH=CH₂ | CH₂OMe | CF₃ | O |
| 3.28 | allenyl | CH=CH₂ | Me | CF₃ | O |
| 3.29 | H | CH=CF₂ | Me | CF₃ | O |
| 3.30 | H | CH=CF₂ | Me | CF₂H | O |
| 3.31 | H | CH=CF₂ | Me | Me | O |
| 3.32 | H | CH=CCl₂ | Me | CF₃ | O |
| 3.33 | H | CH=CCl₂ | Me | CF₂H | O |
| 3.34 | H | CH=CCl₂ | Me | Me | O |
| 3.35 | H | CH=CBr₂ | Me | CF₃ | O |
| 3.36 | H | CH=CBr₂ | Me | CF₂H | O |
| 3.37 | H | CH=CBr₂ | Me | Me | O |
| 3.38 | H | CF=CF₂ | Me | CF₃ | O |
| 3.39 | H | CF=CF₂ | Me | CF₂H | O |
| 3.40 | H | CF=CF₂ | Me | Me | O |
| 3.41 | H | CCl=CH₂ | Me | CF₃ | O |
| 3.42 | H | CCl=CH₂ | Me | CF₂H | O |
| 3.43 | H | CCl=CH₂ | Me | Me | O |
| 3.44 | H | CBr=CH₂ | Me | CF₃ | O |
| 3.45 | H | CBr=CH₂ | Me | CF₂H | O |
| 3.46 | H | CBr=CH₂ | Me | Me | O |
| 3.47 | H | CF=CHF | Me | CF₃ | O |
| 3.48 | H | CF=CHF | Me | CF₂H | O |
| 3.49 | H | CF=CHF | Me | Me | O |
| 3.50 | H | CH=CHSiMe₃ | Me | CF₃ | O |
| 3.51 | H | CH=CHSiMe₃ | Me | CF₂H | O |
| 3.52 | H | CH=CHSiMe₃ | Me | Me | O |
| 3.53 | H | CH=CHCF₃ | Me | CF₃ | O |
| 3.54 | H | CH=CHCF₃ | Me | CF₂H | O |
| 3.55 | H | CH=CHCF₃ | Me | Me | O |
| 3.56 | H | CH=CClCF₃ | Me | CF₃ | O |
| 3.57 | H | CH=CClCF₃ | Me | CF₂H | O |
| 3.58 | H | CH=CClCF₃ | Me | Me | O |
| 3.59 | H | CH₂C≡CH | Me | CF₃ | O |
| 3.60 | H | CH₂C≡CH | Me | CF₂H | O |
| 3.61 | H | CH₂C≡CH | Me | Me | O |
| 3.62 | H | CH₂C≡CH | CH₂OMe | CF₃ | O |
| 3.63 | H | CH₂C≡CSiMe₃ | Me | CF₃ | O |
| 3.64 | H | CH₂C≡CSiMe₃ | Me | CF₂H | O |
| 3.65 | H | CH₂C≡CSiMe₃ | Me | Me | O |
| 3.66 | H | C≡CCMe₃ | Me | CF₃ | O |
| 3.67 | H | C≡CCMe₃ | Me | CF₂H | O |
| 3.68 | H | C≡CCMe₃ | Me | Me | O |
| 3.69 | H | C≡CMe | Me | CF₃ | O |
| 3.70 | H | C≡CMe | Me | CF₂H | O |

TABLE 3-continued

| Compound No. | R¹ | R⁷ | R⁹ | R¹⁰ | X |
|---|---|---|---|---|---|
| 3.71 | H | C≡CMe | Me | Me | O |
| 3.72 | COMe | C≡CH | Me | CF$_3$ | O |
| 3.73 | H | C≡CH | CF$_2$H | CF$_2$H | O |
| 3.74 | H | C≡CH | CF$_2$H | CF$_3$ | O |
| 3.75 | H | C≡CH | Me | CH$_2$F | O |
| 3.76 | H | C≡CSiMe$_3$ | Me | CH$_2$F | O |
| 3.77 | H | C≡C(cyclopropyl) | Me | CF$_3$ | O |
| 3.78 | H | C≡C(cyclopropyl) | Me | CHF$_2$ | O |
| 3.79 | H | SiMe$_3$ | Me | CH$_2$F | O |
| 3.80 | H | SiMe$_3$ | Me | CF$_3$ | O |
| 3.81 | H | SiMe$_3$ | Me | CHF$_2$ | O |
| 3.82 | H | C≡CF | Me | CF$_3$ | O |
| 3.83 | H | C≡CF | Me | CF$_2$H | O |
| 3.84 | H | C≡CF | Me | Me | O |
| 3.85 | H | C≡CCF$_2$Cl | Me | CF$_3$ | O |
| 3.86 | H | C≡CCF$_2$Cl | Me | CF$_2$H | O |
| 3.87 | H | C≡CCF$_2$Cl | Me | Me | O |
| 3.88 | H | C≡CCF$_2$H | Me | CF$_3$ | O |
| 3.89 | H | C≡CCF$_2$H | Me | CF$_2$H | O |
| 3.90 | H | C≡CCF$_2$H | Me | Me | O |
| 3.91 | H | C≡CCF$_2$Br | Me | CF$_3$ | O |
| 3.92 | H | C≡CCF$_2$Br | Me | CF$_2$H | O |
| 3.93 | H | C≡CCF$_2$Br | Me | Me | O |
| 3.94 | H | C≡CCH$_2$F | Me | CF$_3$ | O |
| 3.95 | H | C≡CCH$_2$F | Me | CF$_2$H | O |
| 3.96 | H | C≡CCH$_2$F | Me | Me | O |
| 3.97 | H | C≡CCH(Me)F | Me | CF$_3$ | O |
| 3.98 | H | C≡CCH(Me)F | Me | CF$_2$H | O |
| 3.99 | H | C≡CCH(Me)F | Me | Me | O |
| 3.100 | H | C≡CC(Me)$_2$F | Me | CF$_3$ | O |
| 3.101 | H | C≡CC(Me)$_2$F | Me | CF$_2$H | O |
| 3.102 | H | C≡CC(Me)$_2$F | Me | Me | O |
| 3.103 | H | C≡CCH$_2$C(Me)$_3$ | Me | CF$_3$ | O |
| 3.104 | H | C≡CCH$_2$C(Me)$_3$ | Me | CF$_2$H | O |
| 3.105 | H | C≡CCH$_2$C(Me)$_3$ | Me | Me | O |
| 3.106 | H | C≡CCH(Me)$_2$ | Me | CF$_3$ | O |
| 3.107 | H | C≡CCH(Me)$_2$ | Me | CF$_2$H | O |
| 3.108 | H | C≡CCH(Me)$_2$ | Me | Me | O |
| 3.109 | H | C≡CCH$_2$CH(Me)$_2$ | Me | CF$_3$ | O |
| 3.110 | H | C≡CCH$_2$CH(Me)$_2$ | Me | CF$_2$H | O |
| 3.111 | H | C≡CCH$_2$CH(Me)$_2$ | Me | Me | O |
| 3.112 | H | CH$_2$C≡CCMe$_3$ | Me | CF$_3$ | O |
| 3.113 | H | CH$_2$C≡CCMe$_3$ | Me | CF$_2$H | O |
| 3.114 | H | CH$_2$C≡CCMe$_3$ | Me | Me | O |
| 3.115 | H | CF$_2$C≡CCMe$_3$ | Me | CF$_3$ | O |
| 3.116 | H | CF$_2$C≡CCMe$_3$ | Me | CF$_2$H | O |
| 3.117 | H | CF$_2$C≡CCMe$_3$ | Me | Me | O |
| 3.118 | H | CF$_2$C≡CMe | Me | CF$_3$ | O |
| 3.119 | H | CF$_2$C≡CMe | Me | CF$_2$H | O |
| 3.120 | H | CF$_2$C≡CMe | Me | Me | O |
| 3.121 | H | CF$_2$C≡CH | Me | CF$_3$ | O |
| 3.122 | H | CF$_2$C≡CH | Me | CF$_2$H | O |
| 3.123 | H | CF$_2$C≡CH | Me | Me | O |
| 3.124 | H | CMe$_2$C≡CH | Me | CF$_3$ | O |
| 2.125 | H | CMe$_2$C≡CH | Me | CF$_2$H | O |
| 3.126 | H | CMe$_2$C≡CH | Me | Me | O |
| 3.127 | H | CHFC≡CH | Me | CF$_3$ | O |
| 3.128 | H | CHFC≡CH | Me | CF$_2$H | O |
| 3.129 | H | CHFC≡CH | Me | Me | O |
| 3.130 | H | CHMeC≡CH | Me | CF$_3$ | O |
| 3.131 | H | CHMeC≡CH | Me | CF$_2$H | O |
| 3.132 | H | CHMeC≡CH | Me | Me | O |
| 3.133 | H | CH(CF$_3$)C≡CH | Me | CF$_3$ | O |
| 3.134 | H | CH(CF$_3$)C≡CH | Me | CF$_2$H | O |
| 3.135 | H | CH(CF$_3$)C≡CH | Me | Me | O |
| 3.136 | H | C≡C(1-F-cyclopentyl) | Me | CF$_3$ | O |
| 3.137 | H | C≡C(1-F-cyclopentyl) | Me | CHF$_2$ | O |
| 3.138 | H | C≡CCH$_2$OMe | Me | CF$_3$ | O |
| 3.139 | H | C≡CCH$_2$OMe | Me | CF$_2$H | O |
| 3.140 | H | C≡CCH$_2$OMe | Me | Me | O |
| 3.141 | H | C≡CCMe$_2$OMe | Me | CF$_3$ | O |
| 3.142 | H | C≡CCMe$_2$OMe | Me | CF$_2$H | O |
| 3.143 | H | C≡CCMe$_2$OMe | Me | Me | O |
| 3.144 | H | C≡CCMe$_2$OCOMe | Me | CF$_3$ | O |
| 3.145 | H | C≡CCMe$_2$OCOMe | Me | CF$_2$H | O |
| 3.146 | H | C≡CCF$_2$Me | Me | CF$_3$ | O |
| 3.147 | H | C≡CCF$_2$Me | Me | CF$_2$H | O |
| 3.148 | H | C≡CCF$_2$Me | Me | Me | O |
| 3.149 | H | C≡CC(Me)=CH$_2$ | Me | CF$_3$ | O |
| 3.150 | H | C≡CC(Me)=CH$_2$ | Me | CF$_2$H | O |
| 3.151 | H | CH=CFCl | Me | CF$_3$ | O |
| 3.152 | H | CH=CFCl | Me | CF$_2$H | O |
| 3.153 | H | CH=CFCl | Me | Me | O |
| 3.154 | H | CH=CFBr | Me | CF$_3$ | O |
| 3.155 | H | CH=CFBr | Me | CF$_2$H | O |
| 3.156 | H | CH=CFBr | Me | Me | O |
| 3.157 | H | CH=CHBr | Me | CF$_3$ | O |
| 3.158 | H | CH=CHBr | Me | CF$_2$H | O |
| 3.159 | H | CH=CHBr | Me | Me | O |
| 3.160 | H | CH=CHF | Me | CF$_3$ | O |
| 3.161 | H | CH=CHF | Me | CF$_2$H | O |
| 3.162 | H | CH=CHF | Me | Me | O |
| 3.163 | H | CMe=CHCF$_3$ | Me | CF$_3$ | O |
| 3.164 | H | CMe=CHCF$_3$ | Me | CF$_2$H | O |
| 3.165 | H | CMe=CHCF$_3$ | Me | Me | O |
| 3.166 | H | CH=CFCF$_3$ | Me | CF$_3$ | O |
| 3.167 | H | CH=CFCF$_3$ | Me | CF$_2$H | O |
| 3.168 | H | CH=CFCF$_3$ | Me | Me | O |
| 3.169 | H | CH=CBrCF$_3$ | Me | CF$_3$ | O |
| 3.170 | H | CH=CBrCF$_3$ | Me | CF$_2$H | O |
| 3.171 | H | CH=CBrCF$_3$ | Me | Me | O |
| 3.172 | H | CH=CHC$_2$F$_5$ | Me | CF$_3$ | O |
| 3.173 | H | CH=CHC$_2$F$_5$ | Me | CF$_2$H | O |
| 3.174 | H | CH=CHC$_2$F$_5$ | Me | Me | O |
| 3.175 | H | CH=CHCl | Me | CF$_3$ | O |
| 3.176 | H | CH=CHCl | Me | CF$_2$H | O |
| 3.177 | H | CH=CHCl | Me | Me | O |
| 3.178 | H | CH=C(CF$_3$)$_2$ | Me | CF$_3$ | O |
| 3.179 | H | CH=C(CF$_3$)$_2$ | Me | CF$_2$H | O |
| 3.180 | H | CH=C(CF$_3$)$_2$ | Me | Me | O |
| 3.181 | H | CMe=CFCl | Me | CF$_3$ | O |
| 3.182 | H | CMe=CFCl | Me | CF$_2$H | O |
| 3.183 | H | CMe=CFCl | Me | Me | O |
| 3.184 | H | CMe=CFBr | Me | CF$_3$ | O |
| 3.185 | H | CMe=CFBr | Me | CF$_2$H | O |
| 3.186 | H | CMe=CFBr | Me | Me | O |
| 3.187 | H | CMe=CF$_2$ | Me | CF$_3$ | O |
| 3.188 | H | CMe=CF$_2$ | Me | CF$_2$H | O |
| 3.189 | H | CMe=CF$_2$ | Me | Me | O |
| 3.190 | H | CMe=CCl$_2$ | Me | CF$_3$ | O |
| 3.191 | H | CMe=CCl$_2$ | Me | CF$_2$H | O |
| 3.192 | H | CMe=CCl$_2$ | Me | Me | O |
| 3.193 | H | CMe=CBr$_2$ | Me | CF$_3$ | O |
| 3.194 | H | CMe=CBr$_2$ | Me | CF$_2$H | O |
| 3.195 | H | CMe=CBr$_2$ | Me | Me | O |
| 3.196 | H | CMe=CFCF$_3$ | Me | CF$_3$ | O |
| 3.197 | H | CMe=CFCF$_3$ | Me | CF$_2$H | O |
| 3.198 | H | CMe=CFCF$_3$ | Me | Me | O |
| 3.199 | H | CMe=CClCF$_3$ | Me | CF$_3$ | O |
| 3.200 | H | CMe=CClCF$_3$ | Me | CF$_2$H | O |
| 3.201 | H | CMe=CClCF$_3$ | Me | Me | O |
| 3.202 | H | CCF$_3$=CF$_2$ | Me | CF$_3$ | O |
| 3.203 | H | CCF$_3$=CF$_2$ | Me | CF$_2$H | O |
| 3.204 | H | CCF$_3$=CF$_2$ | Me | Me | O |
| 3.205 | H | CCF$_3$=CCl$_2$ | Me | CF$_3$ | O |
| 3.206 | H | CCF$_3$=CCl$_2$ | Me | CF$_2$H | O |
| 3.207 | H | CCF$_3$=CCl$_2$ | Me | Me | O |
| 3.208 | H | CCF$_3$=CBr$_2$ | Me | CF$_3$ | O |
| 3.209 | H | CCF$_3$=CBr$_2$ | Me | CF$_2$H | O |
| 3.210 | H | CCF$_3$=CBr$_2$ | Me | Me | O |
| 3.211 | H | CCF$_3$=CH$_2$ | Me | CF$_3$ | O |
| 3.212 | H | CCF$_3$=CH$_2$ | Me | CF$_2$H | O |
| 3.213 | H | CCF$_3$=CH$_2$ | Me | Me | O |
| 3.214 | H | CCF$_3$=CFBr | Me | CF$_3$ | O |
| 3.215 | H | CCF$_3$=CFBr | Me | CF$_2$H | O |
| 3.216 | H | CCF$_3$=CFBr | Me | Me | O |
| 3.217 | H | CCF$_3$=CHF | Me | CF$_3$ | O |
| 3.218 | H | CCF$_3$=CHF | Me | CF$_2$H | O |
| 3.219 | H | CCF$_3$=CHF | Me | Me | O |
| 3.220 | H | CCF$_3$=CFCl | Me | CF$_3$ | O |
| 3.221 | H | CCF$_3$=CFCl | Me | CF$_2$H | O |
| 3.222 | H | CCF$_3$=CFCl | Me | Me | O |

TABLE 3-continued

| Compound No. | R¹ | R⁷ | R⁹ | R¹⁰ | X |
|---|---|---|---|---|---|
| 3.223 | H | CCF₃=CHCl | Me | CF₃ | O |
| 3.224 | H | CCF₃=CHCl | Me | CF₂H | O |
| 3.225 | H | CCF₃=CHCl | Me | Me | O |
| 3.226 | H | CH=CFCF₂Cl | Me | CF₃ | O |
| 3.227 | H | CH=CFCF₂Cl | Me | CF₂H | O |
| 3.228 | H | CH=CFCF₂Cl | Me | Me | O |
| 3.229 | H | CH=CClCF₂Cl | Me | CF₃ | O |
| 3.230 | H | CH=CClCF₂Cl | Me | CF₂H | O |
| 3.231 | H | CH=CClCF₂Cl | Me | Me | O |
| 3.232 | H | CH₂CF=CF₂ | Me | CF₃ | O |
| 3.233 | H | CH₂CF=CF₂ | Me | CF₂H | O |
| 3.234 | H | CH₂CF=CF₂ | Me | Me | O |
| 3.235 | H | CF=CFBr | Me | CF₃ | O |
| 3.236 | H | CF=CFBr | Me | CF₂H | O |
| 3.237 | H | CF=CFBr | Me | Me | O |
| 3.238 | H | CH₂CH=CF₂ | Me | CF₃ | O |
| 3.239 | H | CH₂CH=CF₂ | Me | CF₂H | O |
| 3.240 | H | CH₂CH=CF₂ | Me | Me | O |
| 3.241 | H | CH₂CH=CCl₂ | Me | CF₃ | O |
| 3.242 | H | CH₂CH=CCl₂ | Me | CF₂H | O |
| 3.243 | H | CH₂CH=CCl₂ | Me | Me | O |
| 3.244 | H | CH₂CH=CBr₂ | Me | CF₃ | O |
| 3.245 | H | CH₂CH=CBr₂ | Me | CF₂H | O |
| 3.246 | H | CH₂CH=CBr₂ | Me | Me | O |
| 3.247 | H | CCl=CF₂ | Me | CF₃ | O |
| 3.248 | H | CCl=CF₂ | Me | CF₂H | O |
| 3.249 | H | CCl=CF₂ | Me | Me | O |
| 3.250 | H | C≡CMe₂OH | Me | CF₃ | O |
| 3.251 | H | C≡CCH₂CH₃ | Me | CF₂H | O |
| 3.252 | H | C≡CCH₂CH₃ | Me | Me | O |
| 3.253 | H | C≡CCH₂CH₃ | Me | CF₃ | O |
| 3.254 | H | C≡CCF=CF₂ | Me | CF₃ | O |
| 3.255 | H | C≡CCF=CF₂ | Me | CF₂H | O |
| 3.256 | H | C≡CCHFCl | Me | CF₃ | O |
| 3.257 | H | C≡CCHFCl | Me | CF₂H | O |
| 3.258 | H | C≡CCHFCl | Me | Me | O |
| 3.259 | H | CH=CFC₂F₅ | Me | CF₃ | O |
| 3.260 | H | CH=CFC₂F₅ | Me | CF₂H | O |
| 3.261 | H | CH=CFC₂F₅ | Me | Me | O |
| 3.262 | H | C≡CCF₂CH₂CH₃ | Me | CF₃ | O |
| 3.263 | H | C≡CCF₂CH₂CH₃ | Me | CF₂H | O |
| 3.264 | H | C≡CCF₂CH₂CH₃ | Me | Me | O |
| 3.265 | H | C≡CCHFCH₂CH₃ | Me | CF₃ | O |
| 3.266 | H | C≡CCHFCH₂CH₃ | Me | CF₂H | O |
| 3.267 | H | C≡CCHFCH₂CH₃ | Me | Me | O |
| 3.268 | H | C≡CCF(CF₃)₂ | Me | CF₃ | O |
| 3.269 | H | C≡CCF(CF₃)₂ | Me | CF₂H | O |
| 3.270 | H | C≡CCF(CF₃)₂ | Me | Me | O |
| 3.271 | H | CH=CClC₂F₅ | Me | CF₃ | O |
| 3.272 | H | CH=CClC₂F₅ | Me | CF₂H | O |
| 3.273 | H | CH=CClC₂F₅ | Me | Me | O |
| 3.274 | H | C≡CC₂F₅ | Me | CF₃ | O |
| 3.275 | H | C≡CC₂F₅ | Me | CF₂H | O |
| 3.276 | H | C≡CC₂F₅ | Me | Me | O |

Table 3 provides 276 compounds of fornula (Ic):

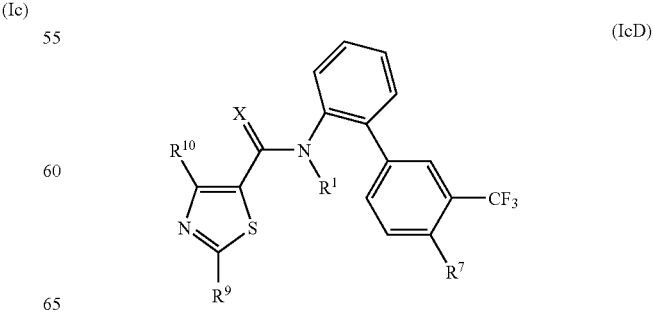

(Ic)

wherein R¹, R⁷, R⁹, R¹⁰ and X are as defined in Table 3.

Table 3 provides 276 compounds of formula (IcA) wherein R¹, R⁷, R⁹, R¹⁰ and X are as defined in Table 3.

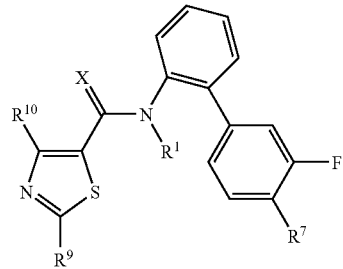

(IcA)

Table 3 provides 276 compounds of formula (IcB) wherein R¹, R⁷, R⁹, R¹⁰ and X are as defined in Table 3.

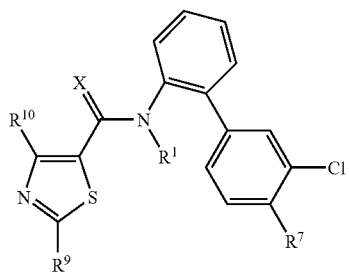

(IcB)

Table 3 provides 276 compounds of formula (IcC) wherein R¹, R⁷, R⁹, R¹⁰ and X are as defined in Table 3.

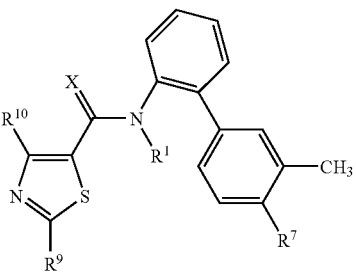

(IcC)

Table 3 provides 276 compounds of formula (IcD) wherein R¹, R⁷, R⁹, R¹⁰ and X are as defined in Table 3.

(IcD)

Table 3 provides 276 compounds of formula (IcE) wherein $R^1$, $R^7$, $R^9$, $R^{10}$ and X are as defined in Table 3.

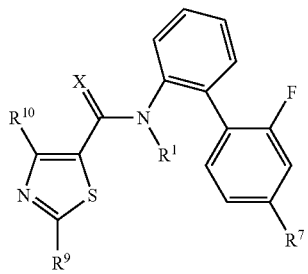
(IcE)

Table 3 provides 276 compounds of formula (IcF) wherein $R^1$, $R^7$, $R^9$, $R^{10}$ and X are as defined in Table 3.

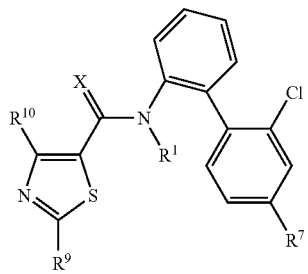
(IcF)

Table 3 provides 276 compounds of formula (IcG) wherein $R^1$, $R^7$, $R^9$, $R^{10}$ and X are as defined in Table 3.

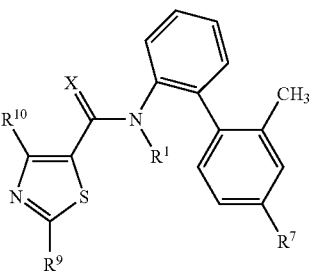
(IcG)

Table 4 provides 3 compounds of formula (Id):

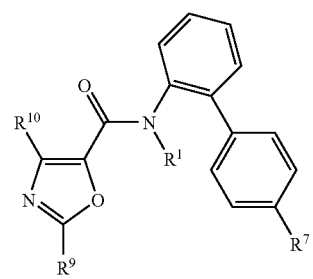
(Id)

wherein $R^1$, $R^7$, $R^9$, $R^{10}$ are as defined in Table 4.

TABLE 4

| Compound No. | $R^1$ | $R^7$ | $R^9$ | $R^{10}$ |
|---|---|---|---|---|
| 4.01 | H | C≡CH | Me | $CF_3$ |
| 4.02 | H | C≡CSiMe$_3$ | Me | $CF_3$ |
| 4.03 | H | CH=CH$_2$ | Me | $CF_3$ |

Table 5 provides 15 compounds of formula (Ie):

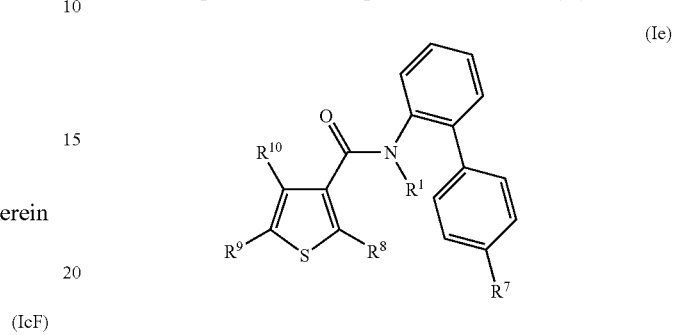
(Ie)

wherein $R^1$, $R^7$, $R^9$, $R^{10}$ are as defined in Table 5.

TABLE 5

| Compound No. | $R^1$ | $R^7$ | $R^8$ | $R^9$ | $R^{10}$ |
|---|---|---|---|---|---|
| 5.01 | H | C≡CH | H | H | $CF_3$ |
| 5.02 | H | C≡CH | Me | Me | Me |
| 5.03 | H | C≡CH | H | Me | $CF_3$ |
| 5.04 | H | C≡CH | Me | Me | H |
| 5.05 | COMe | C≡CH | Me | Me | H |
| 5.06 | COMe | C≡CH | Me | Me | Me |
| 5.07 | COEt | C≡CH | Me | Me | Me |
| 5.08 | H | C≡CSiMe$_3$ | H | H | $CF_3$ |
| 5.09 | H | C≡CSiMe$_3$ | Me | Me | Me |
| 5.10 | H | C≡CSiMe$_3$ | H | Me | $CF_3$ |
| 5.11 | H | C≡CSiMe$_3$ | Me | Me | H |
| 5.12 | H | C≡CSiMe$_3$ | H | H | $CF_3$ |
| 5.13 | H | CH=CH$_2$ | Me | Me | Me |
| 5.14 | H | CH=CH$_2$ | H | Me | $CF_3$ |
| 5.15 | H | CH=CH$_2$ | Me | Me | H |

Table 6 provides 15 compounds of formula (If):

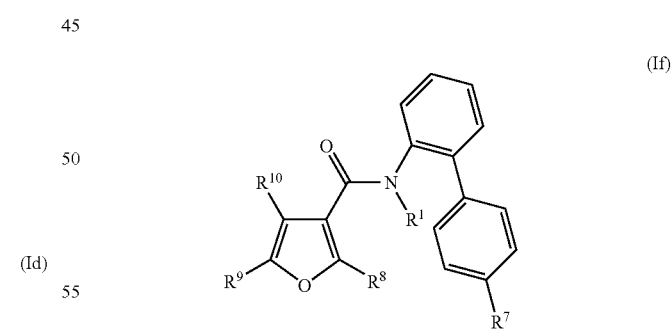
(If)

wherein $R^1$, $R^7$, $R^9$, $R^{10}$ are as defined in Table 6.

TABLE 6

| Compound No. | $R^1$ | $R^7$ | $R^8$ | $R^9$ | $R^{10}$ |
|---|---|---|---|---|---|
| 6.01 | H | C≡CH | H | H | $CF_3$ |
| 6.02 | H | C≡CH | Me | Me | Me |

TABLE 6-continued

| Compound No. | R¹ | R⁷ | R⁸ | R⁹ | R¹⁰ |
|---|---|---|---|---|---|
| 6.03 | H | C≡CH | H | Me | CF₃ |
| 6.04 | H | C≡CH | Me | Me | H |
| 6.05 | COMe | C≡CH | Me | Me | H |
| 6.06 | COMe | C≡CH | Me | Me | Me |
| 6.07 | COEt | C≡CH | Me | Me | Me |
| 6.08 | H | C≡CSiMe₃ | H | H | CF₃ |
| 6.09 | H | C≡CSiMe₃ | Me | Me | Me |
| 6.10 | H | C≡CSiMe₃ | H | Me | CF₃ |
| 6.11 | H | C≡CSiMe₃ | Me | Me | H |
| 6.12 | H | C≡CSiMe₃ | H | H | CF₃ |
| 6.13 | H | CH=CH₂ | Me | Me | Me |
| 6.14 | H | CH=CH₂ | H | Me | CF₃ |
| 6.15 | H | CH=CH₂ | Me | Me | H |

Table 7 provides 10 compounds of formula (Ig):

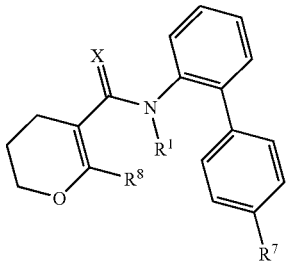

(Ig)

wherein R¹, R⁷, R⁸ and X are as defined in Table 7.

TABLE 7

| Compound No. | R¹ | R⁷ | R⁸ | X |
|---|---|---|---|---|
| 7.01 | H | C≡CH | CF₃ | O |
| 7.02 | H | C≡CH | Me | O |
| 7.03 | H | C≡CH | CF₃ | S |
| 7.04 | COMe | C≡CH | Me | O |
| 7.05 | H | C≡CSiMe₃ | CF₃ | O |
| 7.06 | H | C≡CSiMe₃ | Me | O |
| 7.07 | H | CH=CH₂ | Me | O |
| 7.08 | H | CH=CH₂ | CF₃ | O |
| 7.09 | propargyl | CH=CH₂ | Me | O |
| 7.10 | allenyl | CH=CH₂ | Me | O |

Table 8 provides 10 compounds of formulae (Ih):

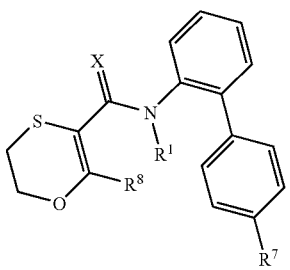

(Ih)

wherein R¹, R⁷, R⁸ and X are as defined in Table 8.

TABLE 8

| Compound No. | R¹ | R⁷ | R⁸ | X |
|---|---|---|---|---|
| 8.01 | H | C≡CH | CF₃ | O |
| 8.02 | H | C≡CH | Me | O |
| 8.03 | H | C≡CH | CF₃ | S |
| 8.04 | COMe | C≡CH | Me | O |
| 8.05 | H | C≡CSiMe₃ | CF₃ | O |
| 8.06 | H | C≡CSiMe₃ | Me | O |
| 8.07 | H | CH=CH₂ | CF₃ | O |
| 8.08 | H | CH=CH₂ | CF₃ | O |
| 8.09 | propargyl | CH=CH₂ | Me | O |
| 8.10 | allenyl | CH=CH₂ | Me | O |

TABLE 9

| Compound No. | R¹ | R⁷ | R⁸ |
|---|---|---|---|
| 9.01 | H | C≡CH | Cl |
| 9.02 | H | C≡CH | CF₃ |
| 9.03 | COMe | C≡CH | Cl |
| 9.04 | H | C≡CH | Br |
| 9.05 | COCH₂OMe | C≡CH | Cl |
| 9.06 | H | C≡CSiMe₃ | Cl |
| 9.07 | H | C≡CSiMe₃ | CF₃ |
| 9.08 | H | C≡CSiMe₃ | Br |
| 9.09 | H | CH=CH₂ | CF₃ |
| 9.10 | H | CH=CH₂ | Br |
| 9.11 | H | CH=CH₂ | Cl |
| 9.12 | H | CH=CH₂ | CH₃ |
| 9.13 | propargyl | CH=CH₂ | Cl |
| 9.14 | allenyl | CH=CH₂ | Cl |
| 9.15 | H | C≡CCl | Cl |
| 9.16 | H | C≡CCl | CF₃ |
| 9.17 | H | C≡CCl | Br |
| 9.18 | H | C≡CBr | Cl |
| 9.19 | H | C≡CBr | CF₃ |
| 9.20 | H | C≡CBr | Br |
| 9.21 | H | C≡CCF₃ | Cl |
| 9.22 | H | C≡CCF₃ | CF₃ |
| 9.23 | H | C≡CCF₃ | Br |
| 9.24 | H | CH=CF₂ | CF₃ |
| 9.25 | H | CH=CF₂ | Br |
| 9.26 | H | CH=CF₂ | Cl |
| 9.27 | H | CCl=CH₂ | CF₃ |
| 9.28 | H | CCl=CH₂ | Br |
| 9.29 | H | CCl=CH₂ | Cl |
| 9.30 | H | CBr=CH₂ | CF₃ |
| 9.31 | H | CBr=CH₂ | Br |
| 9.32 | H | CBr=CH₂ | Cl |
| 9.33 | H | CF=CHF | CF₃ |
| 9.34 | H | CF=CHF | Br |
| 9.35 | H | CF=CHF | Cl |
| 9.36 | H | CH=CHCF₃ | CF₃ |
| 9.37 | H | CH=CHCF₃ | Br |
| 9.38 | H | CH=CHCF₃ | Cl |
| 9.39 | H | CH=CClCF₃ | CF₃ |
| 9.40 | H | CH=CClCF₃ | Br |
| 9.41 | H | CH=CClCF₃ | Cl |
| 9.42 | H | CH₂C≡CH | CF₃ |
| 9.43 | H | CH₂C≡CH | Br |
| 9.44 | H | CH₂C≡CH | Cl |
| 9.45 | H | CH₂C≡CSiMe₃ | CF₃ |
| 9.46 | H | CH₂C≡CSiMe₃ | Br |
| 9.47 | H | CH₂C≡CSiMe₃ | Cl |
| 9.48 | H | C≡CMe | CF₃ |
| 9.49 | H | C≡CMe | Br |
| 9.50 | H | C≡CMe | Cl |
| 9.51 | H | CH=CCl₂ | CF₃ |
| 9.52 | H | CH=CCl₂ | Br |
| 9.53 | H | CH=CCl₂ | Cl |
| 9.54 | H | CH=CHSiMe₃ | CF₃ |
| 9.55 | H | CH=CHSiMe₃ | Br |
| 9.56 | H | CH=CHSiMe₃ | Cl |
| 9.57 | H | C≡C(cyclopropyl) | Cl |
| 9.58 | H | SiMe₃ | Cl |
| 9.59 | H | C≡CCMe₃ | Cl |

TABLE 9-continued

| Compound No. | R¹ | R⁷ | R⁸ |
|---|---|---|---|
| 9.60 | H | CH=CBr₂ | CF₃ |
| 9.61 | H | CH=CBr₂ | Br |
| 9.62 | H | CH=CBr₂ | Cl |
| 9.63 | H | CF=CF₂ | CF₃ |
| 9.64 | H | CF=CF₂ | Br |
| 9.65 | H | CF=CF₂ | Cl |
| 9.66 | H | C≡CCMe₃ | CF₃ |
| 9.67 | H | C≡CCMe₃ | Br |
| 9.68 | allenyl | C≡CCMe₃ | Cl |
| 9.69 | H | C≡C(cyclopropyl) | CF₃ |
| 9.70 | H | C≡C(cyclopropyl) | Br |
| 9.71 | H | C≡CF | CF₃ |
| 9.72 | H | C≡CF | Br |
| 9.73 | H | C≡CF | Cl |
| 9.74 | H | C≡CCF₂Cl | Cl |
| 9.75 | H | C≡CCF₂Cl | CF₃ |
| 9.76 | H | C≡CCF₂Cl | Br |
| 9.77 | H | C≡CCF₂H | Cl |
| 9.78 | H | C≡CCF₂H | CF₃ |
| 9.79 | H | C≡CCF₂H | Br |
| 9.80 | H | C≡CCF₂Br | Cl |
| 9.81 | H | C≡CCF₂Br | CF₃ |
| 9.82 | H | C≡CCF₂Br | Br |
| 9.83 | H | C≡CCH₂F | Cl |
| 9.84 | H | C≡CCH₂F | CF₃ |
| 9.85 | H | C≡CCH₂F | Br |
| 9.86 | H | C≡CCH(Me)F | Cl |
| 9.87 | H | C≡CCH(Me)F | CF₃ |
| 9.88 | H | C≡CCH(Me)F | Br |
| 9.89 | H | C≡CC(Me)₂F | Cl |
| 9.90 | H | C≡CC(Me)₂F | CF₃ |
| 9.91 | H | C≡CC(Me)₂F | Br |
| 9.92 | H | C≡CCH₂CMe₃ | Cl |
| 9.93 | H | C≡CCH₂CMe₃ | Br |
| 9.94 | H | C≡CCHMe₂ | CF₃ |
| 9.95 | H | C≡CCHMe₂ | Br |
| 9.96 | H | C≡CCHMe₂ | Cl |
| 9.97 | H | C≡CCH₂CHMe₂ | CF₃ |
| 9.98 | H | C≡CCH₂CHMe₂ | Br |
| 9.99 | H | C≡CCH₂CHMe₂ | Cl |
| 9.100 | H | CF₂C≡CMe | CF₃ |
| 9.101 | H | CF₂C≡CMe | Br |
| 9.102 | H | CF₂C≡CMe | Cl |
| 9.103 | H | CF₂C≡CH | CF₃ |
| 9.104 | H | CF₂C≡CH | Br |
| 9.105 | H | CF₂C≡CH | Cl |
| 9.106 | H | CHFC≡CH | CF₃ |
| 9.107 | H | CHFC≡CH | Br |
| 9.108 | H | CHFC≡CH | Cl |
| 9.109 | H | C≡C(1-F-cyclopentyl) | CF₃ |
| 9.110 | H | C≡C(1-F-cyclopentyl) | Br |
| 9.111 | H | C≡C(1-F-cyclopentyl) | Cl |
| 9.112 | H | C≡CCH₂OMe | Cl |
| 9.113 | H | C≡CCH₂OMe | Br |
| 9.114 | H | C≡CCH₂OMe | CF₃ |
| 9.115 | H | C≡CCMe₂OMe | Cl |
| 9.116 | H | C≡CCMe₂OMe | Br |
| 9.117 | H | C≡CCMe₂OMe | CF₃ |
| 9.118 | H | C≡CCMe₂OCOMe | Cl |
| 9.119 | H | C≡CCMe₂OCOMe | Br |
| 9.120 | H | C≡CCMe₂OCOMe | CF₃ |
| 9.121 | H | C≡CCF₂Me | Cl |
| 9.122 | H | C≡CCF₂Me | Br |
| 9.123 | H | C≡CCF₂Me | CF₃ |
| 9.124 | H | CH=CFCl | CF₃ |
| 9.125 | H | CH=CFCl | Br |
| 9.126 | H | CH=CFCl | Cl |
| 9.127 | H | CH=CFBr | CF₃ |
| 9.128 | H | CH=CFBr | Br |
| 9.129 | H | CH=CFBr | Cl |
| 9.130 | H | CH=CHBr | CF₃ |
| 9.131 | H | CH=CHBr | Br |
| 9.132 | H | CH=CHBr | Cl |
| 9.133 | H | CMe=CHCF₃ | CF₃ |
| 9.134 | H | CMe=CHCF₃ | Br |
| 9.135 | H | CMe=CHCF₃ | Cl |
| 9.136 | H | CH=CFCF₃ | CF₃ |
| 9.137 | H | CH=CFCF₃ | Br |
| 9.138 | H | CH=CFCF₃ | Cl |
| 9.139 | H | CH=CBrCF₃ | CF₃ |
| 9.140 | H | CH=CBrCF₃ | Br |
| 9.141 | H | CH=CBrCF₃ | Cl |
| 9.142 | H | CH=CHC₂F₅ | CF₃ |
| 9.143 | H | CH=CHC₂F₅ | Br |
| 9.144 | H | CH=CHC₂F₅ | Cl |
| 9.145 | H | CH=CHCl | CF₃ |
| 9.146 | H | CH=CHCl | Br |
| 9.147 | H | CH=CHCl | Cl |
| 9.148 | H | CH=C(CF₃)₂ | Cl |
| 9.149 | H | CMe=CFCl | CF₃ |
| 9.150 | H | CMe=CFCl | Br |
| 9.151 | H | CMe=CFCl | Cl |
| 9.152 | H | CMe=CFBr | CF₃ |
| 9.153 | H | CMe=CFBr | Br |
| 9.154 | H | CMe=CFBr | Cl |
| 9.155 | H | CMe=CF₂ | CF₃ |
| 9.156 | H | CMe=CF₂ | Br |
| 9.157 | H | CMe=CF₂ | Cl |
| 9.158 | H | CMe=CCl₂ | CF₃ |
| 9.159 | H | CMe=CCl₂ | Br |
| 9.160 | H | CMe=CCl₂ | Cl |
| 9.161 | H | CMe=CBr₂ | CF₃ |
| 9.162 | H | CMe=CBr₂ | Br |
| 9.163 | H | CMe=CBr₂ | Cl |
| 9.164 | H | CCF₃=CF₂ | CF₃ |
| 9.165 | H | CCF₃=CF₂ | Br |
| 9.166 | H | CCF₃=CF₂ | Cl |
| 9.167 | H | CCF₃=CCl₂ | CF₃ |
| 9.168 | H | CCF₃=CCl₂ | Br |
| 9.169 | H | CCF₃=CCl₂ | Cl |
| 9.170 | H | CCF₃=CBr₂ | CF₃ |
| 9.171 | H | CCF₃=CBr₂ | Br |
| 9.172 | H | CCF₃=CBr₂ | Cl |
| 9.173 | H | CCF₃=CH₂ | CF₃ |
| 9.174 | H | CCF₃=CH₂ | Br |
| 9.175 | H | CCF₃=CH₂ | Cl |
| 9.176 | H | CCF₃=CFBr | CF₃ |
| 9.177 | H | CCF₃=CFBr | Br |
| 9.178 | H | CCF₃=CFBr | Cl |
| 9.179 | H | CCF₃=CFCl | CF₃ |
| 9.180 | H | CCF₃=CFCl | Br |
| 9.181 | H | CCF₃=CFCl | Cl |
| 9.182 | H | CH=CFCF₂Cl | CF₃ |
| 9.183 | H | CH=CFCF₂Cl | Br |
| 9.184 | H | CH=CFCF₂Cl | Cl |
| 9.185 | H | CH=CClCF₂Cl | Cl |
| 9.186 | H | CH₂CF=CF₂ | CF₃ |
| 9.187 | H | CH₂CF=CF₂ | Br |
| 9.188 | H | CH₂CF=CF₂ | Cl |
| 9.189 | H | CF=CFBr | Cl |
| 9.190 | H | CH₂CH=CF₂ | Cl |
| 9.191 | H | CH₂CH=CCl₂ | Cl |
| 9.192 | H | CH₂CH=CBr₂ | Cl |
| 9.193 | H | CH₂CH=CBr₂ | CF₃ |
| 9.194 | H | CH₂CH=CBr₂ | Br |
| 9.195 | H | CCl=CF₂ | Cl |
| 9.196 | H | C≡CMe | CHF₂ |
| 9.197 | H | C≡CCHMe₂ | CHF₂ |
| 9.198 | H | C≡CCH₂CHMe₂ | CHF₂ |
| 9.199 | H | C≡CCF₃ | CHF₂ |
| 9.200 | H | C≡CH | CHF₂ |
| 9.201 | H | C≡CCH₂SiMe₃ | Cl |
| 9.202 | H | C≡CCH₂CF₃ | Cl |
| 9.203 | H | C≡CSi(Me)₂CMe₃ | Cl |
| 9.204 | H | C≡CCH₂CH₃ | Cl |
| 9.205 | H | C≡CCF=CF₂ | Cl |
| 9.206 | H | C≡CCHFCl | Cl |
| 9.207 | H | CH=CFC₂F₅ | Cl |
| 9.208 | H | C≡CCF₂CH₂CH₃ | Cl |
| 9.209 | H | C≡CCHFCH₂CH₃ | Cl |
| 9.210 | H | C≡CCF(CF₃)₂ | Cl |
| 9.211 | H | CH=CClC₂F₅ | Cl |
| 9.212 | H | C≡CC₂F₅ | Cl |

Table 9 provides 212 compounds of formula (Ii):

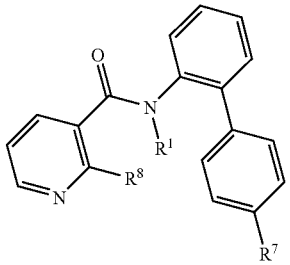
(Ii)

wherein $R^1$, $R^7$ and $R^8$ are as defined in Table 9.

Table 9 provides 212 compounds of formula (IiA) wherein $R^1$, $R^7$ and $R^8$ are as defined in Table 9.

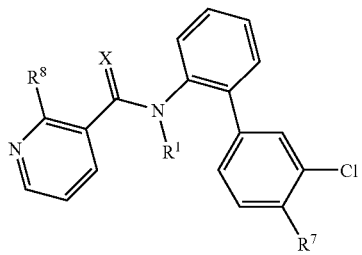
(IiA)

Table 9 provides 212 compounds of formula (IiB) wherein $R^1$, $R^7$ and $R^8$ are as defined in Table 9.

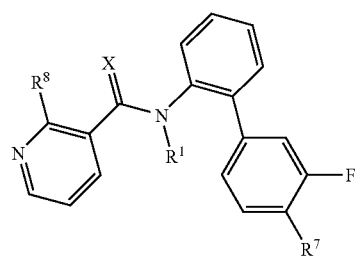
(IiB)

Table 9 provides 212 compounds of formula (IiC) wherein $R^1$, $R^7$ and $R^8$ are as defined in Table 9.

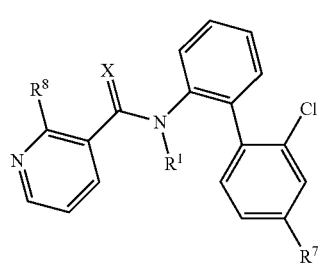
(IiC)

Table 9 provides also 212 compounds of formula (IiD) wherein $R^1$, $R^7$ and $R^8$ are as defined in Table 9.

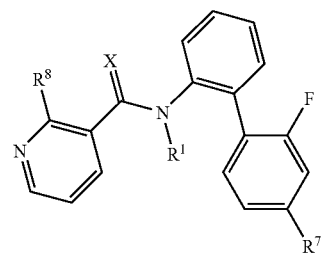
(IiD)

Table 10 provides 14 compounds of formula (Ij):

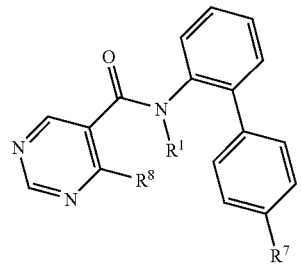
(Ij)

wherein $R^1$, $R^7$ and $R^8$ are as defined in Table 10.

TABLE 10

| Compound No. | $R^1$ | $R^7$ | $R^8$ |
|---|---|---|---|
| 10.01 | H | C≡CH | Cl |
| 10.02 | H | C≡CH | CF$_3$ |
| 10.03 | COMe | C≡CH | Cl |
| 10.04 | H | C≡CH | Br |
| 10.05 | COCH$_2$OMe | C≡CH | Cl |
| 10.06 | H | C≡CSiMe$_3$ | Cl |
| 10.07 | H | C≡CSiMe$_3$ | CF$_3$ |
| 10.08 | H | C≡CSiMe$_3$ | Br |
| 10.09 | H | CH=CH$_2$ | CF$_3$ |
| 10.10 | H | CH=CH$_2$ | Br |
| 10.11 | H | CH=CH$_2$ | Cl |
| 10.12 | H | CH=CH$_2$ | CH$_3$ |
| 10.13 | propargyl | CH=CH$_2$ | Cl |
| 10.14 | allenyl | CH=CH$_2$ | Cl |

Table 11 provides 14 compounds of formula (Ik):

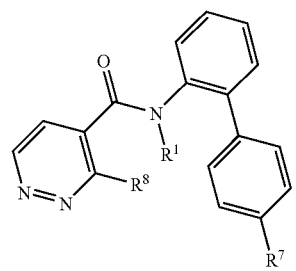
(Ik)

wherein $R^1$, $R^7$ and $R^8$ are as defined in Table 11.

TABLE 11

| Compound No. | R¹ | R⁷ | R⁸ |
|---|---|---|---|
| 11.01 | H | C≡CH | Cl |
| 11.02 | H | C≡CH | CF₃ |
| 11.03 | COMe | C≡CH | Cl |
| 11.04 | H | C≡CH | Br |
| 11.05 | COCH₂OMe | C≡CH | Cl |
| 11.06 | H | C≡CSiMe₃ | Cl |
| 11.07 | H | C≡CSiMe₃ | CF₃ |
| 11.08 | H | C≡CSiMe₃ | Br |
| 11.09 | H | CH=CH₂ | CF₃ |
| 11.10 | H | CH=CH₂ | Br |
| 11.11 | H | CH=CH₂ | Cl |
| 11.12 | H | CH=CH₂ | CH₃ |
| 11.13 | propargyl | CH=CH₂ | Cl |
| 11.14 | allenyl | CH=CH₂ | Cl |

Table 12 provides 94 compounds of formula (II) where R², R³, R⁴ and R⁵ are each hydrogen; n is 0; and R¹ and R⁷ are as defined in Table 12.

TABLE 12

| Compound No. | R¹ | R⁷ |
|---|---|---|
| 12.01 | H | C≡CH |
| 12.02 | H | C≡CSiMe₃ |
| 12.03 | H | C≡CCF₃ |
| 12.04 | H | C≡CCl |
| 12.05 | H | CH=CH₂ |
| 12.06 | H | CH=CF₂ |
| 12.07 | H | CH=CCl₂ |
| 12.08 | H | CH=CBr₂ |
| 12.09 | H | CF=CF₂ |
| 12.10 | H | CCl=CH₂ |
| 12.11 | H | CF=CHF |
| 12.12 | H | CH=CHCF₃ |
| 12.13 | H | CH=CClCF₃ |
| 12.14 | H | CH₂C≡CH |
| 12.15 | H | C≡CCMe₃ |
| 12.16 | CHO | C≡CMe |
| 12.17 | H | C≡C(cyclopropyl) |
| 12.18 | H | SiMe₃ |
| 12.19 | H | C≡CBr |
| 12.20 | H | CBr=CH₂ |
| 12.21 | H | CH=CHSiMe₃ |
| 12.22 | H | CH₂C=CSiMe₃ |
| 12.23 | H | C≡CMe |
| 12.24 | H | C≡CF |
| 12.25 | H | C≡CCF₂Cl |
| 12.26 | H | C≡CCF₂H |
| 12.27 | H | C≡CCF₂Br |
| 12.28 | H | C≡CCH₂F |
| 12.29 | H | C≡CCH(Me)F |
| 12.30 | H | C≡CC(Me)₂F |
| 12.31 | H | C≡CCH₂C(Me)₃ |
| 12.32 | H | C≡CCH(Me)₂ |
| 12.33 | H | C≡CCH₂CH(Me)₂ |
| 12.34 | H | CH₂C≡CCMe₃ |
| 12.35 | H | CF₂C≡CCMe₃ |
| 12.36 | H | CF₂C≡CMe |
| 12.37 | H | CF₂C≡CH |
| 12.38 | H | CMe₂C≡CH |
| 12.39 | H | CHFC=CH |
| 12.40 | H | CHMeC≡CH |
| 12.41 | H | CH(CF₃)C≡CH |
| 12.42 | H | C≡C(1-F-cyclopentyl) |
| 12.43 | H | C≡CCH₂OMe |
| 12.44 | H | C≡CCMe₂OMe |
| 12.45 | H | C≡CCMe₂OCOMe |
| 12.46 | H | C≡CCF₂Me |
| 12.47 | H | C≡CC(Me)=CH₂ |
| 12.48 | H | CH=CFCl |
| 12.49 | H | CH=CFBr |
| 12.50 | H | CH=CHBr |
| 12.51 | H | CH=CHF |
| 12.52 | H | CMe=CHCF₃ |

TABLE 12-continued

| Compound No. | R¹ | R⁷ |
|---|---|---|
| 12.53 | H | CH=CFCF₃ |
| 12.54 | H | CH=CBrCF₃ |
| 12.55 | H | CH=CHC₂F₅ |
| 12.56 | H | CH=CHCl |
| 12.57 | H | CH=C(CF₃)₂ |
| 12.58 | H | CMe=CFCl |
| 12.59 | H | CMe=CFBr |
| 12.60 | H | CMe=CF₂ |
| 12.61 | H | CMe=CCl₂ |
| 12.62 | H | CMe=CBr₂ |
| 12.63 | H | CMe=CFCF₃ |
| 12.64 | H | CMe=CClCF₃ |
| 12.65 | H | CCF₃=CF₂ |
| 12.66 | H | CCF₃=CCl₂ |
| 12.67 | H | CCF₃=CCl₂ |
| 12.68 | H | CCF₃=CCl₂ |
| 12.69 | H | CCF₃=CBr₂ |
| 12.70 | H | CCF₃=CH₂ |
| 12.71 | H | CCF₃=CFBr |
| 12.72 | H | CCF₃=CHF |
| 12.73 | H | CCF₃=CFCl |
| 12.74 | H | CCF₃=CHCl |
| 12.75 | H | CH=CFCF₂Cl |
| 12.76 | H | CH=CClCF₂Cl |
| 12.77 | H | CH₂CF=CF₂ |
| 12.78 | H | CF=CFBr |
| 12.79 | H | CH₂CH=CF₂ |
| 12.80 | H | CH₂CH=CCl₂ |
| 12.81 | H | CH₂CH=CBr₂ |
| 12.82 | H | CCl=CF₂ |
| 12.83 | H | C≡CCH₂SiMe₃ |
| 12.84 | H | C≡CSiMe₂CMe₃ |
| 12.85 | H | C≡CCMe₂OH |
| 12.86 | H | C≡CCH₂CH₃ |
| 12.87 | H | C≡CCF=CF₂ |
| 12.88 | H | C≡CCHFCl |
| 12.89 | H | CH=CFC₂F₅ |
| 12.90 | H | C≡CCF₂CH₂CH₃ |
| 12.91 | H | C≡CCHFCH₂CH₃ |
| 12.92 | H | C≡CCF(CF₃)₂ |
| 12.93 | H | CH=CClC₂F₅ |
| 12.94 | H | C≡CC₂F₅ |

Table 13 provides 1 compound of formula (III) where R², R³, R⁴ and R⁵ are each hydrogen; n is 0; and Hal and R⁷ are as defined in Table 13.

TABLE 13

| Compound Number | R⁷ | Hal |
|---|---|---|
| 13.01 | C≡CH | Br |

Throughout this description, temperatures are given in degrees Celsius; "NMR" means nuclear magnetic resonance spectrum; MS stands for mass spectrum; M⁺−1 or M⁺1 are signals in the mass spectrum respectively corresponding to the molecular weight minus 1 or the molecular weight plus 1; and "%" is percent by weight, unless corresponding concentrations are indicated in other units.

The following abbreviations are used throughout this description:

| | |
|---|---|
| m.p. = melting point | b.p. = boiling point. |
| s = singlet | br = broad |
| d = doublet | dd = doublet of doublets |
| t = triplet | q = quartet |
| m = multiplet | ppm = parts per million |

Table 14 shows selected melting point, selected molecular ion and selected NMR data, all with $CDCl_3$ as the solvent (unless otherwise stated; if a mixture of solvents is present, this is indicated as, for example, $(CDCl_3/d_6\text{-DMSO})$), (no attempt is made to list all characterising data in all cases) for compounds of Tables 1 to 13. Unless otherwise stated, the data relate to a cis/trans mixture of each compound.

TABLE 14

| Compound Number | $^1$H-NMR data: (ppm/multiplicity/number of Hs) or MS-data | m.p./(° C.) |
|---|---|---|
| 1.01 | | 169–170 |
| 1.03 | | 132–135 |
| 1.08 | | 147–150 |
| 1.10 | | >200 |
| 1.12 | | 195–197 |
| 1.13 | | 139–144 |
| 1.15 | | 193–194 |
| 1.16 | | 120–125 |
| 1.18 | | 207–209 |
| 1.19 | | 210–212 |
| 1.22 | | 184–187 |
| 1.24 | | 137–141 |
| 1.29 | | 197–198 |
| 1.30 | | 181–182 |
| 1.32 | | 173–176 |
| 1.33 | | 147–150 |
| 1.35 | | 167–169 |
| 1.36 | | 148–150 |
| 1.38 | | 156–157 |
| 1.39 | | 168–170 |
| 1.41 | | 212–213 |
| 1.42 | | 174–176 |
| 1.50 | | 117–124 |
| 1.53 | | 205–206 |
| 1.54 | | 194–195 |
| 1.56 | | 143–145 |
| 1.57 | | 118–121 |
| 1.59 | | 186–190 |
| 1.60 | | 137–139 |
| 1.66 | | 139–143 |
| 1.67 | 406($M^+$−1) | 193–196 |
| 1.69 | 382($M^+$−1) | 221–223 |
| 1.70 | 364($M^+$−1) | 205–208 |
| 1.77 | | 208–210 |
| 1.78 | | 202–205 |
| 1.80 | | 165–166 |
| 1.81 | | 165–169 |
| 1.85 | | 198–198.5 |
| 1.86 | | 184–184.5 |
| 1.88 | | 206–207 |
| 1.89 | | 200–201 |
| 1.193 | | 160–162 |
| 1.94 | | 205–206 |
| 1.95 | | 198–199 |
| 1.97 | | 197–198 (decomposition) |
| 1.98 | | 176–177 |
| 1.100 | | 120–121 |
| 1.101 | | 128–129 |
| 1.106 | | 155–158 |
| 1.107 | | 142–143 |
| 1.109 | | 150–153 |
| 1.110 | | 132–140 |
| 1.137 | | 132–133 |
| 1.138 | | 167–169 |
| 1.139 | | 163–165 |
| 1.141 | | 141–142.5 |
| 1.142 | | 155–156 |
| 1.144 | 1.8(s, 6); 2.1(s, 3); 3.95(s, 3) 7.2–7.6(m, 7); 7.75(br.s, 1); 8.25(d, 1) | |
| 1.145 | | 132–141 |
| 1.147 | | 149–150 |
| 1.150 | | 143–145 |
| 1.151 | | 189–194 |
| 1.152 | | 168–170 |
| 1.154 | | 197–200 |
| 1.155 | | 174–178 |
| 1.158 | | 195 |

TABLE 14-continued

| Compound Number | $^1$H-NMR data: (ppm/multiplicity/number of Hs) or MS-data | m.p./(° C.) |
|---|---|---|
| 1.166 | | 172–155 |
| 1.167 | | 145–150 |
| 1.182 | | 127–129 |
| 1.185 | | 111–114 |
| 1.194 | 2.25(s, 3); 3.9(s, 3); 6.7(t, 1); 7.2–7.5(m, 6); 7.7(s, 1); 7.72(br, 1); 8.3(d, 1) | |
| 1.212 | | 176–179 |
| 1.226 | | 152.5–153 |
| 1.227 | | 146–147 |
| 1.250 | | 159–162 |
| 1.251 | | 156–161 |
| 1.252 | | 163–165 |
| 1.254 | | 139–140 |
| 1.255 | | 187–187.5 |
| 1.257 | | 177–178 |
| 2.01 | | 145–148 |
| 2.08 | | 148–154 |
| 2.66 | | 160–165 |
| 3.01 | | 145–147 |
| 3.08 | | 103–105 |
| 3.12 | | 122–126 |
| 3.18 | | 160–165 |
| 3.29 | | 146–147 |
| 3.32 | | 125–130 |
| 3.35 | | 120–126 |
| 3.38 | | 122–127 |
| 3.41 | | 169–170 |
| 3.56 | | 132–137 |
| 3.66 | | 129–133 |
| 3.69 | | 159–163 |
| 3.97 | | 133–134 |
| 3.100 | | 127.7–129 |
| 3.109 | | 117–119 |
| 3.136 | | 140–142 |
| 3.141 | 1.55(s, 6); 2.7(s, 3); 3.4(s, 3); 7.2–7.3(m, 4); 7.4(m, 1); 7.5(d, 2); 7.55(br, 1); 8.3(d, 1) | |
| 3.146 | | 141–142 |
| 3.157 | | 145–157 |
| 3.166 | | 148–150 |
| 3.193 | | 128–132 |
| 3.211 | | 183–184 |
| 3.250 | | 140–143 |
| 9.01 | | 150–152 |
| 9.06 | | 84–86 |
| 9.15 | | 154–157 |
| 9.21 | | 185–189 |
| 9.38 | | 141–142 |
| 9.41 | | 143–145 |
| 9.50 | | 157–159 |
| 9.53 | | 133–138 |
| 9.58 | | 130–132 |
| 9.59 | | 123–125 |
| 9.62 | | 138–139 |
| 9.65 | | 164–167 |
| 9.68 | 1.8(s, 9); 4.9+5.25(m, 1); 6.15–8.5(m, 12) | |
| 9.83 | | 143–145 |
| 9.86 | | 169–170 |
| 9.89 | | 167–167.5 |
| 9.99 | | 109–111 |
| 9.118 | 1.8(s, 6); 2.1(s, 3); 7.2–7.6(m, 9), 8.1(m, 1); 8.45(m, 1) | |
| 9.132 | | 162–165 |
| 9.138 | | 172–175 |
| 9.163 | | 167–171 |
| 9.185 | | 119–120.5 |
| 9.201 | 0.0(s, 9); 1.55(s, 2); 7.0–7.3(m, 8); 79–8.0(m, 2); 8.3(m, 2) | |
| 9.203 | | 105–107 |
| 12.01 | | 111–115 |
| 12.02 | 0.05(s, 9); 6.5–6.7(d+t, 2); 6.8–7.1(t+t, 2); 7.2–7.5(m, 4) | |
| 12.03 | 262(M+H$^+$); 303(M+MeCN+H$^+$); | |
| 12.04 | | 92–98 |
| 12.06 | 3.75(br, 2); 5.35(dd, 1); 6.75–6.9(m, 2); 7.1–7.2(m, 2); 7.35–7.5(m, 4) | |

TABLE 14-continued

| Compound Number | $^1$H-NMR data: (ppm/multiplicity/number of Hs) or MS-data | m.p./(° C.) |
|---|---|---|
| 12.07 | 3.8(br, 2); 6.8(d, 1); 6.85(t, 1); 6.9(s, 1); 7.1–7.2(d+t, 2); 7.45–7.65(m, 4) | |
| 12.08 | 3.8(br, 2); 6.75–6.9(m, 2); 7.1–7.2(m, 2); 7.5–7.7(m, 5) | |
| 12.09 | 3.8(br, 2); 6.7–6.9(m, 2); 7.1–7.2(m, 2); 7.6(very narrow m, 4)<br>$^{19}$F: −99.7; −114.6; −177.3 | |
| 12.10 | 230(M+H$^+$); 371(M+MeCN+H$^+$) | |
| 12.12 | | 84–86 |
| 12.13 | 298(M+H$^+$); 339(M+MeCN+H$^+$); | |
| 12.14 | 208(M+H$^+$); 249(M+MeCN+H$^+$); | |
| 12.15 | | 66–69 |
| 12.16 | | 91–96 |
| 12.17 | 0.8–0.9(m, 4); 1.4–1.5(m, 2); 3.7(br, 2); 6.7–6.8(m, 2); 7.1–7.2(m, 2); 7.3–7.5(m, 4) | |
| 12.18 | 0.15(s, 9); 2.0–2.6(very broad, 2); 6.6–6.7(m, 2); 7.0–7.1(m, 2); 7.3–7.5(m, 4) | |
| 12.19 | 3.8(br, 2); 6.75–6.9(m, 2); 7.1–7.2(m, 2); 7.35–7.55(m, 4) | |
| 12.23 | | 108–112 |
| 12.25 | 3.75(br, 2); 6.8(m, 2); 7.1–7.25(m, 2); 7.5–7.7(m, 4)<br>$^{19}$F: −35.9 | |
| 12.26 | 3.8(br, 2); 6.4(t, 1); 6.75–6.9(m, 2); 7.1–7.25(m, 2); 7.4–7.56(m, 4); $^{19}$F: −105.7 | |
| 12.28 | | 69–71 |
| 12.29 | 1.7(d of d, 3); 3.8(br, 2); 5.5(d of quartetts, 1); 6.75–6.9(m, 2); 7.05–7.2(m, 2); 7.4–7.6(m, 4)<br>$^{19}$F: −165.6 | |
| 12.30 | 1.75(d, 6); 3.8(br, 2); 6.8(m, 2); 7.15(m, 2); 7.4–7.6(m, 4)<br>$^{19}$F: −126.0 | |
| 12.32 | 1.3(d, 6); 3.7(br, 2); 6.7–6.8(d+t, 2); 7.15(m, 2); 7.3–7.5(m, 4) | |
| 12.33 | 1.05(d, 6); 1.9(m, 1); 2.35(d, 2); 3.75(br, 2); 6.75–6.9(m, 2); 7.1–7.2(m, 2); 7.35–7.5(m, 4) | |
| 12.42 | 1.7–2.5(m, 8); 3.7(br, 2); 6.7–6.8(m, 2); 7.05–7.15(m, 2); 7.35.7.5(m, 4); 7.1–7.2(m, 2); 7.4–7.6(m, 4) | |
| 12.43 | 3.45(s, 3); 3.8(br, 2); 4.35(s, 2); 6.7–6.8(d+t, 2); 7.1–7.25(m, 2); 7.4–7.6(m, 4) | |
| 12.45 | 1.75(s, 6); 2.1(s, 3); 3.75(br, 2); 6.75–6.85(m, 2); 7.1–7.2(m, 2); 7.4–7.6(m, 4) | |
| 12.46 | 2.0(t, 3); 3.75(br, 2); 6.75–6.85(m, 2); 7.1–7.2(m, 2); 7.4–7.6(m, 4) | |
| 12.47 | 2.0(s, 3); 3.75(br, 2); 5.3(narrow m, 1); 5.4(s, 1); 6.75–6.85(m, 2); 7.1–7.2(m, 2); 7.4–7.55(m, 4) | |
| 12.48 | 3.8(br, 2); 5.85+6.45(2ds, 1); 6.7–6.9(m, 2); 7.1–7.2(m, 2); 7.4–7.65(m, 4); $^{19}$F: −71.2; −73.9 | |
| 12.49 | 4.0–4.6(br, 2); 6.0+6.7(2ds, 1); 6.75–6.9(m, 2); 7.1–7.2(m, 2); 7.4–7.65(m, 4); | |
| 12.50 | | 86–92 |
| 12.53 | | |
| 12.58 | 2.1(2s, 3); 3.8(br, 2); 6.7–6.9(m, 2); 7.1–7.2(m, 2); 7.35–7.5(m, 2); $^{19}$F: −80.1; −81.3 | |
| 12.59 | 2.1(2s, 3); 3.8(br, 2); 6.7–6.9(m, 2); 7.1–7.2(m, 2); 7.35–7.5(m, 2); $^{19}$F: −74.2; −74.6 | |
| 12.62 | | 120–129 |
| 12.70 | 3.75(br, 2); 5.8(narrow m, 1); 5.95(narrow m, 1); 6.75–6.9(m, 2); 7.1–7.2(m, 2); 7.4–7.55(m, 4) | |
| 12.75 | | 67–68.5 |
| 12.83 | 0.0(s, 9); 1.6(s, 2); 6.6(d, 1); 6.65(t, 1); 7.0(m, 2); 7.2–7.4(m, 4) | |
| 12.84 | 0.0(s, 6); 0.8(s, 9); 4.25(very broad, 2); 6.65–6.75(m, 2); 6.9–7.05(m, 2); 7.2–7.4(m, 4) | |
| 12.85 | 252(M+H$^+$) | |
| 15.25 | | 131–134 |
| 15.26 | | Amorphous |
| 15.28 | 1.3(s, 9); 7.2–7.5(m, 10); 8.1(m, 2); 8.45(m, 2) | |
| 16.7 | | 63–64 |

Table 15 provides 48 compounds of formulas 1(m) where R, X and Het are as defined in Table 15.

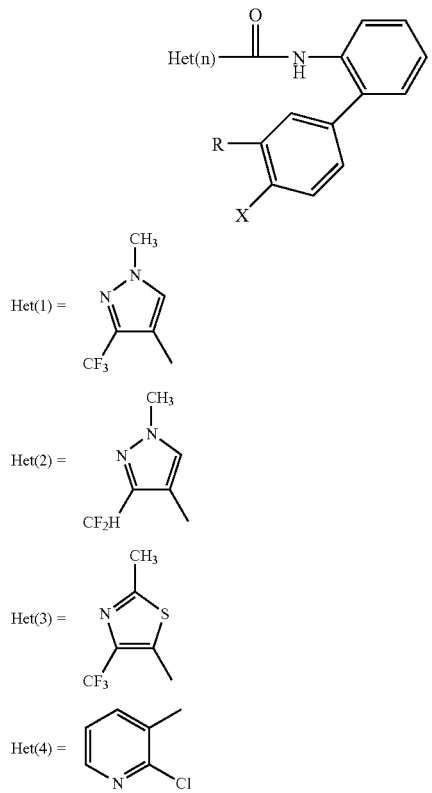

TABLE 15

| Compound No. | X | R | Het |
|---|---|---|---|
| 15.1 | H | C≡CH | Het(1) |
| 15.2 | H | C≡CH | Het(2) |
| 15.3 | H | C≡CH | Het(3) |
| 15.4 | H | C≡CH | Het(4) |
| 15.5 | Cl | C≡CH | Het(1) |
| 15.6 | Cl | C≡CH | Het(2) |
| 15.7 | Cl | C≡CH | Het(3) |
| 15.8 | Cl | C≡CH | Het(4) |
| 15.9 | F | C≡CH | Het(1) |
| 15.10 | F | C≡CH | Het(2) |
| 15.11 | F | C≡CH | Het(3) |
| 15.12 | F | C≡CH | Het(4) |
| 15.13 | H | C≡CMe | Het(1) |
| 15.14 | H | C≡CMe | Het(2) |
| 15.15 | H | C≡CMe | Het(3) |
| 15.16 | H | C≡CMe | Het(4) |
| 15.17 | F | C≡CMe | Het(1) |
| 15.18 | F | C≡CMe | Het(2) |
| 15.19 | F | C≡CMe | Het(3) |
| 15.20 | F | C≡CMe | Het(4) |
| 15.21 | Cl | C≡CMe | Het(1) |
| 15.22 | Cl | C≡CMe | Het(2) |
| 15.23 | Cl | C≡CMe | Het(3) |
| 15.24 | Cl | C≡CMe | Het(4) |
| 15.25 | H | C≡CCMe$_3$ | Het(1) |
| 15.26 | H | C≡CCMe$_3$ | Het(2) |
| 15.27 | H | C≡CCMe$_3$ | Het(3) |
| 15.28 | H | C≡CCMe$_3$ | Het(4) |
| 15.29 | Cl | C≡CCMe$_3$ | Het(1) |
| 15.30 | Cl | C≡CCMe$_3$ | Het(2) |
| 15.31 | Cl | C≡CCMe$_3$ | Het(3) |
| 15.32 | Cl | C≡CCMe$_3$ | Het(4) |

TABLE 15-continued

| Compound No. | X | R | Het |
|---|---|---|---|
| 15.33 | F | C≡CCMe$_3$ | Het(1) |
| 15.34 | F | C≡CCMe$_3$ | Het(2) |
| 15.35 | F | C≡CCMe$_3$ | Het(3) |
| 15.36 | F | C≡CCMe$_3$ | Het(4) |
| 15.37 | H | CH=CClCF$_3$ | Het(1) |
| 15.38 | H | CH=CClCF$_3$ | Het(2) |
| 15.39 | H | CH=CClCF$_3$ | Het(3) |
| 15.40 | H | CH=CClCF$_3$ | Het(4) |
| 15.41 | Cl | CH=CClCF$_3$ | Het(1) |
| 15.42 | Cl | CH=CClCF$_3$ | Het(2) |
| 15.43 | Cl | CH=CClCF$_3$ | Het(3) |
| 15.44 | Cl | CH=CClCF$_3$ | Het(4) |
| 15.45 | F | CH=CClCF$_3$ | Het(1) |
| 15.46 | F | CH=CClCF$_3$ | Het(2) |
| 15.47 | F | CH=CClCF$_3$ | Het(3) |
| 15.48 | F | CH=CClCF$_3$ | Het(4) |

Table 16 provides 12 compounds of formulas II(m) where R and X are as defined in Table 16:

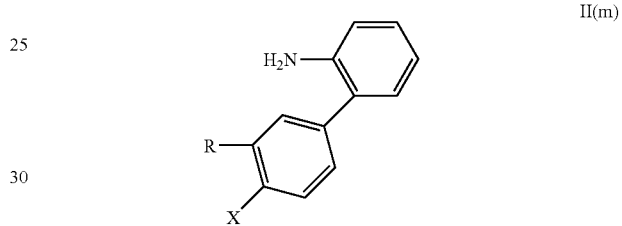

TABLE 16

| Compound No. | X | R |
|---|---|---|
| 16.1 | H | C≡CH |
| 16.2 | Cl | C≡CH |
| 16.3 | F | C≡CH |
| 16.4 | H | C≡CMe |
| 16.5 | F | C≡CMe |
| 16.6 | Cl | C≡CMe |
| 16.7 | H | C≡CCMe$_3$ |
| 16.8 | Cl | C≡CCMe$_3$ |
| 16.9 | F | C≡CCMe$_3$ |
| 16.10 | H | CH=CClCF$_3$ |
| 16.11 | Cl | CH=CClCF$_3$ |
| 16.12 | F | CH=CClCF$_3$ |

The compounds according to the present invention may be prepared according to the following reaction schemes, in which, unless otherwise stated, the definition of each variable is as defined above for a compound of formula (I).

There are a number of alternative methods for preparing a compound of formula (I).

Method A

A compound of formula (I) may be prepared by reacting a compound of formula (II) with a compound of formula Het-C(=O)OR' (where R' is $C_{1-5}$ alkyl) in the presence of strong base [for example NaH or sodium hexamethyldisilazane], in a dry polar solvent [preferably THF] and at a temperature between −10° C. and the boiling point of the solvent [preferably at ambient temperature]. The article by J. Wang et al, Synlett 2001, 1485 provides details of analogous preparations.

Method B

A compound of formula (I) may be prepared by reacting a compound of formula (II) with a compound of formula Het-C(=O)R" [where R" is OH or a leaving group, such as Cl, Br, F or OC(=O)$C_{1-4}$ alkyl] in an inert organic solvent [such as ethylacetate, dichloromethane, dioxane or DMF] and at a temperature between −10° C. and the boiling point of the solvent [preferably at ambient temperature]. If R" is OH, the reaction is carried out in the presence of an activating agent [for example BOP-Cl] and two equivalents of a base [such as a tertiary amine, an inorganic carbonate or a hydrogen carbonate]. Alternatively, if R" is a leaving group, the reaction is carried out in the presence of at least one equivalent of base [such as pyridine, a tertiary amine, an inorganic carbonate or a hydrogen carbonate].

Method C

A compound of formula (I) [where $R^1$ is as defined above but is not hydrogen] may be prepared by reacting a compound of formula (I) [where $R^1$ is hydrogen] with a compound of formula $R^1$-$L^1$ [where $R^1$ is as defined above but is not hydrogen; and $L^1$ is a leaving group such as Cl, Br, I, a sulfonate (for example a mesylate or a tosylate) or OC(O) $C_{1-4}$ alkyl] in a solvent [such as a halogenated solvent (for example dichloromethane), an ether, ethylacetate, DMF or even water (as a biphasic mixture, optionally in the presence of a phase transfer catalyst such as tetrabutylammonium hydrogensulfate)] and in the presence of a base [such as a tertiary amine, an alkali carbonate, an alkali bicarbonate, an alkali hydroxide or NaH; though if $L^1$ is O(CO) $C_{1-4}$ alkyl then simply heating without base is possible].

Method D

A compound of formula (I) may be prepared by reacting a compound of formula (Im) [where Hal is preferably bromo or iodo] with a compound of formula Het-C(=O)$NH_2$ in the presence of a Cu(I) compound and an aprotic solvent [such as a cyclic ether, for example dioxane] at an elevated temperature and preferably at reflux. The preferred conditions are CuI used at 2% to 100% mole/mole, relative to the compound of formula (III), in the presence of a 1,2-diamine as a ligand-forming substance (such as 1,2-diamino cyclohexane or ethylene diamnine) and at least 1 equivalent of a base (such as an alkali carbonate or an alkali phosphate. The article by A. Klapars et al. J. Am. Chem. Soc. 123, 7727 (2001) provides details of analogous preparations.

Method E

A compound of formula (I) may be prepared by conversion of a compound of formula (IV)

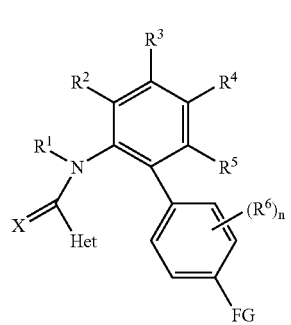

(IV)

[where FG is a functional group which is convertible to $R^7$ in one or more synthetic steps]. Functional group interconversions are standard procedures for a person skilled in the art. There are many methods described in the literature, which can be used as such or with modifications according to the functionalities present; Table A gives literature references (some of which also cite further appropriate references) which are specifically relevant to the preparation of a compound of formula (I) by the interconversion of FG to $R^7$. It is apparent to the person skilled in the art that the literature examples given in Table A are not necessarily limited to the preparation of the specifically mentioned $R^7$ but can be also applied by analogy to the preparation of other structurally related $R^7$

TABLE A

| Reference | FG | $R^7$ |
|---|---|---|
| Synthesis 2001, 2081 | CHO | CH=$CBr_2$ |
| Tetrahedron 58, 1491 (2002) | | CH=CHBr |
| | | C≡CBr |
| Russ. Chem. Bull. 50(6), 1047 (2001) | CHO | CH=$CCl_2$ |
| Tetrahedron 57, 7519 (2001) | CHO | CH=$CClCF_3$ |
| | | CH=$CFCF_2Cl$ |
| Bull. Chem. Soc. Jpn. 73, 1691 (2000) | CHO | CF=CBrF |
| Bull. Chem. Soc. Jpn. 71, 2903 (1998-) | | |
| J. Chem. Soc. Perkin 1 2002, 883 | $COCH_3$ | $C(CH_3)$=CHBr |
| | | $C(CH_3)$=$CCl_2$ |
| J. Fluorine Chem. 1, 381 (1972) | $COCH_3$ | $C(CH_3)$=$CBr_2$ |
| J. Fluorine Chem. 23, 339 (1983) | $COCF_3$ | $C(CH_3)$=CFBr |
| | | $C(CH_3)$=CFCl |
| | | $C(CF_3)$=CFBr |
| | | $C(CF_3)$=CFCl |
| | | $C(CF_3)$=$CF_2$ |
| Tetrahedron Letters 41, 8045 (2000) | Hal | CF=CHF |
| J. Org. Chem. 62, 9217 (1997) | | |
| Tetrahedron Letters 37, 8799 (1996) | Hal | CH=$CF_2$ |
| JP 09278688 | Hal | CF=$CF_2$ |
| J. Fluorine Chem. 31, 115 (1986) | | |
| Zh. Org. Khim. 25, 1451 (1989) | Hal | CF=CFCl |
| J. Org. Chem. 53, 2714 (1988) | Hal | CF=$CFCF_3$ |
| J. Org. Chem. 56, 7336 (1991) | Hal | $C(CF_3)$=$CH_2$ |
| Tetrahedron Letters 42, 4083 (2001) | | |
| Ukr. Khim. Zh. 32, 996 (1966) | $CHBrCH_2CF_3$ | CH=$CHCF_3$ |
| Bull. Chem. Soc. Jap. 62, 1352 | CH=$CClCF_3$ | C≡$CCF_3$ |
| | CH=$CFCF_2Cl$ | C≡$CCF_2Cl$ |
| J. Org. Chem. 54, 5856 (1989) | Hal or triflate | C≡CH |
| J. Am. Chem. Soc. 109, 2138 (1987) | | C≡$CSiMe_3$ |
| Tetrahedron 45, 6511 (1989) | | C≡$CCH_3$ |
| J. Orgmet. Chem. 549, 127 (1997) | | C≡$CCMe_3$ |
| Tetrahedron 56, 10075 (2000) | | C≡$CCH_2OH$ |
| Tetrahedron Asymmetry 6, 245 (1995) | | C≡CCHMeOH |
| | | C≡$CCMe_2OH$ |
| | | C≡CCHO |
| | | C≡CC(O)Me |
| J. Org. Chem. 32, 1674 (1967) | C≡$CCH_3$ | $CH_2C$≡CH |
| Synth. Comm. 1989, 561 | CHO | C≡CH |
| | $CH_2CHO$ | $CH_2C$≡CH |
| WO 01 092563 | CHO | CH=$CH_2$ |
| J. Am. Chem. Soc. 123, 4155 (2001) | Hal or triflate | CH=$CH_2$ |
| Org. Lett. 2, 3703 (2000) | | |
| J. Org. Chem. 57, 3558 (1992) | | |
| Synthesis 2001, 893 | | |
| GB 2 183 639 | C≡CH | CH=$CH_2$ |
| Synthesis 1996, 1494 | CHO | C≡CCl |
| J. Org. Chem. 49, 294 (1984) | | C≡CH |
| | | C≡CBr |
| US 6 159956 | $CH_2Br$ | $CH_2CF$=$CF_2$ |
| Liebigs Ann. Chem. 1995, 2027 | $CH_2Br$ | CH=$C(CF_3)_2$ |
| J. Am. Chem. Soc. 123, 4155 (2001) | $CH_2Br$ | $CH_2C$≡$CSiMe_3$ |
| Inorg. Chim. Acta 296, 37 (1999) | Hal | $CH_2C$≡$CMe_3$ |

TABLE A-continued

| Reference | FG | R[7] |
|---|---|---|
| J. Fluorine Chem. 111, 185 (2001) | CH=CHBr | CH=CHCF$_3$ |
| J. Chem. Soc. Perkin I 1988, 921 | CH=CFBr | CH=CFCF$_3$ |
|  | CH=CBr$_2$ | CH=C(CF$_3$)$_2$ |
| DE 4417441 | C≡CCH$_2$OH | C≡CCH$_2$F |
| U.S. Pat. No. 3976691 | C≡CCHMeOH | C≡CCHMeF |
| J. Org. Chem. 64, 7048 (1999) | C≡CCMe$_2$OH | C≡CCMe$_2$F |
|  | C≡CCHO | C≡CCHF$_2$ |
|  | C≡CC(O)Me | C≡CCF$_2$Me |
| J. Chem. Soc. Perkin I 1994, 725 | C≡CCH$_2$OH | C≡CCH$_2$CF$_3$ |
| Synthesis 1997, 1489 | C≡CH | C≡CCF$_2$CF$_3$ |
| Angew. Chem. Int. Ed. 39, 2481 (2000) |  | CH=CHCF$_2$CF$_3$ |
| J. Org. Chem. 47, 2255 (1982) |  |  |
| J. Fluorine. Chem. 113, 55 (2002) |  |  |
| J. Fluorine. Chem. 64, 61(1993) | C≡CH | C≡CCHFCl |
| J. Am. Chem. Soc. 109, 3492 (1987) |  | C≡CCF$_2$Br |
| J. Am. Chem. Soc. 107, 5186 (1985) | CH=CHBr | CH=CHCF$_2$CF$_3$ |

There are a number of alternative methods for preparing a compound of formula (II), (III) or (IV).

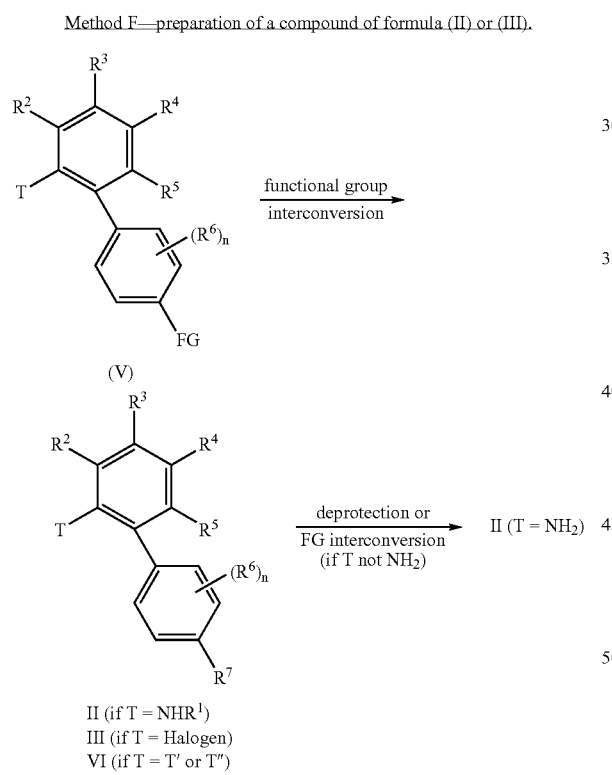

A compound of formula (II), (III) or (VI) may be prepared, by functional group interconversion, from a compound of formula (V) [where FG is as defined above for a compound of formula (IV) and T is either halogen, amino, NHR$^1$, a protected amino group T' (for example a carbamate, an amide, a cyclic imide, an N-alkyl-, N-alkenyl-, N-benzyl-, N-diphenylmethyl- or N-trityl-derivative, an imine derivative or an N-silyl- or N-disilyl-derivative) or a group T" (that is, a group which may be converted to NH$_2$ or NHR$^1$ by applying synthetic methodology described in the literature; T" being preferably azido, nitro, halogen, triflate, CONH$_2$, COOH, COCl or NCO)]. Starting from a compound of formula (V) the functional group FG may be converted to R$^7$ by applying a method analogous to method E above. This conversion leads directly to a compound of formula (II) [when T is NHR$_1$], to a compound of formula (III) [when T is halogen (preferably chloro, bromo or iodo)] or to a compound of formula (VI) [when T is T' or T"].

In a second step a compound of formula (VI) or (II) [when R$^1$ is other than H] can be converted to a compound of formula (II) [where R$^1$ is H] by either applying the methods [that is, deprotection or conversion of T" to NH$_2$] as generically described above.

Examples of versatile values for T' plus methods for deprotection are given in T. W. Green and P. Wuts, Protective Groups in Organic Synthesis, 3$^{rd}$ edition (John Wiley & Sons 1999), Chapter 7.

Compilations of useful values for T" plus literature to convert T" into NH$_2$, T' or NHR$^1$ can be found in M. B. Smith, Compendium of Organic Synthetic Methods, Vols. 1-10, Chapter 7 (Wiley, Vol. 10: 2002).

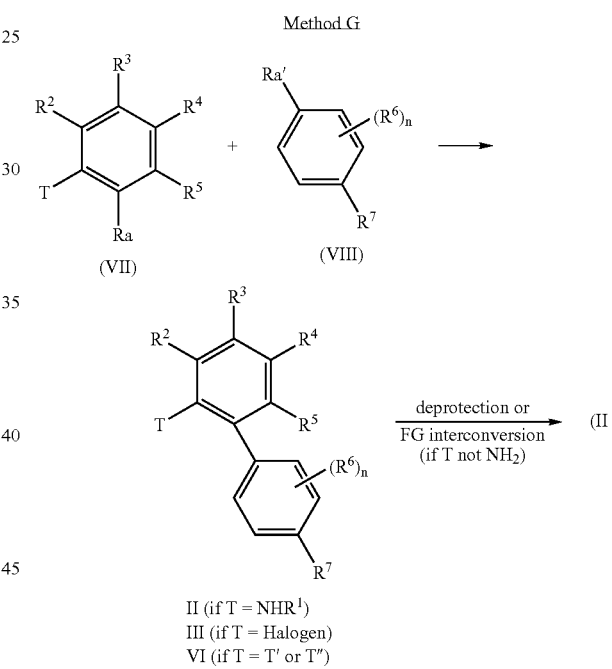

A compound of formula (II), (III) or (VI) may be prepared by a coupling reaction between a compound of formula (VII) and a compound of formula (VIII) [where Ra and Ra' are each, independently, halogen (preferably Cl, Br or I), triflate or a metal-containing functionality containing, for example, B, Sn, Mg, Zn or Cu as the metal; examples are B(OH)$_2$, esters of boronic acid (preferably esters derived from 1,2- or 1,3-diols), trialkyltin (preferably Sn(CH$_3$)$_3$ or Sn(nBu)$_3$), a halogen salt of Mg, a halogen salt of Zn or Cu. If either Ra or Ra' is a metal containing functionality, the other substituent must be halogen or triflate.

Such coupling reactions are widely known in the literature. Especially suitable are the Pd(0), Ni(0), or copper catalysed couplings which are well known to the person skilled in the art as Stille coupling, Suzuki coupling, Negishi coupling or Ullmann reaction. A comprehensive review of these reactions can be found in Metal-Catalysed Cross-Coupling Reactions; F. Diederich and P. Stang (eds.); Wiley-VCH; Weinheim 1998.

In a second step a compound of formula (VI) or (II) [when $R^1$ is other than H] can be converted to a compound of formula (II) [where $R^1$ is H] by either applying the methods [that is, deprotection or conversion of T" to $NH_2$] as generically described above.

Surprisingly, it has now been found that the novel compounds of formula (I) have, for practical purposes, a very advantageous spectrum of activities for protecting plants against diseases that are caused by fungi as well as by bacteria and viruses.

The compounds of formula (I) can be used in the agricultural sector and related fields of use as active ingredients for controlling plant pests. The novel compounds are distinguished by excellent activity at low rates of application, by being well tolerated by plants and by being environmentally safe. They have very useful curative, preventive and systemic properties and are used for protecting numerous cultivated plants. The compounds of formula I can be used to inhibit or destroy the pests that occur on plants or parts of plants (fruit, blossoms, leaves, stems, tubers, roots) of different crops of useful plants, while at the same time protecting also those parts of the plants that grow later e.g. from phytopathogenic microorganisms.

It is also possible to use compounds of formula (I) as dressing agents for the treatment of plant propagation material, in particular of seeds (fruit, tubers, grains) and plant cuttings (e.g. rice), for the protection against fungal infections as well as against phytopathogenic fungi occurring in the soil.

Furthermore the compounds according to present invention may be used for controlling fungi in related areas, for example in the protection of technical materials, including wood and wood related technical products, in food storage, in hygiene management, etc.

The compounds of formula (I) are, for example, effective against the phytopathogenic fungi of the following classes: Fungi imperfecti (e.g. *Botrytis, Pyricularia, Helminthosporium, Fusarium, Septoria, Cercospora* and *Alternaria*) and *Basidiomycetes* (e.g. *Rhizoctonia, Hemileia, Puccinia*). Additionally, they are also effective against the Ascomycetes classes (e.g. *Venturia* and *Erysiphe, Podosphaera, Monilinia, Uncinula*) and of the Oomycetes classes (e.g. *Phytophthora, Pythium, Plasmopara*). Outstanding activity has been observed against powdery mildew (*Erysiphe* spp.) and rust (*Puccinia* spp.). Furthermore, the novel compounds of formula I are effective against phytopathogenic bacteria and viruses (e.g. against *Xanthomonas* spp, *Pseudomonas* spp, *Erwinia amylovora* as well as against the tobacco mosaic virus).

Within the scope of present invention, target crops to be protected typically comprise the following species of plants: cereal (wheat, barley, rye, oat, rice, maize, sorghum and related species); beet (sugar beet and fodder beet); pomes, drupes and soft fruit (apples, pears, plums, peaches, almonds, cherries, strawberries, raspberries and blackberries); leguminous plants (beans, lentils, peas, soybeans); oil plants (rape, mustard, poppy, olives, sunflowers, coconut, castor oil plants, cocoa beans, groundnuts); cucumber plants (pumpkins, cucumbers, melons); fibre plants (cotton, flax, hemp, jute); citrus fruit (oranges, lemons, grapefruit, mandarins); vegetables (spinach, lettuce, asparagus, cabbages, carrots, onions, tomatoes, potatoes, paprika); lauraceae (avocado, cinnamomum, camphor) or plants such as tobacco, nuts, coffee, eggplants, sugar cane, tea, pepper, vines, hops, bananas and natural rubber plants, as well as ornamentals.

The compounds of formula (I) are used in unmodified form or, preferably, together with the adjuvants conventionally employed in the art of formulation. To this end they are conveniently formulated in known manner to emulsifiable concentrates, coatable pastes, directly sprayable or dilutable solutions, dilute emulsions, wettable powders, soluble powders, dusts, granulates, and also encapsulations e.g. in polymeric substances. As with the type of the compositions, the methods of application, such as spraying, atomising, dusting, scattering, coating or pouring, are chosen in accordance with the intended objectives and the prevailing circumstances. The compositions may also contain further adjuvants such as stabilizers, antifoams, viscosity regulators, binders or tackifiers as well as fertilizers, micronutrient donors or other formulations for obtaining special effects.

Suitable carriers and adjuvants can be solid or liquid and are substances useful in formulation technology, e.g. natural or regenerated mineral substances, solvents, dispersants, wetting agents, tackifiers, thickeners, binders or fertilizers. Such carriers are for example described in WO 97/33890.

The compounds of formula (I) are normally used in the form of compositions and can be applied to the crop area or plant to be treated, simultaneously or in succession with further compounds. These further compounds can be e.g. fertilizers or micronutrient donors or other preparations which influence the growth of plants. They can also be selective herbicides as well as insecticides, fungicides, bactericides, nematicides, molluscicides or mixtures of several of these preparations, if desired together with further carriers, surfactants or application promoting adjuvants customarily employed in the art of formulation.

The compounds of formula (I) can be mixed with other fungicides, resulting in some cases in unexpected synergistic activities. Mixing components which are particularly preferred are azoles, such as azaconazole, BAY 14120, bitertanol, bromuconazole, cyproconazole, difenoconazole, diniconazole, epoxiconazole, fenbuconazole, fluquinconazole, flusilazole, flutriafol, hexaconazole, imazalil, imibenconazole, ipconazole, metconazole, myclobutanil, pefurazoate, penconazole, pyrifenox, prochloraz, propiconazole, simeconazole, tebuconazole, tetraconazole, triadimefon, triadimenol, triflumizole, triticonazole; pyrimidinyl carbinole, such as ancymidol, fenarimol, nuarimol; 2-amino-pyrimidines, such as bupirimate, dimethirimol, ethirimol; morpholines, such as dodemorph, fenpropidine, fenpropimorph, spiroxamine, tridemorph; anilinopyrimidines, such as cyprodinil, mepanipyrim, pyrimethanil; pyrroles, such as fenpiclonil, fludioxonil; phenylamides, such as benalaxyl, furalaxyl, metalaxyl, R-metalaxyl, ofurace, oxadixyl; benzimidazoles, such as benomyl, carbendazim, debacarb, fuberidazole, thiabendazole; dicarboximides, such as chlozolinate, dichlozoline, iprodione, myclozoline, procymidone, vinclozoline; carboxamides, such as carboxin, fenfuram, flutolanil, mepronil, oxycarboxin, thifluzamide; guanidines, such as guazatine, dodine, iminoctadine; strobilurines, such as azoxystrobin, kresoxim-methyl, metominostrobin, SSF-129, trifloxystrobin, picoxystrobin, BAS 500F (proposed name pyraclostrobin), BAS 520; dithiocarbamates, such as ferbam, mancozeb, maneb, metiram, propineb, thiram, zineb, ziram; N-halomethylthiotetrahydrophthalimides, such as captafol, captan, dichlofluanid, fluoromides, folpet, tolyfluanid; Cu-compounds, such as Bordeaux mixture, copper hydroxide, copper oxychloride, copper sulfate, cuprous oxide, mancopper, oxine-copper;

nitrophenol-derivatives, such as dinocap, nitrothal-isopropyl; organo-p-derivatives, such as edifenphos, iprobenphos, isoprothiolane, phosdiphen, pyrazophos, tolclofos-methyl; various others, such as acibenzolar-S-methyl, anilazine, benthiavalicarb, blasticidin-S, chinomethionate, chloroneb, chlorothalonil, cyflufenamid, cymoxanil, dichlone, diclomezine, dicloran, diethofencarb, dimethomorph, SYP-LI90 (proposed name: flumorph), dithianon, ethaboxam, etridiazole, famoxadone, fenamidone, fenoxanil, fentin, ferimzone, fluazinam, flusulfamide, fenhexamid, fosetyl-aluminium, hymexazol, iprovalicarb, IKF-916 (cyazofamid), kasugamycin, methasulfocarb, metrafenone, nicobifen, pencycuron, phthalide, polyoxins, probenazole, propamocarb, pyroquilon, quinoxyfen, quintozene, sulfur, triazoxide, tricyclazole, triforine, validamycin, zoxamide (RH7281).

A preferred method of applying a compound of formula (I), or an agrochemical composition which contains at least one of said compounds, is foliar application. The frequency of application and the rate of application will depend on the risk of infestation by the corresponding pathogen. However, the compounds of formula I can also penetrate the plant through the roots via the soil (systemic action) by drenching the locus of the plant with a liquid formulation, or by applying the compounds in solid form to the soil, e.g. in granular form (soil application). In crops of water rice such granulates can be applied to the flooded rice field. The compounds of formula I may also be applied to seeds (coating) by impregnating the seeds or tubers either with a liquid formulation of the fungicide or coating them with a solid formulation.

A formulation [that is, a composition containing the compound of formula (I)] and, if desired, a solid or liquid adjuvant, is prepared in a known manner, typically by intimately mixing and/or grinding the compound with extenders, for example solvents, solid carriers and, optionally, surface active compounds (surfactants).

The agrochemical formulations will usually contain from 0.1 to 99% by weight, preferably from 0.1 to 95% by weight, of the compound of formula I, 99.9 to 1% by weight, preferably 99.8 to 5% by weight, of a solid or liquid adjuvant, and from 0 to 25% by weight, preferably from 0.1 to 25% by weight, of a surfactant.

Advantageous rates of application are normally from 5 g to 2 kg of active ingredient (a.i.) per hectare (ha), preferably from 10 g to 1 kg a.i./ha, most preferably from 20 g to 600 g a.i./ha. When used as seed drenching agent, convenient dosages are from 10 mg to 1 g of active substance per kg of seeds.

Whereas it is preferred to formulate commercial products as concentrates, the end user will normally use dilute formulations.

The following non-limiting Examples illustrate the above-described invention in more detail.

EXAMPLE 1

This Example illustrates the preparation of Compound No. 1.01.

2-Amino-4'-ethinyl-biphenyl (0.30 g) and 1-methyl-3-trifluoromethyl-4-chlorocarbonyl-pyrazol (0.33 g) were combined in THF under cooling with ice and then pyridine (0.12 ml) was added. After warming to ambient temperature the suspension was stirred for 3.5 hours, poured into water and extracted twice with ethylacetate. Separation of the organic phase, drying with sodium sulfate and evaporation of the solvent and chromatographic purification on silica gel (solvent: hexane:ethylacetate 2:1) yielded 0.4 g (70.2%) of Compound No. 1.01.

EXAMPLE 2

This Example illustrates the preparation of Compound No. 2.01.

To 1-methyl-3-trifluoromethyl-4-pyrrol carboxylic acid (0.22 g) dissolved in 10 ml dichloromethane were added triethylamine (0.32 ml) and 2-amino-4'-trimethylsilylethinyl-biphenyl (0.3 g) and finally, under cooling with ice, bis(2-oxo-3-oxazolidinyl) chlorophosphinic acid (0.29 g). After stirring for 18 hours the solvents were removed under reduced pressure and the residue was taken up with ethylacetate. Washing with water and brine, drying with sodiumsulfate and evaporation of the solvent yielded 0.45 g of a yellow oil which was chromatographed on silica gel (eluent: hexane:ethylacetate 2:1) to yield 0.13 g (26%) of Compound No. 2.01.

EXAMPLE 3

This Example illustrates the preparation of Compound No. 1.72.

To NaH (46 mg) in 5 ml dry THF at 0-5° C. was added 2-N-formylamino-4'-(propin-1-yl)-biphe (0.3 g) in 10 ml dry THF. The reaction was kept at this temperature for 1 hour and afterwards 1-methyl-3-trifluoromethyl-4-chlorocarbonyl-pyrazol (0.372 g) was added. The resultant suspension was stirred at room temperature overnight, poured into brine and extracted with ethylacetate. The solvent was evaporated and the the residue was taken into methanol and sodiummethylate (10 mg) was added. After 30 minutes the mixture was neutralised with diluted HCl, extracted with ethylacetate and washed until neutral. Chromatographic purification on silica gel (eluent: ethylacetate:hexane 1:2) and recrystallisation from toluene:hexane (4:1) yielded 0.169 g of Compound No. 1.72.

EXAMPLE 4

This Example illustrates the preparation of 2- amino4'-(trimethylsilyl)ethinyl-biphenyl (Compound No.12.02) and 2-amino-4'-ethinyl-biphenyl (Compound No.12.01) using a preparation according to Method F above.

To 2.5 g 2-amino-4'-bromo-biphenyl (WO0264562) in piperidine (25 ml) under nitrogen were added in sequence CuI (0.1 g), bis(triphenylphosphino)palladium dichloride (0.35 g) and trimethylsilylacetylene (2.8 ml). The mixture was stirred for 22 hours at room temperature and for a further 26 hours at 60° C. After cooling the reaction mixture was diluted with water and extracted with ethylacetate. Then the organic phase was washed with water and dried over sodium sulfate. After evaporation of the solvents in vacuum the mixture was chromatographed on silica gel (hexane: ethylacetate 9:1) to yield 2- amino-4'-(trimethylsilyl)ethinyl-biphenyl (2 g) (Compound No.12.02).

1.4 g of this compound was dissolved in methanol (40 ml) and potassium carbonate (0.9 g) was added with cooling. The resultant suspension was stirred for 2 hours, poured on ice-water and the precipitate formed was filtered off, washed thoroughly with water and dried to obtain 2-amino-4'-ethinyl-biphenyl (0.9 g) (Compound No.12.01) as light tan crystals.

EXAMPLE 5

This Example illustrates the preparation of 2-N-fonnylamino-4'-(propin-1-yl)-biphenyl (Compound No.12.16)

N-formylamino-4'bromo-biphenyl (3.5 g) (J. Chem. Soc. 1957, 4), tributyltin(propinyl-1) (5 g) (commercial from Aldrich), tetralis(triphenylphosphine)palladium (0.37 g) were combined in toluene (200 ml) under nitrogen and heated to reflux for 16 hours. The resultant dark mixture was diluted with water and extracted with ethyl acetate. The organic phase was washed with water, dried over sodium sulfate and the solvents were evaporated at reduced pressure. The residue was taken into acetonitrile and washed repeatedly with hexane. After removal of the acetonitrile at reduced pressure and chromatography of the residue with silicagel (eluent:hexane ethylacetate 2:1) 2-N-formylamino-4'-(propin-1-yl)-biphenyl (Compound No.12.16) (1.57 g) was obtained as a light yellow powder.

EXAMPLE 6

This Example illustrates the preparation of 2-amino-4'(2,2-dichloro)ethylene-biphenyl (Compound No. 12.07) and 2-amino-4'(chloroethinyl)-biphenyl (Compound No 12.04.

a) Preparation of 2-nitro4'(2,2-dichloro)ethylene-biphenyl.

To 2-nitro-4'formyl-biphenyl (2 g) (WO 95 03290) (prepared by Pd-catalysed coupling of 2-bromonnitrobenzene with 4-formyl-phenyl-boronic acid) in ethanol (70 ml) was added hydrazine hydrate (95%) (1.32 g) and the resultant mixture was then refluxed for 5 hours. The solvent was evaporated to dryness under reduced pressure, the residue was suspended in DMSO (30 ml) and then ammonia (25%) (3 ml), and freshly prepared CuCd (80 mg) were sequentially added and finally tetrachlorometane (3.8 g) was dropped in under cooling with water. The mixture was stirred at room temperature for 24 hours and the resultant green suspension was poured into water, extracted with dichloromethane, washed with water and dried over sodium sulfate. Evaporation of the solvent and chromatography of the residue over silicagel (eluent:hexane:ethylacetate 4:1) yielded 2-nitro-4'(2,2-dichloro)ethylene-biphenyl (0.8 g), m.p. 58-59° C.

b) Preparation of 2-amino-4'(2,2-dichloro)ethylene-biphenyl.

2-Nitro-4'(2,2-dichloro)ethylene-biphenyl (0.76 g) from step (a) was dissolved in 50% ethanol (30 ml) and heated to reflux. Then 2N HCl (0.3 ml) in 50% ethanol (10 ml) was added dropwise. The reaction mixture was held at reflux for 4 hours, cooled to room temperature and filtered. The filtrate was-neutralised with sodium bicarbonate, extracted twice with ethylacetate and the organic phase was dried over sodium sulfate. Evaporation of the solvent under reduced pressure yielded 2-amino-4'(2,2-dichloro)ethylene-biphenyl (0.62 g) (Compound No. 12.07).

c) 2-Amino-4'(2,2-dichloro)ethylene-biphenyl (3 g) was dissolved in 150 ml dimethyl sulfoxide in which 0.9 g KOH (85%, powder) has been suspended. The mixture was stirred over night at room temperature, diluted with excess of water and extracted twice with ethyl acetate and the organic phase was dried over sodium sulfate. Evaporation of the solvent under reduced pressure and chromatography of the residue over silicagel (eluent:hexane:ethylacetate 4:1) yielded 2.5 g 2-amino-4'(2,2-dichloro)ethylene-biphenyl as a tan coloured solid.

EXAMPLE 7

This Example illustrates the preparation of Compound Number 12.18.

Step A: 2-Nitro-(4'-trimethylsilyl)-biphenyl

2-Bromo-nitrobenzene (0.86 g), 4-(trimethylsilyl)phenyl-boronic acid (1 g) and bis-(triphenylphosphine)-palladium-dich (0.3 g) were dissolved in dimethoxyetane (35 ml) and then a solution of sodium bicarbonate (1.3 g) dissoved in water (5 ml) was added dropwise. The mixture was heated for 3 hours (80° C. bath temperature), cooled to room temperature, poured on to ethyl acetate:water:1:1 (300 ml) and suction filtered. The organic phase was separated, dried over sodium sulfate and the solvent was removed. The resultant residue (1.58 g of a dark oil) was chromatographed on silica gel (eluent:hexane:ethyl acetate:4:1) to yield a yellow oil (1.12 g). This compound was used in Step B.

Step B: 2-Amino-(4'-trimethylsilyl)-biphenyl [Compound 12.18]

The compound obtainedfrom step A above (0.955 g) and ammonium formiate (1.86 g) were dissolved in methanol (30 ml) and purged with nitrogen. To this solution, Pd (100 mg; 10% on carbon) was added, in 2 portions. After stirring at room temperature for 15 hours, the reaction mixture was filtered and the solvent was evaporated.

FORMULATION EXAMPLES FOR COMPOUNDS OF FORMULA (I)

Working procedures for preparing formulations of the compounds of formula I such as Emulsifiable Concentrates, Solutions, Granules, Dusts and Wettable Powders are described in WO97/33890.

BIOLOGICAL EXAMPLES: FUNGICIDAL ACTIONS

Example B-1

Action Against *Puccinia recondita*/wheat
(Brownrust on Wheat)

1 week old wheat plants cv. Arina are treated with the formulated test compound (0.02% active ingredient) in a spray chamber. One day after application, the wheat plants are inoculated by spraying a spore suspension ($1 \times 10^5$ uredospores/ml) on the test plants. After an incubation period of 2 days at 20° C. and 95% r.h. the plants are kept in a greenhouse for 8 days at 20° C. and 60% r.h. The disease incidence is assessed 10 days after inoculation.

Infestation is prevented virtually completely (0-5% infestation) with each of compounds 1.01, 1.03, 1.08, 1.10, 1.12, 1.13, 1.15, 1.16, 1.18, 1.19, 1.22, 1.24, 1.33, 1.56, 1.57, 1.60, 1.66, 1.67, 1.69, 1.70, 1.77, 1.78, 1.81, 1.106, 1.107, 1.138, 1.139, 1.151, 1.152, 1.154, 1.155, 1.182, 1.185, 1.251, 1.252, 2.01, 2.08, 2.66, 3.01, 3.08, 3.12, 3.18, 3.32, 3.56, 3.66, 3.69, 3.250, 9.01, 9.06, 9.15, 9.21, 9.41, 9.50, 9.53, 9.59, 15.25, 15.26 and 15.28.

Example B-2

Action Against *Podosphaera leucotricha*/apple
(Powdery Mildew on Apple)

5 week old apple seedlings cv. McIntosh are treated with the formulated test compound (0.02% active ingredient) in a spray chamber. One day after, the application apple plants are inoculated by shaking plants infected with apple powdery mildew above the test plants. After an incubation period of 12 days at 22° C. and 60% r.h. under a light regime of 14/10 hours (light/dark) the disease incidence is assessed.

Infestation is prevented virtually completely (0-5% infestation) with each of compounds. 1.01, 1.03, 1.08, 1.10, 1.12, 1.13, 1.15, 1.16, 1.18, 1.19, 1.24, 1.33, 1.35, 1.36, 1.56, 1.57, 1.66, 1.67, 1.70, 1.77, 1.78, 1.81, 1.106, 1.107, 1.139, 1.151, 1.152, 1.154, 1.155, 1.182, 1.185, 1.251, 1.252, 2.01, 2.08, 2.66, 3.01, 3.08, 3.12, 3.18, 3.32, 3.35, 3.56, 3.66, 3.69, 3.250, 9.01, 9.06, 9.15, 9.21, 9.41, 9.50, 9.53, 9.59, 9.62, 15.25, 15.26 and 15.28.

Example B-3

Action Against *Venturia inaegualis*/apple (Scab on Apple)

4 week old apple seedlings cv. McIntosh are treated with the formulated test compound (0.02% active ingredient) in a spray chamber. One day after application, the apple plants are inoculated by spraying a spore suspension ($4 \times 10^5$ conidia/ml) on the test plants. After an incubation period of 4 days at 21° C. and 95% r.h. the plants are placed for 4 days at 21° C. and 60% r.h. in a greenhouse. After another 4 day incubation period at 21° C. and 95% r.h. the disease incidence is assessed.

Infestation is prevented virtually completely (0-5% infestation) with each of compounds. 1.01, 1.03, 1.08, 1.10, 1.12, 1.13, 1.18, 1.19, 1.24, 1.33, 1.56, 1.57, 1.66, 1.67, 1.69, 1.70, 1.77, 1.78, 1.81, 1.106, 1.107, 1.138, 1.152, 1.154, 1.155, 1.251, 1.252, 2.01, 2.08, 2.66, 3.01, 3.08, 3.12, 3.18, 3.32, 3.56, 3.66, 3.69, 9.01, 9.06, 9.15, 9.21, 9.50 and 9.59.

Example B-4

Action Against *Erysiphe graminis*/barley (Powdery Mildew on Barley)

1 week old barley plants cv. Regina are treated with the formulated test compound (0.02% active ingredient) in a spray chamber. One day after application, the barley plants are inoculated by shaking powdery mildew infected plants above the test plants. After an incubation period of 6 days at 20° C./18° C. (day/night) and 60% r.h. in a greenhouse the disease incidence is assessed.

Infestation is prevented virtually completely (0-5% infestation) with each of compounds 1.01, 1.03, 1.08, 1.10, 1.12, 1.13, 1.15, 1.16, 1.18, 1.19, 1.24, 1.33, 1.35, 1.36, 1.56, 1.57, 1.66, 1.67, 1.70, 1.77, 1.78, 1.106, 1.107, 1.152, 1.155, 1.251, 1.252, 2.01, 2.08, 2.66, 3.01, 3.08, 3.12, 3.18, 3.32, 3.35, 3.56, 3.66, 3.69, 3.250, 9.01, 9.06, 9.15, 9.21, 9.41, 9.50 and 9.59.

Example B-5

Action Against *Botrytis cinerea*/grape (Botrytis on Grapes)

5 week old grape seedlings cv. Gutedel are treated with the formulated test compound (0.02% active ingredient) in a spray chamber. Two days after application, the grape plants are inoculated by spraying a spore suspension ($1 \times 10^6$ conidia/ml) on the test plants. After an incubation period of 4 days at 21° C. and 95% r.h. in a greenhouse the disease incidence is assessed.

Infestation is prevented virtually completely (0-5% infestation) with each of compounds 1.01, 1.03, 1.08 and 1.10.

Example B-6

Action Against *Botrytis cinerea*/tomato (Botrytis on Tomatoes)

4 week old tomato plants cv. Roter Gnom are treated with the formulated test compound (0.02% active ingredient) in a spray chamber. Two days after application, the tomato plants are inoculated by spraying a spore suspension ($1 \times 10^5$ conidia/ml) on the test plants. After an incubation period of 4 days at 20° C. and 95% r.h. in a growth chamber the disease incidence is assessed.

Infestation is prevented virtually completely (0-5% infestation) with each of compounds 1.01, 1.03, 1.08, 1.10, 1.12, 1.13, 1.15, 1.16, 1.18, 1.19, 1.24, 1.33, 1.36, 1.56, 1.57, 1.66, 1.67, 1.69, 1.70, 1.77, 1.78, 1.106, 1.107, 1.138, 1.139, 1.152, 1.155, 1.251, 1.252, 2.01, 2.66, 3.01, 3.08, 3.12, 3.66, 3.69, 3.250, 9.06, 9.15, 9.21, 9.41, 9.50 and 9.59.

Example B-7

Action Against *Septoria Nodorum*/wheat (Setoria Leaf Spot on Wheat)

1 week old wheat plants cv. Arina are treated with the formulated test compound (0.02% active ingredient) in a spray chamber. One day after application, the wheat plants are inoculated by spraying a spore suspension ($5 \times 10^5$ conidialml) on the test plants. After an incubation period of 1 day at 20° C. and 95% r.h. the plants are kept for 10 days at 20° C. and 60% r.h. in a greenhouse. The disease incidence is assessed 11 days after inoculation.

Infestation is prevented virtually completely (0-5% infestation) with each of compounds 1.01, 1.03, 1.08 and 1.10.

Example B-8

Action Against *Helminthosporium teres*/barley (Net Blotch on Barley)

1 week old barley plants cv. Regina are treated with the formulated test compound (0.02% active ingredient) in a spray chamber. Two days after application, the barley plants are inoculated by spraying a spore suspension ($3 \times 10^4$ conidia/ml) on the test plants. After an incubation period of 4 days at 20° C. and 95% r.h. in a greenhouse the disease incidence is assessed.

Infestation is prevented virtually completely (0-5% infestation) with each of compounds 1.01, 1.03, 1.08, 1.10, 1.12, 1.13, 1.15, 1.16, 1.18, 1.19, 1.22, 1.24, 1.33, 1.36, 1.35, 1.56, 1.57, 1.60, 1.66, 1.67, 1.69, 1.70, 1.77, 1.78, 1.81, 1.106, 1.107, 1.138, 1.139, 1.151, 1.152, 1.154, 1.155, 1.182, 1.185, 1.251, 1.252, 2.01, 2.08, 2.66, 3.01, 3.08, 3.12, 3.18, 3.32, 3.35, 3.56, 3.66, 3.69, 9.01, 9.06, 9.15, 9.21, 9.41, 9.50, 9.53, 9.59, 9.62, 15.25, 15.26 and 15.28.

Example B-9

Action Against *Alternaria solani*/tomato (Early Blight on Tomatoes)

4 week old tomato plants cv. Roter Gnom are treated with the formulated test compound (0.02% active ingredient) in a spray chamber. Two days after application, the tomato plants are inoculated by spraying a spore suspension ($2 \times 10^5$ conidia/ml) on the test plants. After an incubation period of 3 days at 20° C. and 95% r.h. in a growth chamber the disease incidence is assessed.

Infestation is prevented virtually completely (0-5% infestation) with each of compounds 1.01, 1.03, 1.08, 1.10, 1.13, 1.15, 1.16, 1.19, 1.22, 1.24, 1.33, 1.35, 1.36, 1.56, 1.57, 1.67, 1.69, 1.70, 1.77, 1.78, 1.81, 1.107, 1.151, 1.152, 1.154, 1.155, 1.182, 1.185, 1.251, 1.252, 2.01, 3.01, 3.08, 3.12, 3.32, 3.35, 3.56, 3.69, 9.01, 9.06, 9.15, 9.41, 9.50, 9.62 and 15.26.

Example B-10

Action Against *Uncinula necator*/grape (Powdery Mildew on Grapes)

5 week old grape seedlings cv. Gutedel are treated with the formulated test compound (0.02% active ingredient) in a spray chamber. One day after application, the grape plants are inoculated by shaking plants infected with grape powdery mildew above the test plants. After an incubation period of 7 days at 26° C. and 60% r.h. under a light regime of 14/10 hours (light/dark) the disease incidence is assessed.

Infestation is prevented virtually completely (0-5% infestation) with each of compounds 1.01, 1.03, 1.08, 1.10, 1.12, 1.13, 1.18, 1.19, 1.24, 1.33, 1.56, 1.57, 1.60, 1.66, 1.67, 1.70, 1.77, 1.78, 1.81, 1.106, 1.107, 1.138, 1.139, 1.151, 1.152, 1.154, 1.155, 1.182, 1.185, 1.251, 1.252, 2.01, 2.08, 2.66, 3.01, 3.08, 3.12, 3.32, 3.56, 3.66, 3.69, 3.250, 9.01, 9.06, 9.15, 9.41, 9.50, 9.53 and 9.59.

Example B-11

Action Against *Septoria tritici*/wheat (Septoria Leaf Spot on Wheat)

2 week old wheat plants cv. Riband are treated with the formulated test compound (0.2% active ingredient) in a spray chamber. One day after application, wheat plants are inoculated by spraying a spore suspension ($10 \times 10^5$ conidia/ml) on the test plants. After an incubation period of 1 day at 23° C. and 95% r.h., the plants are kept for 16 days at 23° C. and 60% r.h. in a greenhouse. The disease incidence is assessed 18 days after inoculation.

Compounds 1.10, 1.03, 1.09, 1.70, 1.69, 3.01, 1.67, 1.66, 3.66, 9.59, 3.69, 1.33, 2.66, 9.06, 3.08, 1.77, 1.78, 1.56, 1.57, 1.138, 1.139, 1.12, 1.18, 1.106, 1.107, 9.53, 3.32, 1.151, 1.152, 1.252, 1.155, 9.41, 3.56, 1.13, 3.12, 9.21, 1.250, 1.19 and 3.18. each show good activity in this test (<20% disease incidence).

The invention claimed is:

1. A compound of formula (I):

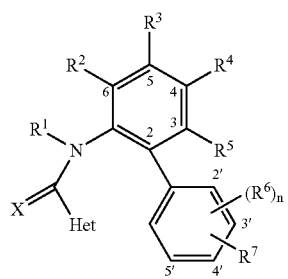

(I)

wherein:
Het is 1,2-diazole attached to the main structure in the 4-position, the ring being substituted by one, two or three groups $R^y$;
$R^1$ is hydrogen, formyl, CO—$C_{1-4}$ alkyl, COO—$C_{1-4}$ alkyl, $C_{1-4}$ alkoxy($C_{1-4}$)alkylene, CO—$C_{1-4}$ alkylenoxy ($C_{1-4}$)alkyl, propargyl or allenyl;
$R^2$, $R^3$, and $R^4$ are each, independently, hydrogen, halogen, methyl or $CF_3$;
$R^5$ is hydrogen or fluorine;
$R^6$ is, independently, halogen, methyl or $CF_3$;
$R^7$ is $(Z)_m C \equiv C(Y^1)$, or $(Z)_m C(Y^1) = C(Y^2)(Y^3)$;
each $R^y$ is, independently, halogen, $C_{1-3}$ alkyl, $C_{1-3}$ haloalkyl, $C_{1-3}$ alkoxy($C_{1-3}$)alkylene or cyano;
X is O or S;
$Y^1$, $Y^2$ and $Y^3$ are each, independently, hydrogen, halogen, $C_{1-6}$ alkyl [optionally substituted by one or more substituents each independently selected from halogen, hydroxy, $C_{1-4}$ alkoxy, $C_{1-4}$ haloalkoxy, $C_{1-4}$ alkylthio, $C_{1-4}$ haloalkylthio, $C_{1-4}$ alkylamino, di($C_{1-4}$)alkylamino, $C_{1-4}$ alkoxycarbonyl, $C_{1-4}$ alkylcarbonyloxy and tri($C_{1-4}$)alkylsilyl], $C_{2-4}$ alkenyl [optionally substituted by one or more substituents each independently selected from halogen], $C_{2-4}$ alkynyl [optionally substituted by one or more substituents each independently selected from halogen], $C_{3-7}$ cycloalkyl [optionally substituted by one or more substituents each independently selected from halogen, $C_{1-4}$ alkyl and $C_{1-4}$ haloalkyl] or tri($C_{1-4}$)alkylsilyl;
Z is $C_{1-4}$ alkylene [optionally substituted by one or more substituents each independently selected from hydroxy, cyano, $C_{1-4}$ alkoxy, halogen, $C_{1-4}$ haloalkyl, $C_{1-4}$ haloalkoxy, $C_{1-4}$ alkylthio, COOH and COO—$C_{1-4}$ alkyl];
m is 0 or 1; and
n is 0, 1 or 2.

2. A compound of formula (I) as claimed in claim 1 where $R^1$ is hydrogen, propargyl, allenyl, formyl, COMe, COEt or $COOH_2OMe$.

3. A compound of formula (I) as claimed in claim 1 where $Y^1$, $Y^2$ and $Y^3$ are, independently, hydrogen, halogen, $C_{1-5}$ alkyl, $C_{1-3}$ haloalkyl, $C_{1-4}$(haloalkoxy)$C_{1-4}$alkyl, $C_{1-4}$(haloalkylthio)$C_{1-4}$ alkyl, trimethylsilyl, $C_{2-4}$ alkenyl, $C_{2-4}$ haloalkenyl or $C_{3-6}$ cycloalkyl (optionally substituted by one or more substituents each independently selected from halogen and $C_{1-2}$ alkyl).

4. A compound of formula (I) as claimed in claim 1, where m=0.

5. A compound of formula (I) as claimed in claim 1, where Z is $C_{1-2}$ alkylene [which may be optionally substituted by one or more substituents each independently selected from halogen, $C_{1-4}$ haloalkyl and $C_{1-4}$ haloalkoxy].

6. A compound of formula (I) as claimed in claim 1, where $R^7$ is in the 4' position.

7. A compound of formula (I) as claimed in claim 1, where n=0.

8. A compound according to claim 1 wherein R7 is CH=CHSiMe$_3$, CH=CF$_2$, CH=CCl$_2$, CH=CBr$_2$, CF=CF$_2$, CCl=CH$_2$, CBr=CH$_2$, CF=CHF, CH=CHCF3, CH=CClCF$_3$, C≡CH, C≡CSiMe$_3$, C≡CCl, C≡CBr, C≡CCF$_3$, C≡CMe, C≡CCMe$_3$, C≡CCHMe$_2$, C≡C(cycloC$_3$H$_5$), CH$_2$C≡CH, SiMe$_3$ or CH$_2$C≡CSiMe$_3$.

9. A compound selected from 3-difluoromethyl-1-methyl-1H-pyrazole-4-carboxylic acid [4'-(3,3-dimethyl-but-1-ynyl)-biphenyl-2-yl]-amide and 3-difluoromethyl-1-methyl-1H-pyrazole-4-carboxylic acid (4'-prop-1-ynyl-biphenyl-2-yl)-amide.

10. A composition for controlling fungi and preventing attack and infestation of plants therewith, wherein the active ingredient is a compound of formula (I) as claimed in claim 1 together with a suitable carrier.

11. A method of controlling or preventing infestation of cultivated plants by phytopathogenic fungi by application of a compound of formula (I) as claimed in claim 1 to plants, to parts thereof or the locus thereof.

* * * * *

UNITED STATES PATENT AND TRADEMARK OFFICE
CERTIFICATE OF CORRECTION

PATENT NO. : 7,241,721 B2
APPLICATION NO. : 10/540036
DATED : July 10, 2007
INVENTOR(S) : Josef Ehrenfreund et al.

It is certified that error appears in the above-identified patent and that said Letters Patent is hereby corrected as shown below:

Claims 2 and 3 should read as follows:

Col. 62 lines 27-29
2. A compound of formula (I) as claimed in claim 1 where R1 is hydrogen, propargyl, allenyl, formyl, COMe, COEt or COCH2OMe.

Col. 62 lines 30-36
3. A compound of formula (I) as claimed in claim 1 where Y1, Y2 and Y3 are, independently, hydrogen, halogen, C1-6 alkyl, C1-3 haloalkyl, C1-4(haloalkoxy)C1-4alkyl, C1-4(haloalkylthio)C1-4 alkyl, trimethylsilyl, C2-4 alkenyl, C2 4 haloalkenyl or C3-6 cycloalkyl (optionally substituted by one or more substituents each independently selected from halogen and C1-2 alkyl).

Signed and Sealed this

Eighteenth Day of September, 2007

JON W. DUDAS
*Director of the United States Patent and Trademark Office*